(12) United States Patent
Alaie et al.

(10) Patent No.: US 12,275,184 B2
(45) Date of Patent: Apr. 15, 2025

(54) SYSTEMS AND METHODS FOR MICROPATTERNING OBJECTS

(71) Applicant: Cornell University, Ithaca, NY (US)

(72) Inventors: Seyedhamidreza Alaie, New York, NY (US); Simon Dunham, Ithaca, NY (US); Bobak Mosadegh, New York, NY (US); James K. Min, Brooklyn, NY (US); Amir Ali Amiri Moghadam, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 18/130,203

(22) Filed: Apr. 3, 2023

(65) Prior Publication Data

US 2023/0347571 A1 Nov. 2, 2023

Related U.S. Application Data

(63) Continuation of application No. 16/753,249, filed as application No. PCT/US2018/054233 on Oct. 3, 2018, now abandoned.
(Continued)

(51) Int. Cl.
*B29C 59/02* (2006.01)
*A61M 25/10* (2013.01)
(Continued)

(52) U.S. Cl.
CPC ....... *B29C 59/022* (2013.01); *A61M 25/1027* (2013.01); *B29C 33/40* (2013.01);
(Continued)

(58) Field of Classification Search
CPC ...... A61M 2025/1031; A61M 25/1027; B29C 2033/426; B29C 2037/0035;
(Continued)

(56) References Cited

U.S. PATENT DOCUMENTS 4,407,685 A 10/1983 Hankland
5,395,718 A * 3/1995 Jensen ............... H01Q 15/0013
430/311
(Continued)

FOREIGN PATENT DOCUMENTS

GB 1 493 348 11/1977
WO WO-2016/128494 A1 8/2016

OTHER PUBLICATIONS

Extended European Search Report for EP 18864625.1 DTD May 21, 2021, 10 pages.
(Continued)

*Primary Examiner* — John J DeRusso
*Assistant Examiner* — Victoria Bartlett
(74) *Attorney, Agent, or Firm* — Foley & Lardner LLP

(57) ABSTRACT

Implanted medical devices need a mechanism of immobilization to surrounding tissues, which minimizes tissue damage while providing reliable long-term anchoring. This disclosure relates to techniques for patterning arbitrarily shaped 3D objects and to patterned balloon devices having micro- or nano-patterning on an outer surface of an inflatable balloon. The external pattern can provide enhanced friction and anchoring in an aqueous environment. Examples of these types of patterns are hexagonal arrays inspired by tree frogs, corrugated patterns, and microneedle patterns. The patterned balloon devices can be disposed between an implant and surrounding tissues to facilitate anchoring of the implant.

21 Claims, 84 Drawing Sheets

Related U.S. Application Data

(60) Provisional application No. 62/567,625, filed on Oct. 3, 2017, provisional application No. 62/567,644, filed on Oct. 3, 2017.

(51) Int. Cl.
  *B29C 33/40* (2006.01)
  *B29C 33/42* (2006.01)
  *B29C 33/56* (2006.01)
  *B29C 37/00* (2006.01)
  *B29C 59/06* (2006.01)
  *B29K 83/00* (2006.01)
  *G03F 7/00* (2006.01)

(52) U.S. Cl.
  CPC ............ *B29C 33/424* (2013.01); *B29C 33/56* (2013.01); *B29C 37/0032* (2013.01); *B29C 59/021* (2013.01); *B29C 59/06* (2013.01); *G03F 7/0002* (2013.01); *A61M 2025/1031* (2013.01); *B29C 2033/426* (2013.01); *B29C 2037/0035* (2013.01); *B29C 2059/023* (2013.01); *B29K 2083/00* (2013.01); *B29K 2875/00* (2013.01)

(58) Field of Classification Search
  CPC .......... B29C 2059/023; B29C 37/0032; B29C 33/38; B29C 33/40; B29C 33/424; B29C 33/56; B29C 59/02; B29C 59/021; B29C 59/022; B29C 59/06; B29K 2083/00; B29K 2875/00; G03F 7/0002; B81C 99/0085; B81C 99/009
  See application file for complete search history.

(56) References Cited

U.S. PATENT DOCUMENTS

| | | | |
|---|---|---|---|
| 5,817,242 A | 10/1998 | Biebuyck et al. | |
| 6,136,126 A | 10/2000 | Fenzi | |
| 9,005,502 B2 * | 4/2015 | Chiba | B29C 33/40 264/220 |
| 9,193,199 B2 * | 11/2015 | Palone | B29C 59/026 |
| 11,163,230 B2 | 11/2021 | Verschuuren | |
| 2002/0050220 A1 | 5/2002 | Schueller et al. | |
| 2004/0131718 A1 | 7/2004 | Chou et al. | |
| 2005/0084613 A1 | 4/2005 | Wang et al. | |
| 2008/0157235 A1 | 7/2008 | Rogers et al. | |
| 2015/0150807 A1 | 6/2015 | Park et al. | |
| 2016/0051958 A1 | 2/2016 | Kung et al. | |
| 2016/0158977 A1 | 6/2016 | Ross | |
| 2018/0113390 A1 | 4/2018 | Patterson et al. | |

OTHER PUBLICATIONS

Final Office Action on U.S. Appl. No. 16/753,249 DTD Oct. 5, 2022.
International Preliminary Report on Patentability for Appl. Ser. No. PCT PCT/US2018/054233 DTD Apr. 16, 2020, 10 pages.
International Search Report and Written Opinion in International Application No. PCT/US2018/054233 mailed Jan. 24, 2019 (12 pages).
Non-Final Office Action on U.S. Appl. No. 16/753,249 DTD Jun. 16, 2022.
Office Action in EP 18864625.1, dated Feb. 8, 2023.
Zhang et al., A simple method for fabricating multi-layer PDMS structures for 3D microfluidic chips, Feb. 9, 2010, The Royal Society of Chemistry, vol. 10, pp. 1199-1203 (Year: 2010).

* cited by examiner

Photolithography

Spin Coating

Peel Off

FIG. 3E
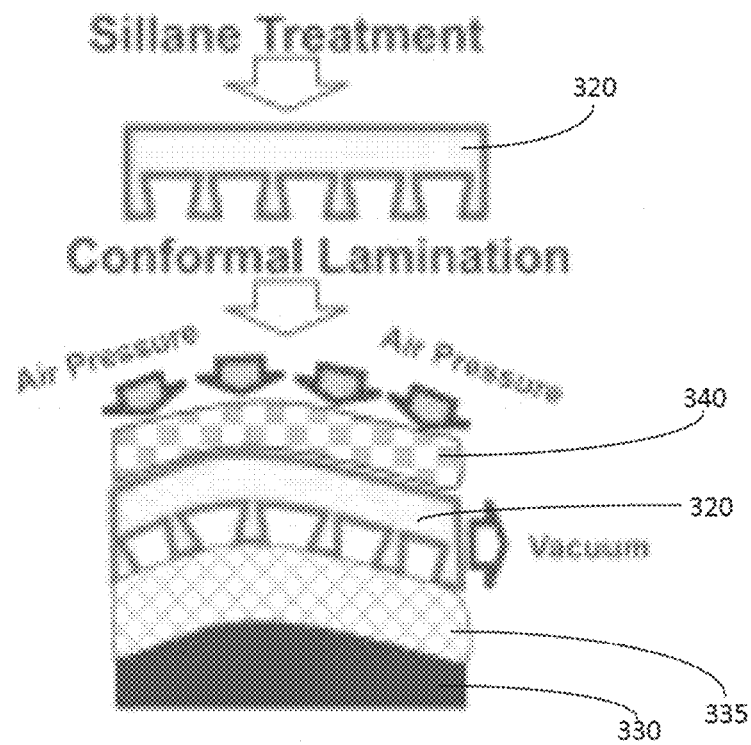
FIG. 3F
FIG. 3G
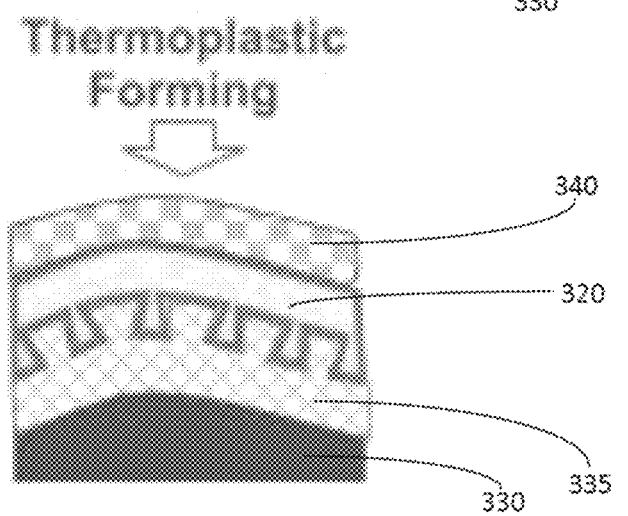

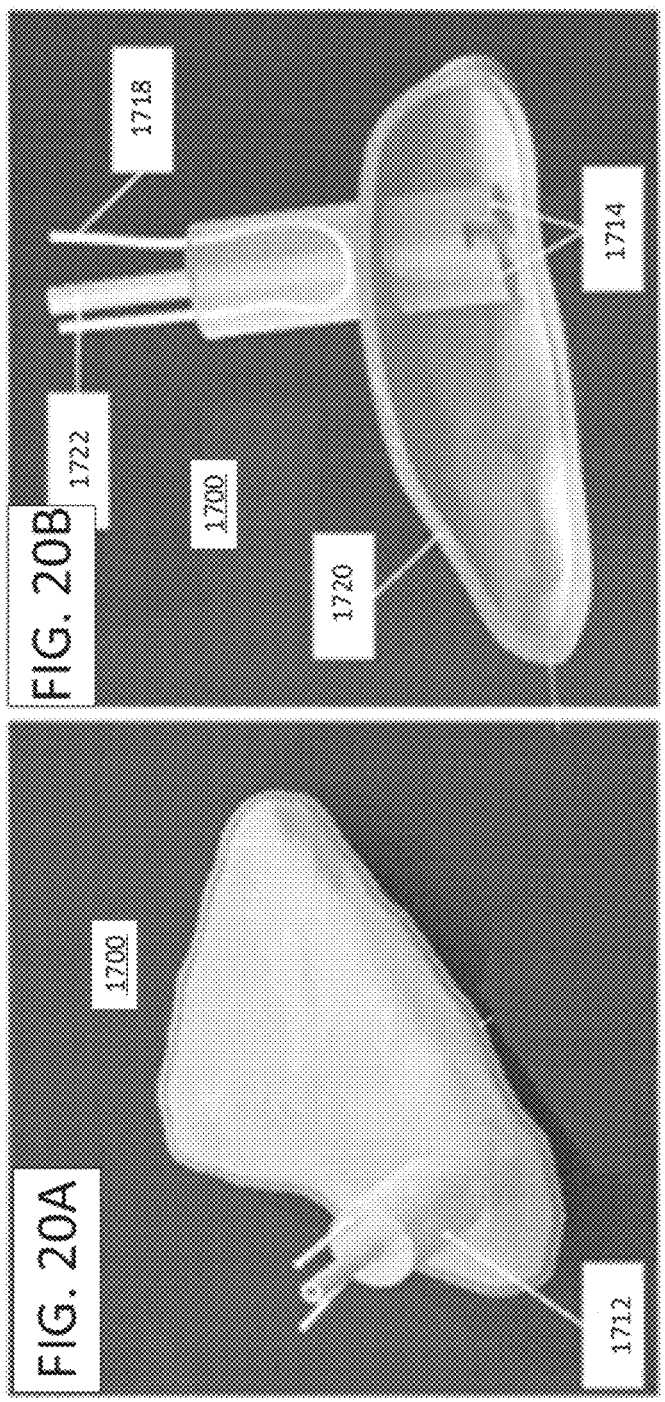

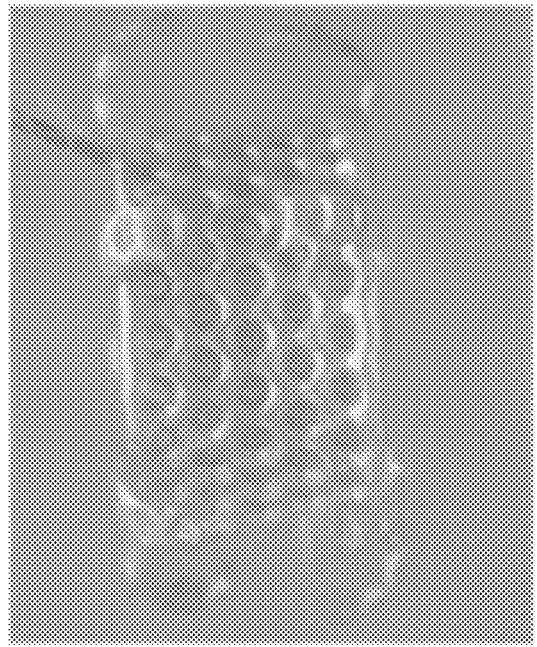
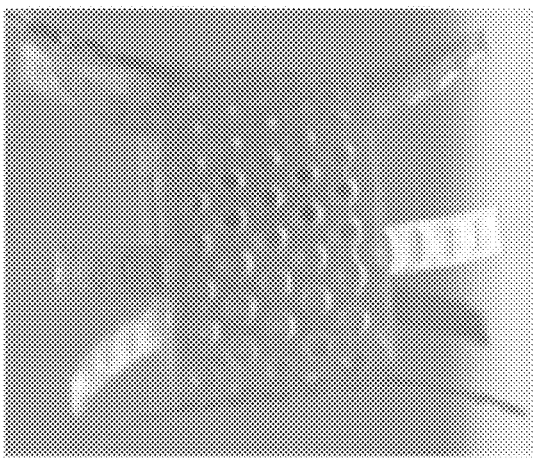
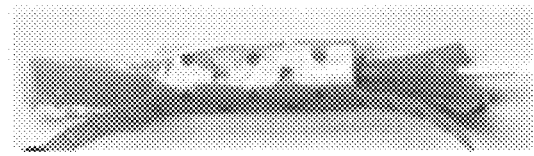
FIG. 27

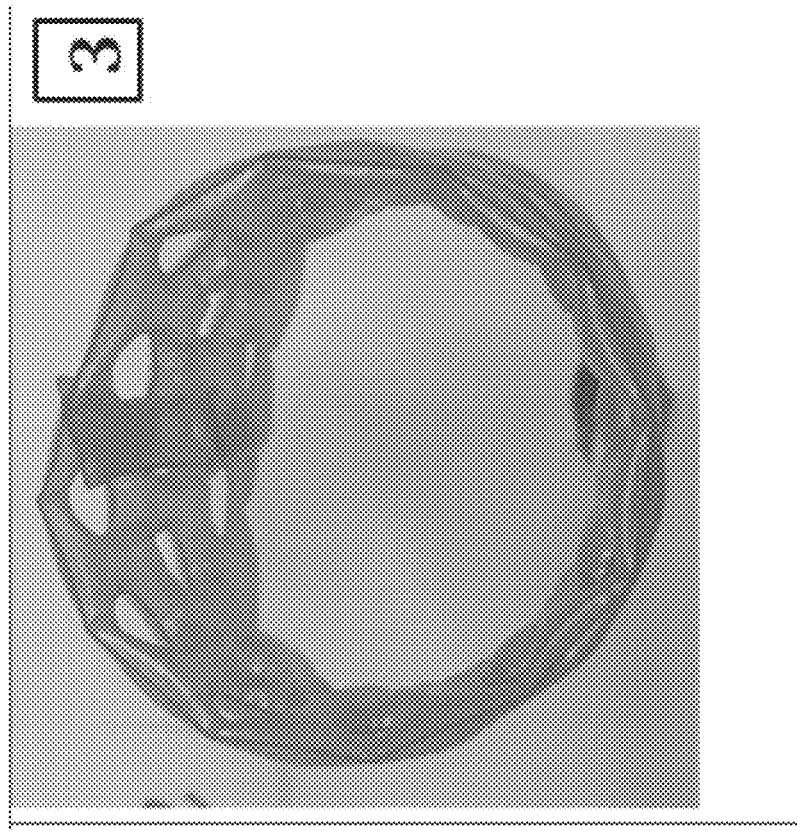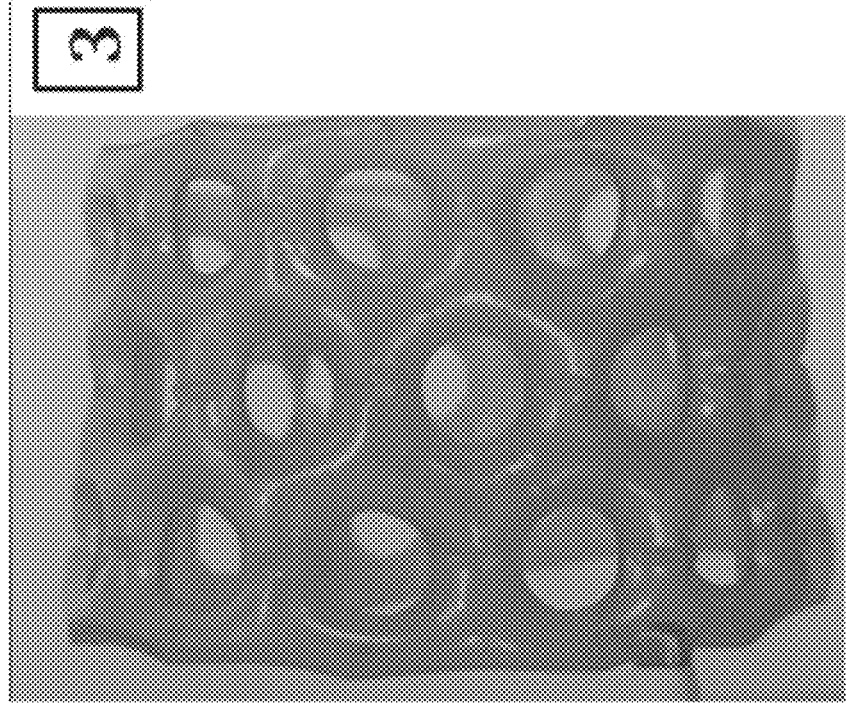
FIG. 48C

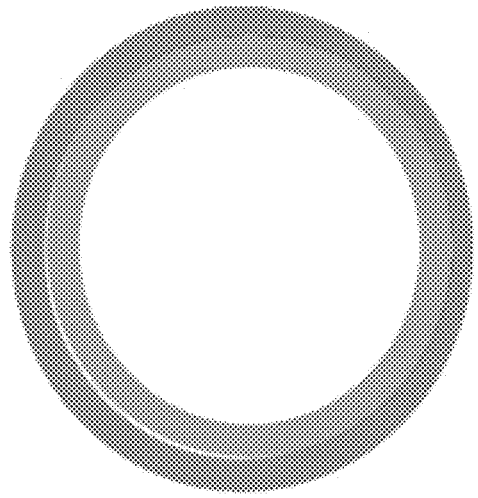
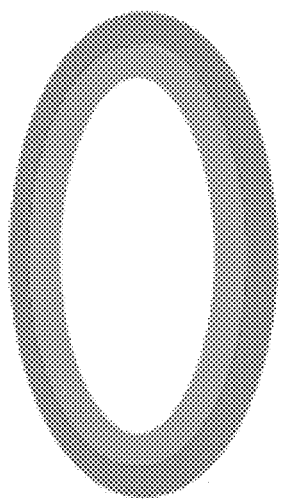
FIG. 50A

SYSTEMS AND METHODS FOR MICROPATTERNING OBJECTS

CROSS-REFERENCE TO RELATED APPLICATIONS

The present application is a Continuation of U.S. application Ser. No. 16/753,249, filed Apr. 2, 2020, and claims priority to International Patent Application No. PCT/US18/54233, filed Oct. 3, 2018 and titled "SYSTEMS AND METHODS FOR MICROPATTERNING OBJECTS," which claims priority to U.S. Provisional Patent Application No. 62/567,625, filed Oct. 3, 2017 and titled "MICROPATTERNED BALLOONS AND METHODS OF FABRICATION," and to U.S. Provisional Patent Application No. 62/567,644, filed Oct. 3, 2017 and titled "THIN INFLATABLE ACTUATORS AND METHODS OF CONSTRUCTION," each of which is incorporated herein by reference in its entirety.

FIELD

The subject matter disclosed herein generally relates to the field of medical devices and more specifically to method and composition of friction patterning of medical devices.

BACKGROUND

Micro-patterning can provide a powerful means for engineering surface properties, such as friction, adhesion, and biocompatibility, with promise for medical device applications. While soft lithography allows for micropatterning on curved surfaces, there are limitations to the level of curvature and object complexity achievable.

Medical implants are devices or tissues that are placed inside or on the surface of the body. Many implants are prosthetics, intended to replace missing body parts. Other implants deliver medication, monitor body functions, or provide support to organs and tissues. Some implants are made from skin, bone or other body tissues. Others are made from metal, plastic, ceramic or other commercially available materials. Implants can be placed permanently or they can be removed once they are no longer needed. For example, stents or hip implants are intended to be permanent. However, chemotherapy ports or screws to repair broken bones can be removed when they no longer needed.

Many implanted medical devices use wires or wireless radiofrequency telemetry to communicate with circuitry outside the body. However, the wires are a common source of surgical complications, including breakage, infection and electrical noise. In addition, radiofrequency telemetry requires large amounts of power and results in low-efficiency transmission through biological tissue. Therefore, there is a movement in the field to harness the conductive properties of the body to enable wireless communication between implanted devices and external devices.

There are considerable risks associated with medical device implantation, including surgical risks during placement or removal, infection, and implant failure. Depending on the type of implant, the complications may vary in their nature and severity. Some patients also experience reactions to the materials used in implant manufacture. Additionally, over time, the implant can move, break, or stop working properly. This may require additional surgery to repair or replace the implant. Furthermore, the interaction between the implant and the tissue surrounding the implant can lead to complications such as implant-induced blood coagulation.

SUMMARY

This disclosure relates in part to techniques for micropatterning surfaces of three-dimensional (3D) objects. The techniques disclosed herein can be used for a variety of micropatterns, materials, and devices. In some implementations, the principles of soft lithography for fabrication of flexible templates can be integrated with the principles of vacuum bagging, for transfer of the patterns on arbitrary shaped nonplanar objects. The technique is demonstrated herein with a variety of materials including silicones, polyurethanes, and Nitinol, which are ubiquitous in medical devices, due to their mechanics, biocompatibility, and hemocompatibility. Micro-patterns inspired by shark skin riblets and tree frogs are demonstrated. The flexibility of these techniques is demonstrated by transferring patterns to various objects/devices, including 3D printed objects, soft robotic grippers, guidewires, and balloon catheters.

The subject matter disclose herein also relates to a patterned balloon device including a balloon, which can be radially expanded from a deflated state with a first volume to an inflated state with a second volume greater than the first volume. In some implementations, the balloon has an outer surface wherein at least a portion of the outer surface comprises features arranged in a pattern. In some implementations, the pattern can increase the friction forces between the patterned balloon device and surrounding surfaces it comes in contact with. The patterned balloon device can reduce the likelihood of implant displacement within a subject's body, which can reduce the need for following surgical interventions and implant replacement. The surrounding surfaces can be the surface of an object, tissues, organs, any medical devices. In some implementations, the patterned balloon device is incorporated in the body of a medical implant and functions to secure or anchor the implant inside a subject's body.

In some implementations, the featured arranged in a pattern enhance friction with the application of pressure between tissues and the patterned surface of the balloon as shown and/or move fluid away from the interface between the patterned balloon surface and tissues, and/or deforms or penetrates tissues to increase surface area or provide mechanical interlocking. The pattern can be a hexagonal array. The pattern can also include cylindrical, rectangular, spherical, polygonal, triangular, circular, and ellipsoid features or any geometrical shape suitable for increasing contact friction or any combination thereof. In some implementations, the pattern is a corrugated pattern, which can deform tissues increasing the surface area of contact. The pattern can be a micro- or nano-pattern depending on the size of an individual feature in the pattern. In some implementations, the pattern covers at least a portion of the outer surface of the balloon.

The volumetric shape of the expandable balloon in an inflated state can conform to the contours of surrounding surfaces. The balloon can include a valve that is configured to enable passing of inflation fluid in a first direction into an interior of the balloon. The patterned balloon device can include inflation fluid. The inflation fluid can be introduced into the interior of a balloon through a lumen, which can gain access to the interior lumen of the balloon. The valve may substantially prevent the inflation fluid from moving in a second direction opposite to the first direction. The inflation fluid can be configured to fill the interior volume of the balloon to expand the balloon from a deflated state to an inflated state. The inflation fluid can be a curable fluid. The inflation fluid can be configured to cure upon an exposure to one of an ultraviolet energy or a thermal energy. The inflation fluid can include at least one of an epoxy, polyethylene glycol, or a collagen-based polymeric gel. The inflation fluid can include at least one of saline and a self-expanding foam.

In some implementations, the patterned balloon device can be a subject-specific patterned balloon device and the balloon can be manufactured to fit the curvature of a specific body cavity upon expansion where the implant is to be positioned. The patterned balloon device can include one or more lobes. In some implementations, a first lobe can include a first volumetric shape and a second lobe can include a second volumetric shape that is different than the first volumetric shape. The patterned balloon device can include a first lobe with a first axis and a second lobe with a second axis that is askew from the first axis.

The subject matter disclosed herein also relates to a method of fabrication of a patterned balloon device. The method includes fabricating a thin-walled balloon by means known in the art such as blow molding, dip coating, vacuum bagging, or conventional molding or casting or a combination thereof. In some implementations, the balloon is prefabricated in the shape desired for the application and may be subject-specific. In some implementations, the pattern can be embossed in the outer surface of the balloon. In some other implementations, the pattern can be fabricated on a planar template generating a pattern master. The pattern can then be transferred to the surface of the balloon or it can be transferred to an elastomeric material which can be attached to the outer surface of the balloon.

The subject matter disclosed herein further relates to a method for immobilizing a medical implant in a body cavity including deploying an expandable patterned balloon device in the body cavity. The patterned balloon device includes an array of features arranged in a pattern, which can increase friction between the implant and surrounding tissues, thus, facilitating immobilization of the implant. The features can be a plurality of geometric shapes and can be disposed on at least a portion of the outer surface of the patterned balloon device. The patterned balloon device can further include a plurality of lobes. A volumetric shape of the patterned balloon device in an inflated state can be configured to complement the curvature of surrounding tissue surfaces. The patterned balloon device can include a valve that is configured to enable a lumen to pass into an interior volume of the patterned balloon device in a first direction and substantially prevent an inflation fluid from flowing in a second direction that is opposite the first direction. The method can include filling the expandable balloon with an inflation fluid or gas. The inflation fluid or gas can be configured to fill the interior volume of the expandable balloon to expand the patterned balloon device from a deflated state to an inflated state. The method can include anchoring the patterned balloon device to a tissue surface.

In some implementations, the method can include removing the lumen from the valve. The valve can include a polymeric septum that is configured to seal a location pierced by the lumen. The method can include curing the inflation fluid by exposing the inflation fluid to at least one of an ultraviolet energy or a thermal energy. The inflation fluid can include at least one of an epoxy, polyethylene glycol or a collagen-based polymeric gel. The inflation fluid can include at least one of saline and a self-expanding foam. The first lobe can include a first volumetric shape and the second lobe can include a second volumetric shape that is different than the first volumetric shape. The patterned balloon device can include there of more lobes. The patterned balloon device can include the first lobe with a first axis and the second lobe with a second axis that is askew from the first axis.

Another aspect of the present disclosure relates to a method for patterning an object. The method may include providing a 3D object. The method may include micropatterning a rigid material via photolithography. The method may include fabricating a flexible stamp having a micropattern on its surface using the micropatterned rigid material. The method may include wrapping the 3D object in the flexible stamp. The method may include inserting the 3D object, the flexible stamp, and a breather film into a vacuum bag. The method may include applying vacuum to the 3D object and the flexible stamp. The method may include transferring the micropattern of the flexible stamp to a surface of the 3D object. For example, the micropattern can be transferred to the surface of the 3D object by applying heat to the 3D object, the flexible stamp, and a breather film to cause a surface of the 3D object to be imprinted with the micropattern of the flexible stamp.

In some implementations of the method, micropatterning the rigid material via photolithography may include micropatterning a silicon wafer.

In some implementations of the method, the flexible stamp may include an elastomeric film.

In some implementations of the method, the flexible stamp may have a thickness between 20 and 500 microns.

In some implementations of the method, the micropattern may have a thickness between one microns and 40 microns.

In some implementations of the method, it may include further including fabricating a flexible stamp by inverting the micropatterned rigid material to form a soft template having the micropattern on its surface. In some implementations of the method, it may include coating the soft template with an elastomeric material curing the elastomeric material to form the flexible stamp. In some implementations of the method, it may include and peeling the flexible stamp off of the soft template.

In some implementations of the method, the soft template may include silicone.

In some implementations of the method, it may include further including applying treatment to a surface of the soft template.

In some implementations of the method, the surface treatment may include trichloro perfluoro silane.

In some implementations of the method, the 3D object may be formed from at least one of silicone, nitinol alloy, and polyurethane.

In some implementations of the method, it may include further including treating a surface of the 3D object to promote adhesion of the flexible stamp to the 3D object.

Another aspect of the present disclosure relates a micropatterned object. The micropatterned object can be formed by performing a set of steps. The steps may include providing a 3D object. The steps may include micropatterning a rigid material via photolithography. The steps may include fabricating a flexible stamp having a micropattern on its surface using the micropatterned rigid material. The steps may include wrapping the 3D object in the flexible stamp. The steps may include inserting the 3D object, the flexible stamp, and a breather film into a vacuum bag. The steps may include applying vacuum to the 3D object, the flexible stamp. The breather film within the vacuum bag. The steps may include transferring the micropattern of the flexible stamp to a surface of the 3D object. For example, the micropattern may be transferred to the surface of the 3D object by applying heat to the 3D object, the flexible stamp, and a breather film to cause a surface of the 3D object to be imprinted with the micropattern of the flexible stamp.

Another aspect of the present disclosure relates to a method for manufacturing an implantable device. The method may include positioning a first portion of an inflatable balloon over a first portion of a sacrificial core. The method may include positioning a second portion of the inflatable balloon over a second upper portion of the sacrificial core such that the second portion of the inflatable balloon at least partially overlaps the first portion of the inflatable balloon. The method may include applying vacuum to the first portion of the inflatable balloon and the second portion of the inflatable balloon via a vacuum bag assembly. The method may include applying heat to the first portion of the inflatable balloon and the second portion of the inflatable balloon to form a thermoplastic bond between the first portion of the inflatable balloon and the second portion of the inflatable balloon. The method may include dissolving the sacrificial core.

In some implementations, the method may include inserting a septum into a hole in the sacrificial core. The method may include positioning a third portion of the inflatable balloon over the first portion of the inflatable balloon. The method may include positioning a fourth portion of the inflatable balloon over the second portion of the inflatable balloon such that the fourth portion of the inflatable balloon at least partially overlaps the third portion of the inflatable balloon. The method may include applying vacuum to the third portion of the inflatable balloon, the fourth portion of the inflatable balloon, and the septum. The method may include applying heat to the third portion of the inflatable balloon, the fourth portion of the inflatable balloon, and the septum to form a thermoplastic bond between the first portion of the inflatable balloon, the second portion of the inflatable balloon, the third portion of the inflatable balloon, the fourth portion of the inflatable balloon, and the septum.

In some implementations of the method, it may include wrapping the third portion of the inflatable balloon and the fourth portion of the inflatable balloon in a micropatterned stamp prior to applying the vacuum and the heat to the third portion of the inflatable balloon and the fourth portion of the inflatable balloon to impart micropatterned features on at least a portion of the surface of the inflatable balloon.

In some implementations of the method, it may include micropatterning a silicon wafer via photolithography. In some implementations of the method, it may include inverting the micropatterned silicon wafer to form a master template. In some implementations of the method, it may include spin coating the master template with an elastomeric material. In some implementations of the method, it may include curing the elastomeric material to form the micropatterned stamp. In some implementations of the method, it may include peeling the micropatterned stamp off of the master template.

In some implementations of the method, it may include pressure forming a first film on a lower portion of a three-dimensional mold to form the first portion of the inflatable balloon. In some implementations of the method, it may include pressure forming a second film on an upper portion of the 3D mold to form the second portion of the inflatable balloon.

In some implementations of the method, it may include dissolving dry pellets of a resin material. In some implementations of the method, it may include spin coating the dissolved resin on a flat template to form at least one of the first film and the second film.

In some implementations of the method, the resin material may include polyurethane.

In some implementations of the method, at least one of the first film and the second film may have a thickness between 30 microns and 40 microns.

In some implementations of the method, it may include constructing a 3D mold of a septum using an additive manufacturing technique. In some implementations of the method, it may include inverting the 3D mold on a silicone mold. In some implementations of the method, it may include filling the silicone mold with dry resin pellets. In some implementations of the method, it may include applying heat and vacuum to the silicone mold and the dry resin pellets to form the septum. In some implementations of the method, it may include removing the septum from the silicone mold. In some implementations of the method, it may include inserting the septum into a hole in the sacrificial core.

In some implementations of the method, dissolving the sacrificial core may further include puncturing the septum. In some implementations of the method, dissolving the sacrificial core may further include coupling the inflatable balloon to a perfusion system. In some implementations of the method, dissolving the sacrificial core may further include circulating water through an interior of the inflatable balloon via the perfusion system to dissolve the sacrificial core.

In some implementations of the method, it may include wrapping an elastomeric string around the first portion of the inflatable balloon and the second portion of the inflatable balloon prior to applying heat to the first portion of the inflatable balloon and the second portion of the inflatable balloon.

In some implementations of the method, it may include constructing a 3D mold of the sacrificial core using an additive manufacturing technique. In some implementations of the method, it may include inverting the 3D mold on a silicone mold. In some implementations of the method, it may include introducing a slurry into the silicone mold. In some implementations of the method, it may include applying heat and vacuum to the silicone mold to cause the slurry to form the sacrificial core. In some implementations of the method, it may include removing the sacrificial core from the silicone mold.

Another aspect of the present disclosure relates to an implantable device. The implantable device can be formed by performing a set of steps. The steps may include positioning a first portion of an inflatable balloon over a lower portion of a sacrificial core. The steps may include positioning a second portion of the inflatable balloon over an upper portion of the sacrificial core such that the second portion of the inflatable balloon at least partially overlaps the first portion of the inflatable balloon. The steps may include applying vacuum to the first portion of the inflatable balloon and the second portion of the inflatable balloon via a vacuum bag assembly. The steps may include applying heat to the first portion of the inflatable balloon and the second portion of the inflatable balloon to form a thermoplastic bond between the first portion of the inflatable balloon and the second portion of the inflatable balloon. The steps may include dissolving the sacrificial core.

In some implementations, the steps may include inserting a septum into a hole in the sacrificial core. The steps may include positioning a third portion of the inflatable balloon over the first portion of the inflatable balloon. The steps may include positioning a fourth portion of the inflatable balloon over the second portion of the inflatable balloon such that the fourth portion of the inflatable balloon at least partially overlaps the third portion of the inflatable balloon. The steps may include applying vacuum to the third portion of the inflatable balloon, the fourth portion of the inflatable balloon, and the septum. The steps may include applying heat to the third portion of the inflatable balloon, the fourth portion of the inflatable balloon, and the septum to form a thermoplastic bond between the first portion of the inflatable balloon, the second portion of the inflatable balloon, the third portion of the inflatable balloon, the fourth portion of the inflatable balloon, and the septum.

BRIEF DESCRIPTION OF FIGURES

The figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, and emphasis is instead being placed upon illustrating the principles of the teachings. The drawings are not intended to limit the scope of the present teachings in any way. The system and method may be better understood from the following illustrative description with reference to the following drawings in which:

FIGS. 3A-3H show stages of construction of a micropatterned 3D object according to the method of FIG. 2.

FIG. 20A illustrates a cross-sectional view of an example patterned balloon device in an uninflated state.

FIG. 20B illustrates a cross-sectional view of an example patterned balloon device in an inflated state.

FIG. 26A shows an unactuated bending soft robotic device with a flat geometry. FIG. 26B shows an actuated bending soft robotic device with a flat geometry. FIG. 26C shows an unactuated soft robotic device with complex geometry. FIG. 26D shows an actuated soft robotic device with complex geometry.

FIG. 27 depicts three conformations of a heart valve embodiment of a soft robotic device: a rolled up, low-volume conformation on the left; an unactuated conformation in center; and an actuated conformation on the right.

In FIG. 28A, layers of thermoplastic polyurethane are laminated using a heat press. FIG. 28B shows a laser beam cutting/welding the laminated layers to a desired pattern. FIG. 28C shows the inflated chamber bounded by layers 1 and 3 disposed on each side; the asymmetry of the layer stiffness leads to a bending motion.

FIG. 29A depicts a sequence of images showing the bending motion of a soft robotic device of type I. FIG. 29B shows a heat-map of maximum principle strain in different portions of the bending device while in ultimate bent configuration. FIG. 29C shows a comparison between the simulated and experimental lateral displacements of a thin soft robotic device using FEM simulation.

FIG. 30A shows an asymmetric 2D profile for a soft robotic device of type II. FIG. 30B depicts a sequence of images showing the bending motion of soft robotic device of type II. FIG. 30C shows a comparison of the ultimate bending configuration of the soft robotic device with that of FEM simulation. FIG. 30D shows a comparison between simulated and experimental lateral displacements of the thin soft robotic device.

FIG. 31A shows a rotary soft robotic device with a 300° rotation capability. FIG. 31B shows a axial soft robotic device. FIG. 31C a biaxial soft robotic device in an unactuated and an actuated conformations.

FIG. 32A depicts a schematic of a bi-directional soft robotic device and design of its working principle. FIG. 32B shows images of the unactuated, open, and closed conformations for this thin soft robotic device. FIG. 32C depicts how these different conformations grasp objects for the pick and place task.

FIG. 34A shows a sequence of swimming motion for one cycle. FIG. 34B depicts the pressure inside the soft robotic device during the inflation and deflation periods. FIG. 34C shows the horizontal displacement of the soft robotic device during the inflation and deflation phases. FIG. 34D shows the total displacement after 7 cycles (14 sec).

FIG. 18A shows several depictions of a heart valve in actuated and unactuated conformations. FIG. 42B depicts change in pressure over time as the heart valve is opened and closed. FIG. 42C shows changes in pressure as flow rate increases.

FIG. 45A shows a honeycomb pattern on a flat plain balloon. FIG. 21 B shows a patterned balloon, which can be bent to from a stent. FIG. 45C shows a soft stent in its low-volume conformation. FIG. 45D shows a stent in its deflated conformation. FIG. 45E shows a stent in its inflated conformation connected to an inflation source. FIG. 45F shows a stent in its inflated conformation.

FIGS. 48A-48D show views of different patterns for the stent.

FIG. 50A shows a set of realistic annulus shapes.

DETAILED DESCRIPTION

Figure 1B:
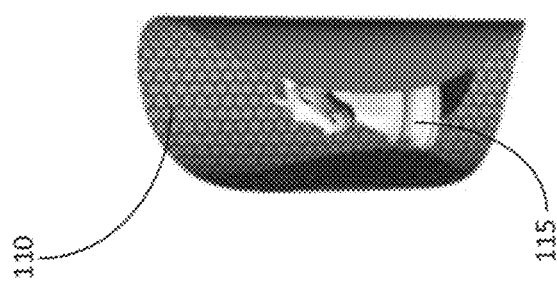
FIGS. 1A-1D show stages of construction of a general process for patterning a 3D object.

For purposes of reading the description of the various implementations below, the following descriptions of the sections of the specification and their respective contents may be helpful:

Section A describes techniques for micropatterning arbitrarily shaped three-dimensional (3D) objects;

Section B describes micropatterned implantable balloons; and

Section C describes thin inflatable actuators.

A. Micropatterning 3D Objects

Micro- and/or Nano-patterning of surfaces can be a powerful technique for engineering the surface properties of devices or objects without changing their underlying chemistry, functionality, and bulk properties. These techniques allow engineering of surface properties, such as adhesion, wettability, and optical properties, and can be used to regulate cell behavior. While there are a myriad of approaches to fabricate micro-patterned surfaces, such as using self-assembly, electrostatic forces, phase shift lithography, and other phenomena, these methods are typically limited to specific types of patterns and planar substrates, and are often costly and time-consuming Some soft lithographic techniques can allow for the transfer of micro-patterns from 2D prefabricated templates to objects of interest. For example, a pattern can be molded onto a flexible stamp, which can conform to the surface of an object. Then the transfer can be accomplished by solvent-assisted embossing, hot embossing, or imprint lithography. These approaches can benefit from the high resolution of 2D microfabrication, but can only be used on small radius of curvature substrates or objects with individual bends. Therefore, more recently flexible phase shift masks evolved as a powerful tool for patterning of photopolymers on complex surfaces. A significant amount of work has been devoted to advancing the type and complexity of features that can be transferred by these techniques. However, less effort has been focused on expanding the type and complexity of objects that can be patterned, and the ease and cost effectiveness of patterning.

There are several challenges that must be addressed to apply soft lithographic approaches to more complex objects. For example, the stamp must be able to conform to a complex shape without dramatically stretching or folding, the stamp must be applied uniformly to the surface of the object with equal pressure without inducing stamp deformation or stamp collapse, and the stamp must contact the object without inducing air bubbles or other defects. To address these three challenges, this disclosure provides a variety of techniques, such as vacuum bagging, which was originally developed for lamination of fabrics, resins, and fabric/resin composite materials into complex 3D geometries. In general, vacuum bagging applies a uniform pressure on an object by inducing a differential pressure between the inside and outside of a bag made from thin and conformable films. Although this technology has matured extensively in large manufacturing, its use for micro-fabrication has not been explored in depth prior to this disclosure.

One aspect of this disclosure relates to a novel approach that relies on ultra-thin conformable micro-patterned stamps in conjunction with vacuum bagging. This technique can be referred to herein as conformal template vacuum bagging (CTVB). The flexibility of the stamps can be combined with various advantages of the vacuum bagging process, including uniform pressure distributions along the object surface, inert reaction environments while embossing, and the ability to infuse resins into gas-free templates, thus preventing air bubbles or defects. These features address some key technical challenges of surface micropatterning of complex 3D objects. Furthermore, because vacuum bagging is a robust, inexpensive, and well-established technology, this method can be applied simply with inexpensive equipment and is easily scalable for manufacturing. Finally, because the vacuum bag can conform to almost any geometry, the method does not require the operator to know the object geometry in advance, dramatically improving the versatility and ease of use.

The techniques described in this disclosure can have application in the field of medical implants and devices, as described further below in connection with Section B. The techniques have been demonstrated for a variety of materials common to the medical device industry due to their mechanical properties and biocompatibility, namely silicone, nitinol alloy, and polyurethanes (Tecoflex™ polyurethane, and ChronoFlex® polycarbonate-urethane). Polyurethanes can have a wide range of mechanical properties (elongation at break, shore hardness, and ultimate strength) that are useful for engineering composite implants. In some implementations, patterns can be hexagonal surface micropatterns inspired by tree frogs and sharkskin riblets, which have been shown to enhance wet friction, and to decrease interfacial shear stresses, respectively. These patterns can have great potential to medical device applications, but are also easily applied to any 2D surface micropattern. To illustrate the versatility of this method, a variety of objects were selected and patterned, as described further below. For example, this disclosure provides example of micropatterned 3D objects including a 3D printed chess piece, a super-elastic nitinol guidewire after heat treatment, a Foley catheter, and a soft robotic star shaped gripper made from silicone. This disclosure also describes several variants of this approach to generate surface patterns through resin infusion or thermoforming/embossing. These techniques allow for a cost-effective integration of rapid prototyping with lithography for a variety of materials and objects.

Figure 1A:
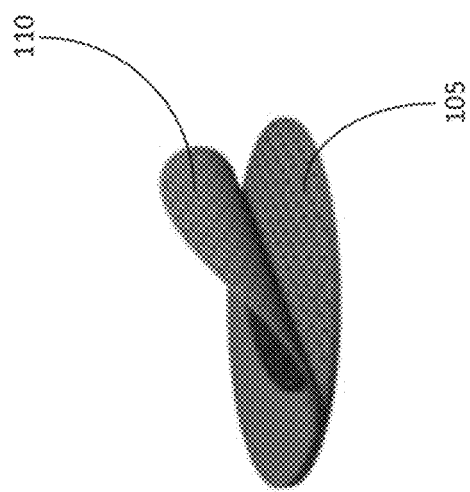
Figure 1D:
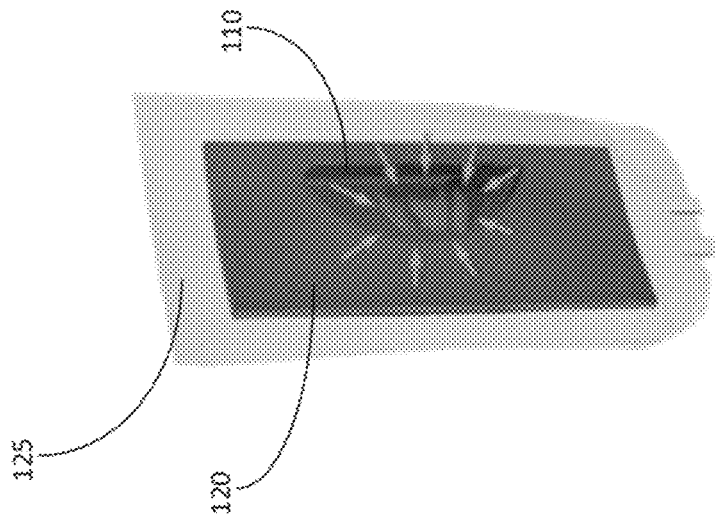
Figure 1C:
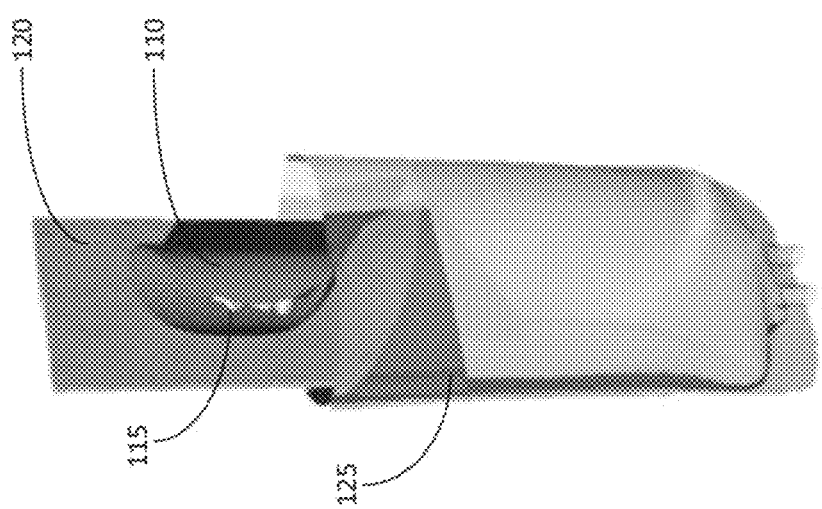

FIGS. 1A-1D show stages of construction of a general process for patterning a 3D object. As shown in FIG. 1A, a 2D master template 105 can be fabricated, for example, via conventional photolithography. The master template 105 can be used to mold a soft flexible template 110. A 3D object 115 can be wrapped in the flexible template 110, as shown in FIG. 1B. The 3D object 115 and the flexible template 110, along with a breather film 120, can be placed in the vacuum bag 125 as shown in FIG. 1C. The breather film 120 can be a thin porous media for distribution of vacuum within the bag 125. As shown in FIG. 1D, vacuum can be applied to remove air from the vacuum bag 125. The vacuum bag 125 containing the assembly can be placed inside an oven to emboss the pattern on the 3D object 115.

Figure 2:
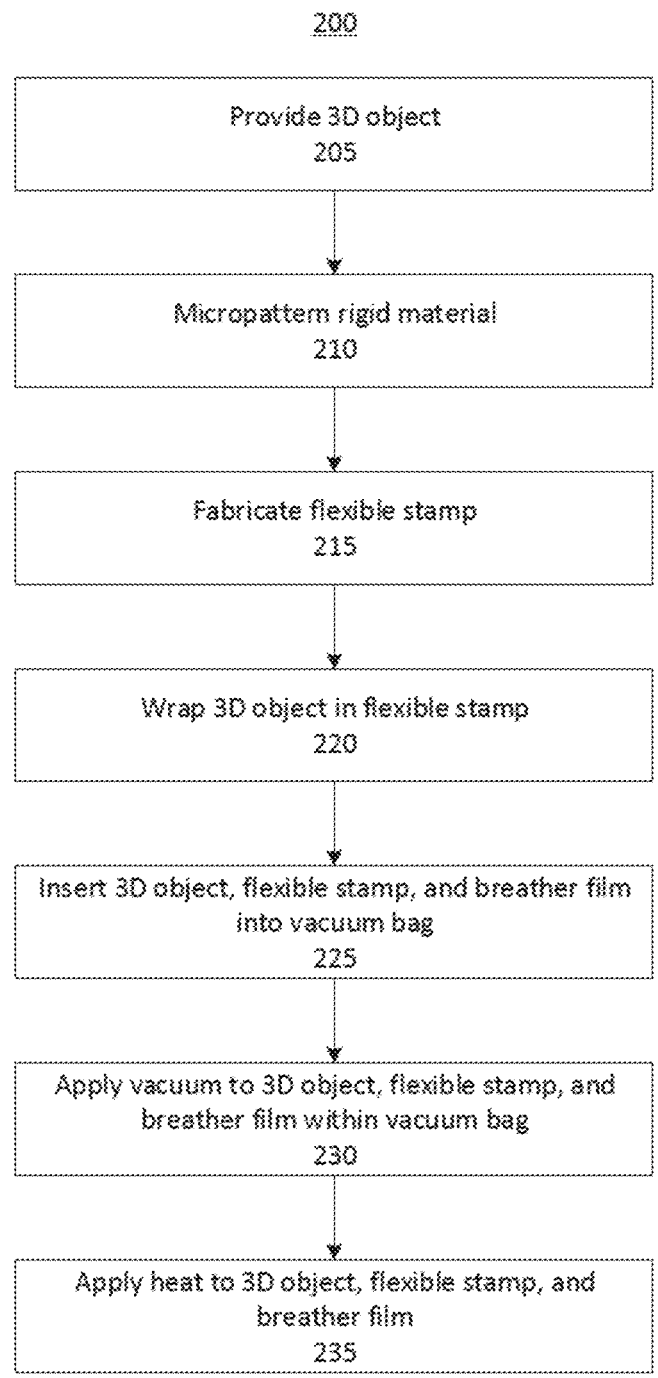
FIG. 2 illustrates a flowchart of a method for micropatterning a 3D object.

FIG. 2 illustrates a flowchart of a method 200 for micropatterning a 3D object. FIGS. 3A-3H show stages of construction of a micropatterned 3D object according to the method of FIG. 2. FIGS. 2 and 3A-3H are discussed together below.

Referring now to FIG. 2, the method 200 can include providing a 3D object (stage 205). The 3D object can be any type of object whose surface is to be patterned. In some implementations, the 3D object can have a complex shape. For example, the 3D object may have one or more surfaces having curves, folds, angles, creases, or other features. In some implementations, the 3D object can be a medical device, such as an implantable device. The 3D object can be formed, for example, from a biocompatible or hemocompatible material, such as silicone. The 3D object can be fabricated from a variety of materials using a variety of manufacturing techniques. In some implementations, 3D object can be printed using an additive manufacturing technique (e.g., 3D printing). For example, the 3D object can be printed using rigid materials such as VeroClear along with a 3D printer such as an Objet Connex 260 printer. After printing, the rigid material may also be boiled (e.g., in water for 90-150 minutes) and dried.

Figure 3A:
Figure 3B:
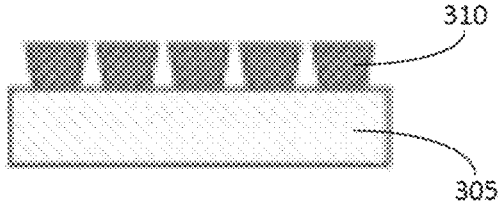

The method 200 includes micropatterning a rigid material (stage 210). In some implementations, the rigid material can be a material capable of being patterned via photolithography, such as silicon. For example, conventional photolithography on a hard substrate, such as a silicon wafer, can be performed. In some implementations, the rigid material can include a 4-inch silicon wafer. As shown in FIG. 3A, a silicon wafer 305 can be coated with a photoresist material 310. For example, the photoresist material 310 can be applied to the silicon wafer 305 via a spin coating process. In some implementations, the photoresist material 310 can be SU-8 2 or SU-8 2025. A lithographic process can be applied to pattern the photoresist material 310, as illustrated in FIG. 3B. For example, the photoresist material 310 can be selectively exposed to UV radiation according to the selected pattern. The pattern formed in the photoresist material 310 can be selected for its ability to enhance one or more surface characteristics of a 3D object to which the pattern is to be applied. For example, the pattern can be a pattern selected to improve an optical characteristic, a friction characteristic, an adhesion characteristic, a biocompatibility characteristic, or any other surface characteristic or combination of surface characteristics of the object. The pattern can include sidewalls and or channels that may be straight, curved, or angled. In some implementations, the pattern can be a regular repeating (e.g., periodic) pattern. The pattern can have a thickness of between 1 micron and 40 microns. For example, the pattern can have a thickness of 1 micron, 2 microns, 3 microns, 4, microns, 5 microns, 6 microns, 7 microns, 8 microns, 9 microns, 10 microns, 15 microns, 20 microns, 25 microns, 30 microns, 35 microns, 38 microns, 40 microns, 45 microns, 50 microns, 60 microns, 70 microns, 80 microns, 90 microns or 100 microns. In some implementations, the pattern can have a thickness of greater than 100 microns. In some implementations, the photoresist material 310 can be hard baked in a convection oven at a temperature in the range of 150 degrees C. to 250 degrees C. after it has been patterned. In some embodiments, the temperature can be 100 degrees C., 110 degrees C., 120 degrees C., 130 degrees C., 140 degrees C., 150 degrees C., 160 degrees C., 170 degrees C., 180 degrees C., 190 degrees C., 200 degrees C., 210 degrees C., 220 degrees C., 230 degrees C., 240 degrees C., 250 degrees C., 275 degrees C., 300 degrees C., 325 degrees C., 350 degrees C., 400 degrees C., 450 degrees C., 500 degrees C., or greater.

Figure 3C:
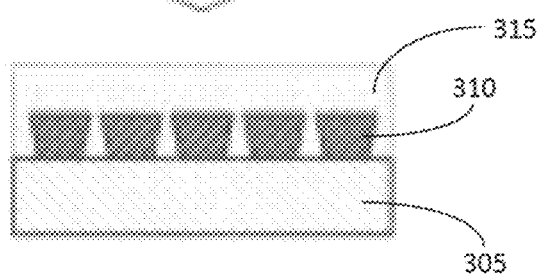
Figure 3D:
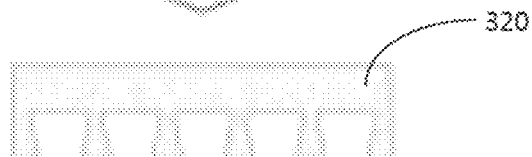

The method 200 can include fabricating a flexible stamp (stage 215). In some implementations, the rigid material micropatterned in stage 210 can serve as a master template, and can be used to create the flexible stamp. For example, the micropatterned rigid material can serve as a reusable master template that can be used to fabricate any number of flexible stamps. In some implementations, a flexible stamp can be molded using the master template. For example, as shown in FIG. 3C, an elastomeric material 315 can be coated over the photoresist material 310 and the silicon wafer 305, (e.g., via a spin coating process). In some implementations, the elastomeric material 315 can be a silicone material, PDMS, or any other flexible elastomeric material capable of being molded to take on the shape of the patterned photoresist material 310. For example, the elastomeric material can be ELASTOSIL® M4601. In some implementations, the elastomeric material 315 can be cured, for example by exposure to ultraviolet light, to solidify the elastomeric material 315. As shown in FIG. 3D, after curing, the solidified elastomeric material 315 can be peeled off of the photoresist material 310 and the silicon wafer 305, thereby forming the flexible stamp 320.

In some other implementations, a soft inversion of the hard master template (e.g., the silicon wafer 305 and the patterned photoresist material 310) can be formed. For example, the hard master template can be cast with silicone (e.g., Sylgard 184), which can be cured by exposure to heat (e.g., temperature in the range of 80 degrees C. to 120 degrees C.) for curing and then peeled off of the master template. In some implementations, such a silicone soft template can also be surface treated. For example, a self-assembled monolayer treatment can be applied (e.g., trichloro perfluoro silane) to a surface of the soft template to maximize the surface energy of the soft template. The silicone soft template can then be spin coated with the elastomeric material to form the flexible stamp 320.

In some implementations, the flexible stamp 320 can undergo a surface treatment process. For example, the flexible stamp 320 can be fluorinated, as shown in FIG. 3E. In some implementations, the surface treatment can include applying trichloro perfluoro silane to the flexible stamp 320. The surface treatment applied to the flexible stamp 320 can be selected to alter (e.g., decrease or increase) its adhesion to the 3D object to be patterned in a subsequent stage of the method 200. For example, in some implementations, the flexible stamp 320 can be functionalized via a self-assembled monolayer treatment to decrease its adhesion. In some implementations, a surface of the 3D object to be patterned also can undergo a surface treatment, such as a coating applied to at least a portion of its surface. For example, in some implementations the 3D object can be dipped into a material such as polyurethane or another polymer film to produce a thin polymer film on the surface of the 3D object. In some implementations, the material used to coat the 3D object can be selected to be biocompatible, for example to facilitate its use in medical devices such as implants for human subjects.

The method 200 can include wrapping the 3D object in the flexible stamp (stage 220) and inserting the 3D object wrapped in the flexible stamp into a vacuum bag, along with a breather film (stage 225). The results of this are illustrated in FIG. 3F. As shown, the 3D object 330 has been coated with a film 335 (e.g., a polymer film). The patterned side of the flexible stamp 320 is wrapped around the coated 3D object 330. The 3D object 330 wrapped in the flexible stamp 320 is place inside a vacuum bag 340. In some implementations, the vacuum bag 340 can be formed from a nylon material. In some implementations, the vacuum bag 340 can be assembled using a bagging film such as Stretchlon® 300 and 800, along with one or more sealant tapes, such as ACP composites.

As also depicted in FIG. 3F, the method 200 can include applying vacuum to the 3D object and the flexible stamp within the vacuum bag (stage 230). Although not depicted in FIG. 3F, in some implementations a breather film can also be positioned between at least a portion of the flexible stamp 320 and the vacuum bag 340 when vacuum is applied. For example, the breather film can be a porous, flexible material that can help to ensure even distribution of vacuum within the vacuum bag 340. In some implementations, the breather film can include Airtech's Airweave® material. One or more quick release vacuum connectors along with one or more vacuum pumps can be used to apply and control vacuum within the vacuum bag 340. As a result of applying vacuum within the vacuum bag 340, the greater air pressure outside the vacuum bag 340 causes the vacuum bag 340 to press inward against the flexible stamp 320, which in turn causes the patterned side of the flexible stamp 320 to be pressed against the coated surface of the 3D object 330.

Figure 3H:
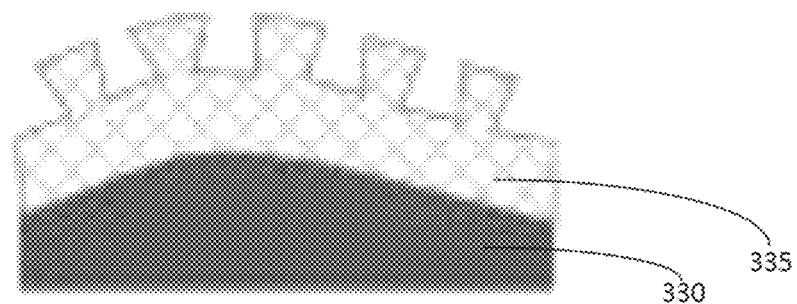

The method 200 can also include applying heat to the 3D object and the flexible stamp within the vacuum bag (stage 235). Heat can be applied while vacuum is also applied. In some implementations, heat can be applied by putting the vacuum bag 340 into an oven. As a result, the coating 335 applied to the surface of the 3D object 330 (or, in some implementations, the uncoated surface of the 3D object 330 itself) can soften, thereby allowing the pressure from the vacuum bag 340 to press the patterned side of the flexible stamp 320 into the coating 335 on the 3D object 330 via thermoplastic forming. This can also be referred to as hot embossing. In some implementations, the method 200 can include cooling the entire assembly, to allow the coating 335 to set with the pattern of the flexible stamp 320 imprinted on it. The 3D object 330 coated with the coating 335 and the flexible stamp 320 can then be removed from the vacuum bag 340, and the flexible stamp 320 can be peeled off. The result is the 3D object 330 coated with the coating 335 having a surface pattern corresponding to the pattern of the flexible stamp 320, as illustrated in FIG. 3H. It should also be understood that, in some implementations, the pattern can be formed directly into the surface of the 3D object 330 itself, rather than into the coating 335 that has been applied to the 3D object 330.

In general, the method 200 can be used to micropattern a variety of types of 3D objects, and many variations (e.g., types of materials, surface treatments, etc.) can be used in connection with the method 200. For example, results of the method 200 were confirmed experimentally for several different objects and micropatterns, as described further below. In particular, using variations of the method 200, micropatterns inspired by tree frogs (e.g., periodic hexagonal micropatterns) and shark skin riblets were applied to objects including a 3D printed chess piece, a Foley catheter, a nitinol guidewire, and a star-shaped gripper.

The chess piece was 3D printed in VeroClear material using an Objet Connex 260 printer, boiled in water for 2 hours dried, and dip-coated in polyurethane (e.g., 13 wt % Tecoflex SG-60D in Dimethylacetamide (DMAC), cured overnight at 80° C.). Sufficient adhesion was observed between the 3D printed part (e.g., the VeroClear material) and Tecoflex such that no delamination was observed at any stage of vacuum bagging or subsequently. The 20 Fr silicone Foley catheter (provided by Bard Medical) was plasma treated (e.g., air plasma). The catheter was also soaked in 12 vol % 3-glycidoxypropyltrimethoxysilane in ethanol for two hours, and dip-coated with Tecoflex. In some implementations, this treatment can create a surface monolayer on silicone that facilitates covalent bonding with polyurethane for enhanced adhesion. A nitinol guidewire having a 380 micron diameter with a light oxide finish and annealed straight (provided by Fort Wayne Metals) was heat treated to form the curved structure (e.g., wrapped around a mandrel at 500° C. for 5 minutes and then quenched). No additional adhesion promoter was used, and no delamination was observed after vacuum bagging. The star-shaped gripper was cast from silicone (e.g., Ecoflex 00-30) and nylon mesh. The gripper molds were 3D printed from VeroClear material using an Objet Connex 260 printer. The molds were boiled in water for two hours and cooled to reduce effects of surface cure inhibition. Subsequently, the top part and bottom part of the gripper were cast in silicone (e.g., Ecoflex 00-30). The parts were cured at room temperature for 1 hour. Fresh silicone (e.g., Ecoflex 00-30) was mixed and applied to the surfaces, and nylon fabric was sandwiched between the parts.

Thus, various grades of Chronoflex and Tecoflex with different mechanical properties were prepared for use with the method 200, to illustrate the versatility of the method 200 and to accommodate the varying mechanical properties of the objects coated with these materials. In some implementations, coating different objects with polyurethane can be achieved by dip coating the objects in solutions of polyurethane dissolved in DMAC. A ChronoFlex/DMAC solution can be provided by the manufacturer and diluted 50%, by volume, in DMAC before dipping. Tecoflex can be provided by the manufacturer in the form of pellets, which can be dissolved in DMAC with different ratios. In some implementations, the ratios can be selected such that relatively high concentrations of polyurethane could be achieved. Polyurethanes for use in the method 200 can be mixed using a planetary/centrifugal mixer (e.g., a Thinky SR-500 mixer) for 60 minutes at 2200 rpm.

Figure 4:
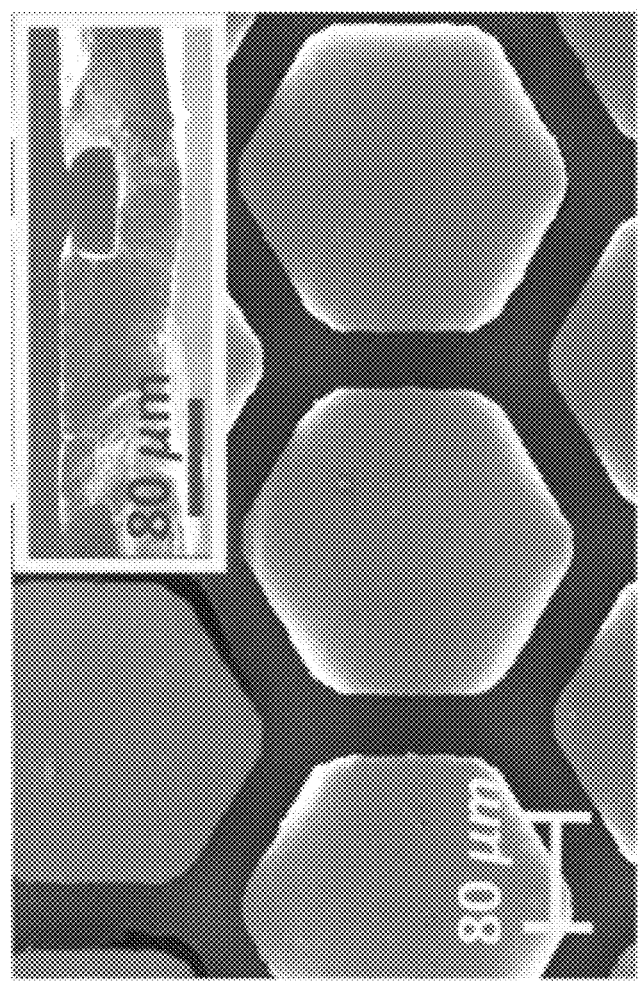
FIG. 4 shows a magnified view of a hexagonal micropattern that can be formed on the surface of a 3D object using the method of FIG. 2.
Figure 5:
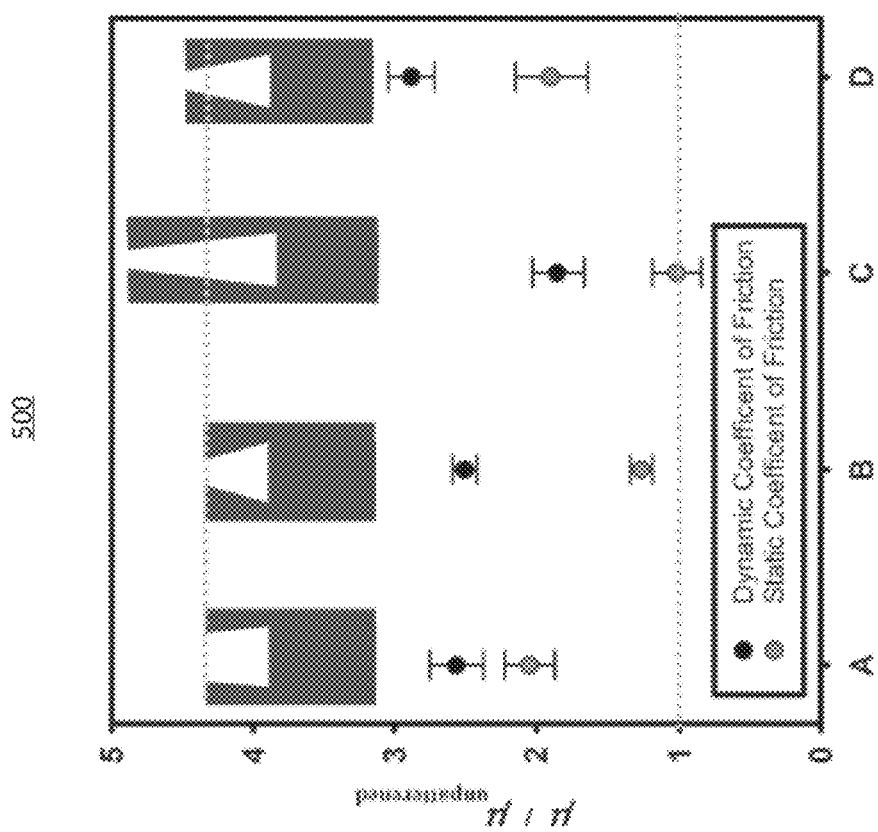
FIG. 5 is a graph showing coefficients of friction for each of four variations of the hexagonal pattern shown in FIG. 4.

FIG. 4 shows a magnified view 400 of a hexagonal micropattern that can be formed on the surface of a 3D object using the method 200 of FIG. 2. The micropattern shown in FIG. 4 is inspired by tree frogs, and can be used to enhance wet adhesion. In some implementations, this pattern can be applied to medical devices (e.g., vascular devices) to help them remain in place inside a subject. FIG. 5 is a graph 500 showing coefficients of friction for each of four variations of the hexagonal pattern shown in FIG. 4, labeled A-D in FIG. 5. Design parameters and other characteristics for each of these variations are provided in Table 1 below:

TABLE 1

| Pattern Type | Depth (μm) | Periodicity (μm) | Channel Width (μm) | Exposure Time (mj/cm$^{-2}$) | Photoresist |
|---|---|---|---|---|---|
| A | 3.6 | 300 | 30 ± 2 | 4 × 5 | SU8 2 |
| B | 3.6 | 300 | 28 ± 2 | 8 × 5 | SU8 2 |
| D | 5.5 | 300 | 34 ± 2 | 7 × 5 | SU8 2025 |
| D | 36 | 300 | 37 ± 2 | 10 × 5 | SU8 2025 |

In Table 1, the values are based on 2D templates that were used for transferring patterns. Depths are measured using a profilometer and optical microscopes. Periodicity is measured along the [110] direction using optical microscopy. Channel width is defined and measured on the top side of the patterns using optical microscopes.

By controlling the thickness, exposure, and development conditions of the 2D template, micro patterned films with the same lattice, but different feature heights and widths (e.g., those of patterns labeled A, B, C, and D in FIG. 5) were fabricated. For all films, some degree of feature undercut was obtained, which may improve wet friction. Films A and B had the same height, but film B had features with smaller channel width (e.g., due to a longer exposure time). Films C and D had film thicknesses greater than A and B. Thus, comparing patterns A and B shows the significance of the in-plane-geometry of the channels and comparing B and C shows the significance of feature height. Wet dynamic and static coefficients of friction for each film were normalized to those of un-patterned films. The comparison presented in FIG. 5 shows enhancement in coefficients of friction up to three times that of un-patterned films. Comparison of films shows that channel depth can affect wet friction. The overall enhancement of wet friction associated with these tree frog inspired micropatterns can make them useful for micropatterning of nonplanar medical devices due to the frequent requirement to adhere to or anchor against tissue in a wet environment.

Figure 6:
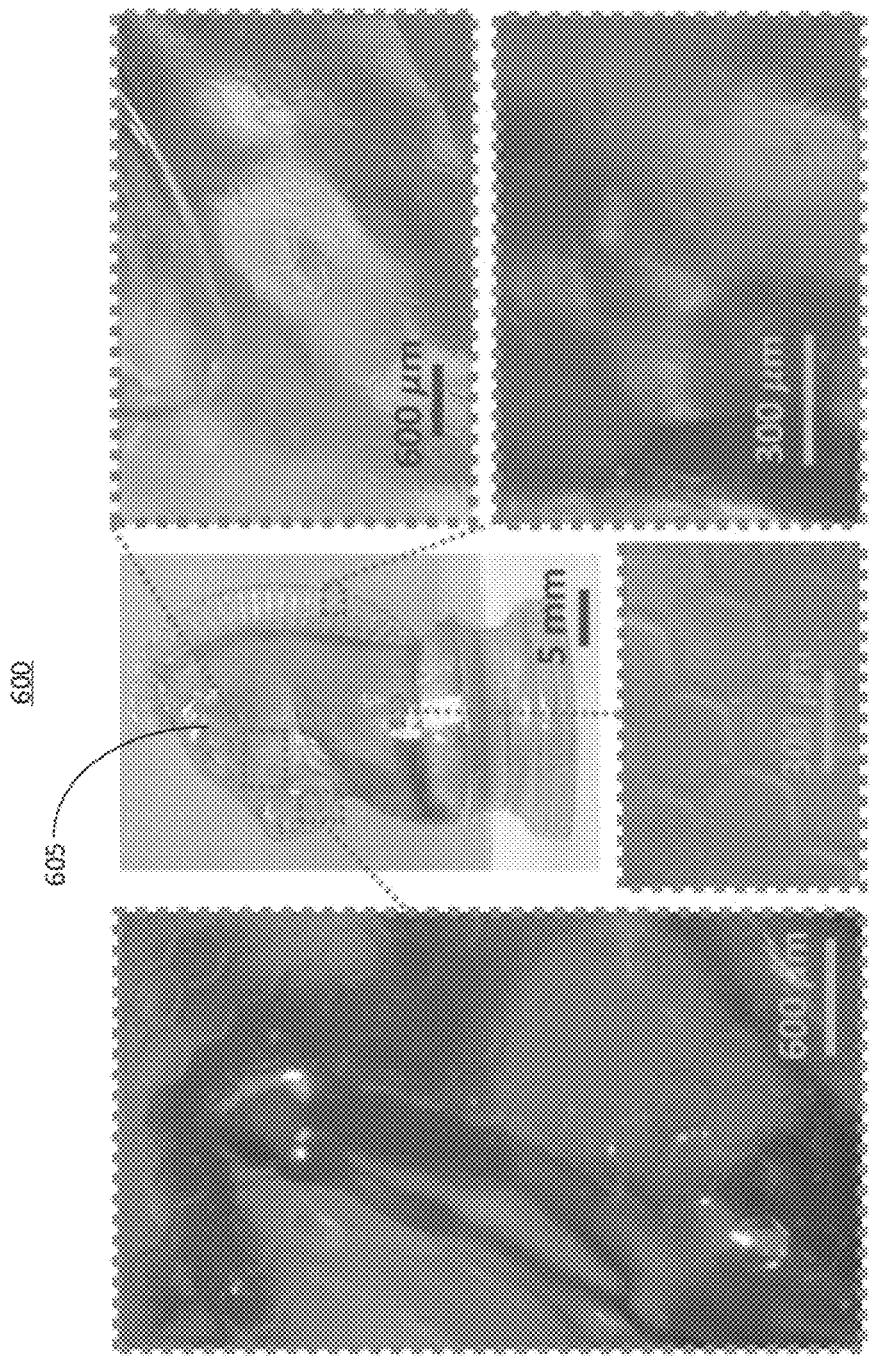
FIG. 6 illustrates a hexaganoal micropattern applied to a 3D printed chess piece under different magnifications.

FIG. 6 illustrates various views 600 showing different magnifications of a hexaganoal micropattern applied to a 3D printed chess piece 605. FIG. 6 shows the versatility of the method 200, which was used to transfer the hexagonal pattern to the chess piece 605. For example, despite the complicated geometry of the chess piece 605, the pattern was transferred over the area of the object even in the dimples, creases, and folds of the object. It should be noted that additive manufacturing is useful for fabrication of nonplanar objects with arbitrary and complex shape, such as the chess piece 605. However, the ability to produce fine micro-scale features via additive manufacturing is limited. The features of the micropattern illustrated in FIG. 6 are thinner (e.g., about 30 μm) than those that can typically be resolved by 3D printers, and micropatterns with far smaller features can easily be formed by the method 200. For example, feature sizes may be less than about 20 microns, less than about 10 microns, or less than about 5 microns. In some implementations, feature sizes of around 3 microns may be obtained using the method 200. Thus, by utilizing 3D printing (e.g., to manufacture an object to be patterned, such as the chess piece 605) in concert with the micropatterning technique of the method 200, tremendous design freedom exists. Accordingly, using the method 200 can allow for a combination of the advantages of additive manufacturing for rapid prototyping of complicated surfaces with the advantages of lithography for micro-scale features.

In some implementations, the sharpness of the patterns may be reduced where the radius of curvature of the 3D object being patterned is very small, as illustrated in FIG. 6. This effect can be understood based upon the kinematics of the deformation of the flexible stamps, with a thickness of (t) bending along a surface with a small radius of curvature (r). Assuming the neutral plane occurs in the mid-plane of the stamp, the kinematic relationship in the theory of plates dictates that e1=t/2r. Where e1 is the normal in-plane strain on the surface of the stamp in contact with the object. A large in-plane strain can result in a large normal strain in the stamp, perpendicular to the stamp surface, e3=−n e1, where n is the poisons ratio, ~0.5 for silicones. As a result, there is a reduction of the depth of pattern at curved areas is proportional to t/r. In the example of FIG. 6, t can be approximately 200 microns, which can explain why in the areas that the radius of curvature is on the same order, a reduction in pattern sharpness can be observed. Furthermore, this suggests that that micropatterning on larger curvature surfaces may benefit from thinner stamps. However, it should be understood that the thickness of a flexible stamp can be greater than or less than 200 microns. For example, a flexible stamp can have a thickness of less than 20 microns, less than 30 microns, less than 40 microns, less than 50 microns, less than 60 microns, less than 70 microns, less than 80 microns, less than 90 microns, less than 100 microns, less than 150 microns, less than 175 microns, less than 200 microns, less than 225 microns, less than 250 microns, less than 275 microns, less than 300 microns, less than 350 microns, less than 400 microns, less than 450 microns, or less than 500 microns. In some implementations, a flexible stamp can have a thickness of greater than 500 microns.

Figure 7:
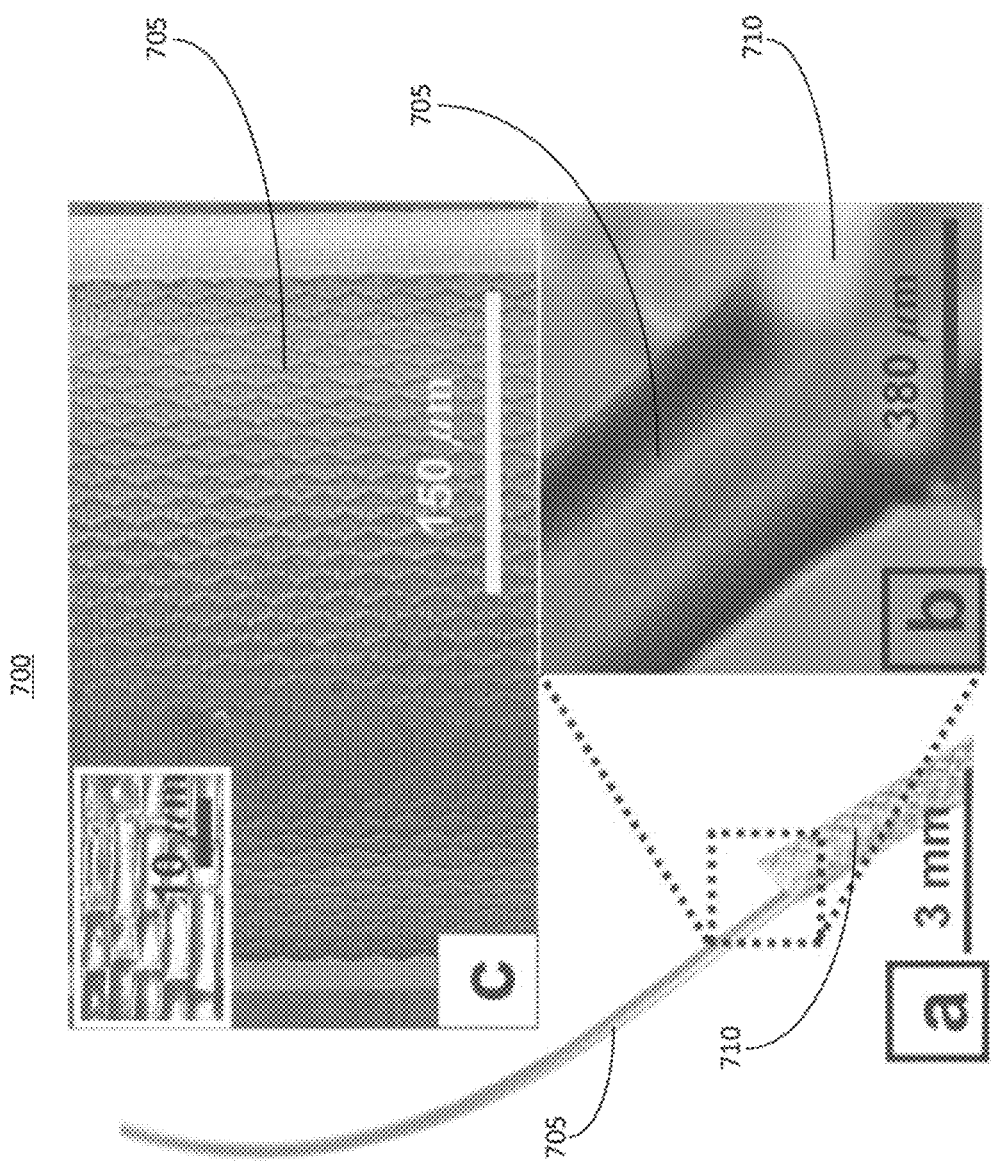
FIG. 7 illustrates various views of a micropattern applied to a high aspect ratio wire.

FIG. 7 illustrates various views of a micropattern applied to a high aspect ratio wire 705. Nitinol frames, stents and guidewires can provide structural elements associated with a wide variety of medical devices. Thus, FIG. 7 illustrates the ability of the method 200 to produce high quality micropatterning of such small, high aspect ratio elements. In the example of FIG. 7, the wire 705 was formed and annealed in a curved shape. FIG. 7 shows the wire 705 protruding from a lumen 710 and micropatterned with a pattern inspired by shark skin riblets, which can help to reduce fluid shear forces. The wire 705 was coated with polyurethane (e.g., TecoFlex MG-8020, having a high flexural modulus of about 165,000 psi) to demonstrate the ability of the method 200 to apply a micropattern to stiffer materials. Unlike alternative methods, where wires or sheets of nitinol are patterned prior to forming, patterns can be imparted after annealing the nitinol in the desired shape due to the versatility of the method 200. In some implementations, this versatility can be a requirement to apply surface micropatterns to existing nitinol devices. Polyurethanes, similar to those used in this example, may enhance the thrombogenicity of nitinol when used as a passivation layer. Moreover, the shark-skin inspired riblets of the micropattern shown in FIG. 7 are known for reduction of drag forces and fluid shear stresses.

Figure 8:
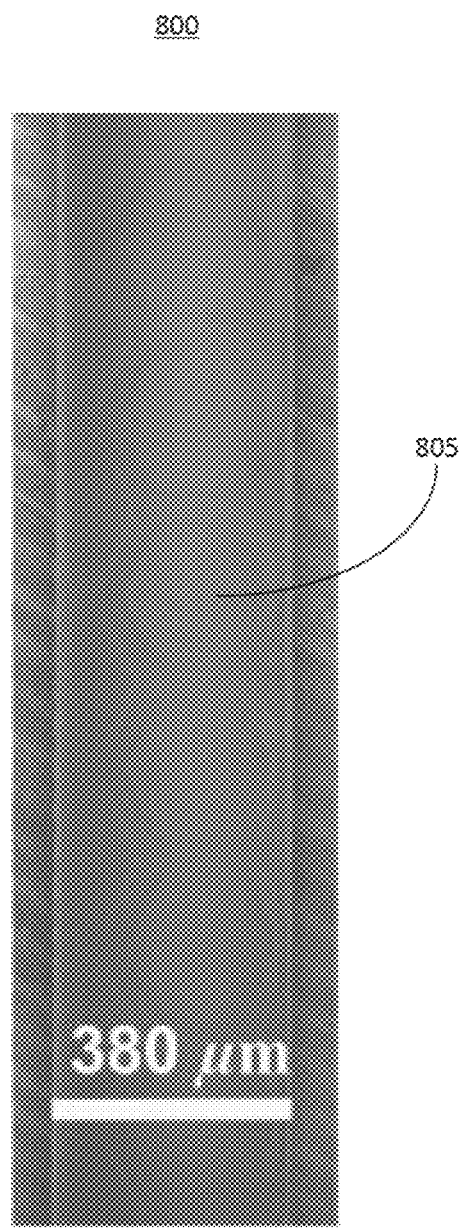
FIG. 8 illustrates a view of a micropattern applied to a high aspect ratio wire.

FIG. 8 illustrates a view 800 of a micropattern applied to a high aspect ratio wire 805. The wire 805 is similar to the wire 705 of FIG. 7. However the micropattern applied to the wire 805 is a hexagonal pattern inspired by tree frogs. In some implementations, such a pattern can help to enhance anchoring of stents or other implantable devices against tissue structures. The wire 805 was patterned according to the method 200, described above in connection with FIG. 2. As shown, the pattern is reliably transferred to the wire 805 via the method 200. In some implementations, the pattern shown in FIG. 8 can be used to engineer characteristics such as thrombogenicity, hemodynamics, and friction/adhesion. Accordingly, the method 200 can provide a new route for engineering of these properties in existing nitinol stents, devices, and other implants.

Figure 9A:
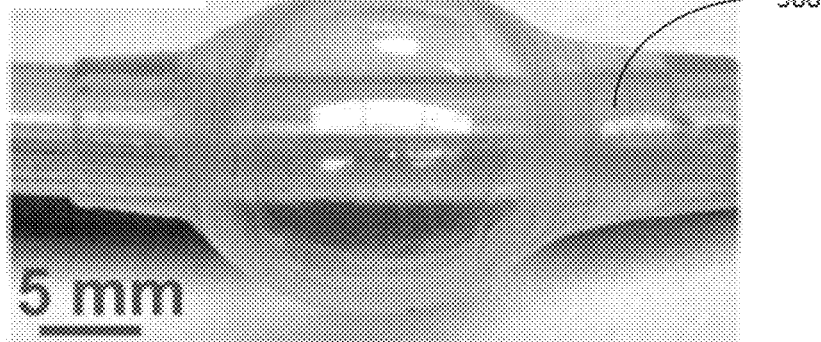
FIGS. 9A-9C show various views of a micropatterned Foley catheter.
Figure 9B:
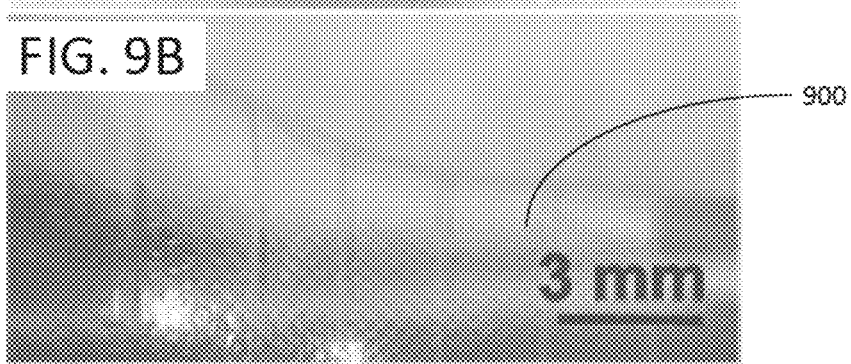
Figure 9C:
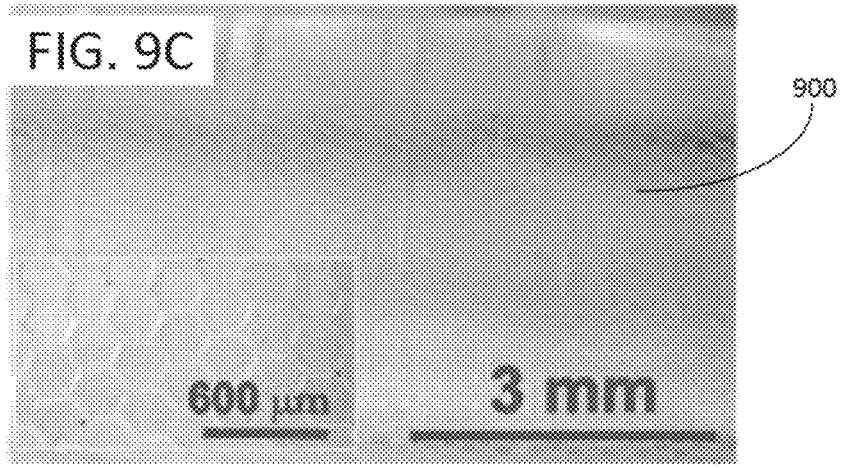

FIGS. 9A-9C show various views of a micropatterned Foley catheter 900. The Foley catheter 900 is typically used to drain urine from the bladder. FIGS. 9A-9C show the Foley catheter 900 in at various degrees of magnification as labeled in the figures, as well as in both an inflated state (e.g., FIGS. 9A and 9B) and an uninflated state (FIG. 9C). A hexagonal micropattern inspired by tree frogs was applied to the Foley catheter 900 using the method 200 of FIG. 2. In some implementations, this pattern can help to increase wet friction on the balloon, to enhance anchoring the catheter 900 in the bladder. Furthermore, this example illustrates the compatibility of the method 200 with soft materials. In this example, a highly extensible polyurethane (Tecoflex-SG80A with ultimate elongation of about 660%) is used to match the elastic properties of silicone. Due to the highly extensible nature of the micro-patterned polyurethane films, the catheter 900 remains highly stretchable and functional upon inflation (see FIG. 9A), with the micropattern intact (see FIG. 9B). Upon deflation, the catheter retains its original cylindrical shape (see FIG. 9C), with the patterns still clearly visible. In some implementations, micropatterning of the entire balloon area of the catheter 900 can be achieved in a single step (e.g., a single instance of the method 200), making it cost effective and scalable for enhancement of existing medical devices.

Figure 10:
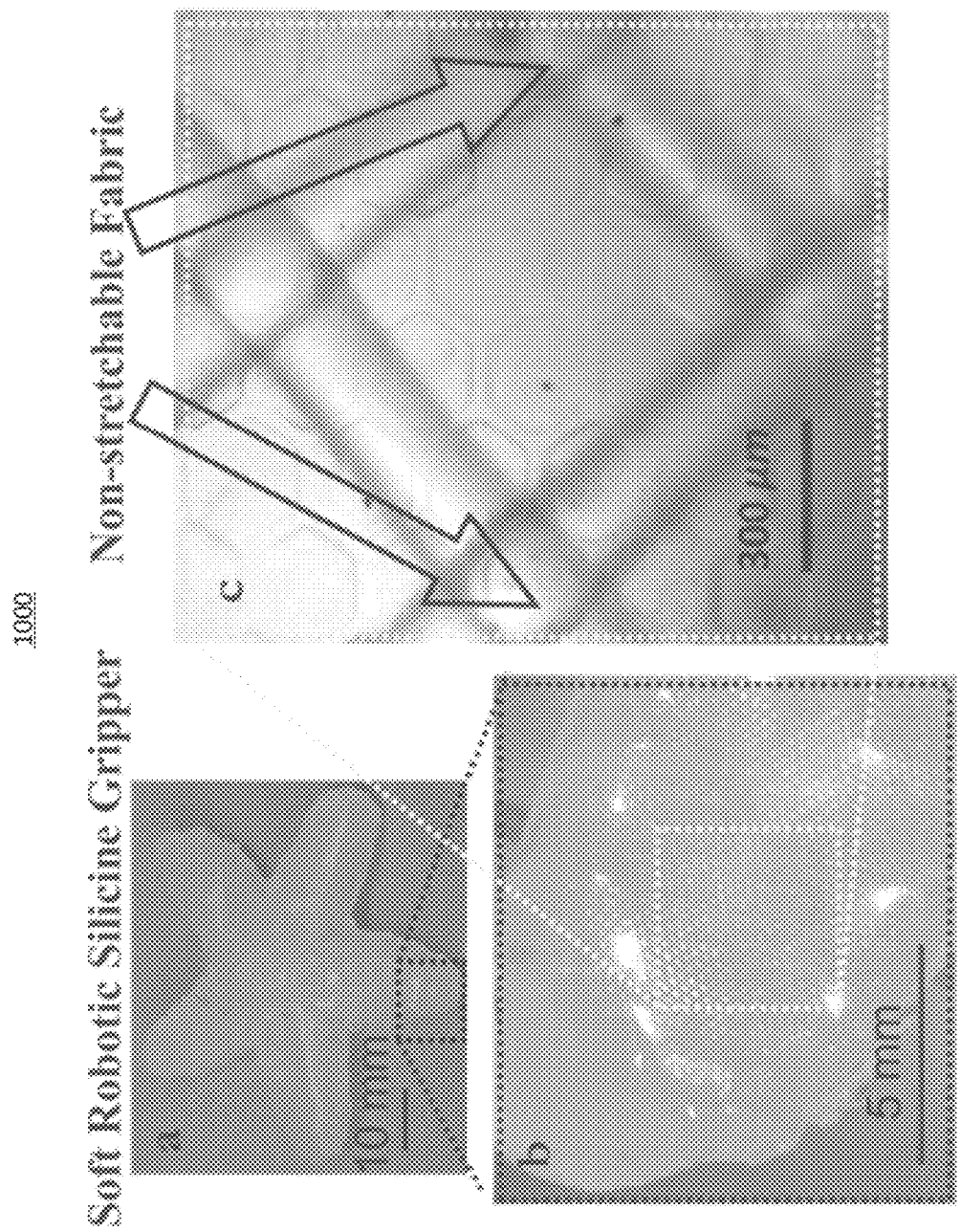
FIG. 10 shows various views of a micropatterned inflatable star-shaped gripper made from silicone.

In some implementations, fields such as soft robotics can employ the cost-effective techniques of 3D printing and silicone molding for fabrication of grippers, end effectors, and more complex machines. While complicated geometries for grippers can be fabricated rapidly, they lack surface micro-features that could enhance their functionality. For this reason and the concepts discussed previously, the method 200 can be well suited to enhance the properties of such devices. FIG. 10 shows various views 1000 of a micropatterned inflatable star-shaped gripper made from silicone. In this example, the tree frog inspired hexagonal pattern was used, which can enhance the gripper's functionality, for example, by increasing friction. In some implementations, such a pattern can be useful for applications in which the gripper holds wet objects. It should also be understood that other features such as Gecko inspired patterns could be incorporated for improving dry frictional properties, and could be applied to the surface of the gripper (or other 3D object) using the method 200.

In order to estimate the expected change in the periodicity of patterns applied using the method 200, images of the micropatterned star shape gripper and wires were analyzed. Variations of between approximately 3% and 9% were observed. These changes are mainly due to handling, stamp mechanics, and the process of thermoplastic embossing. In order to further elucidate the fidelity of the patterns transferred via the method 200, beyond the fundamental limits, the tree frog inspired hexagonal patterns (i.e., Pattern C in Table 1 above) was transferred from 2D templates to flat silicon wafers coated with polyurethane (MG-8020). The depth, periodicity, and width of the patterns were characterized using a profilometer (Bruker, Dektak-XT) and optical microscopy. The comparison between the patterns transferred showed less than a 10% reduction in the depth of the pattern (e.g., 5.5 to 5 microns), less than 4% change in periodicity along random directions, and no more than 5% change in the width of the patterns.

Thus, the techniques described herein, such as the method 200, represent cost-effective techniques for micro-patterning arbitrary 3D objects, with an emphasis on medical applications. These techniques combines several technologies, including photolithography, soft lithography, and vacuum bagging. In some implementations, these techniques can be integrated with current 3D printing technologies for rapid prototyping of different devices, and can be scalable for medium or large batch production. Furthermore, because these techniques can be used to pattern objects of arbitrary geometry, they can be used to modify or enhance the properties of many existing objects and devices.

Figure 11A:
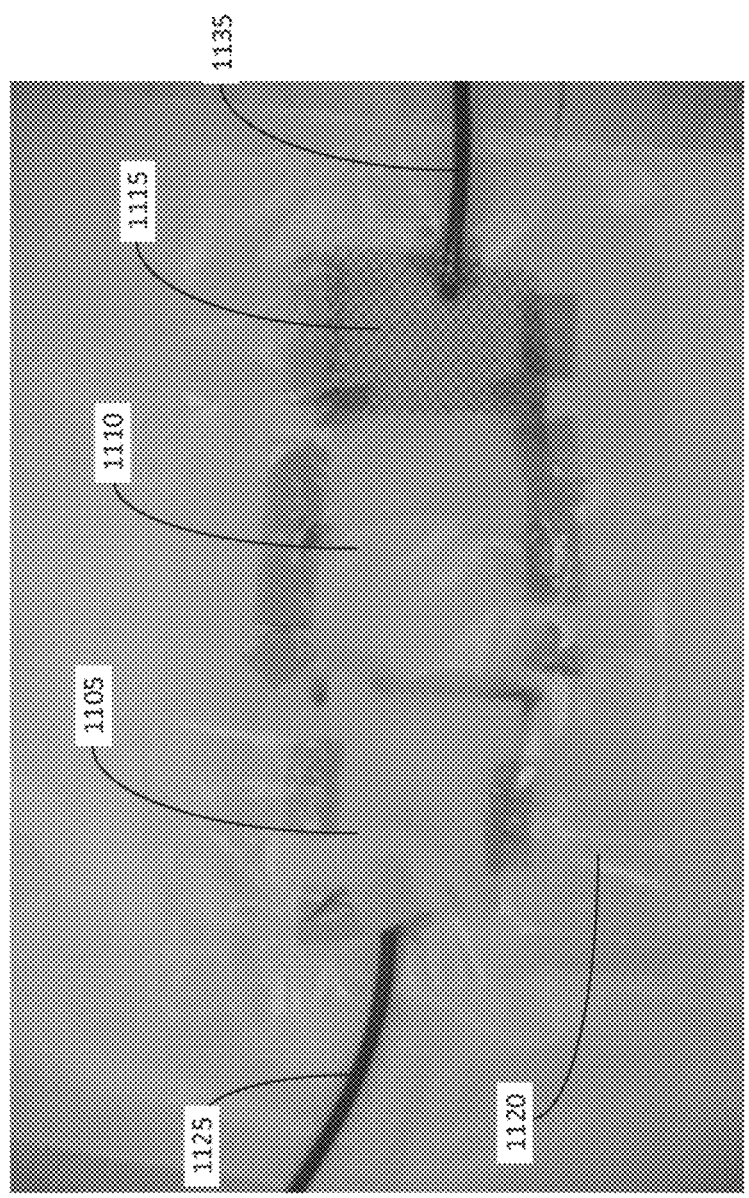
FIGS. 11A-11C show stages of a process for resin infusion on a 3D object.
Figure 11B:
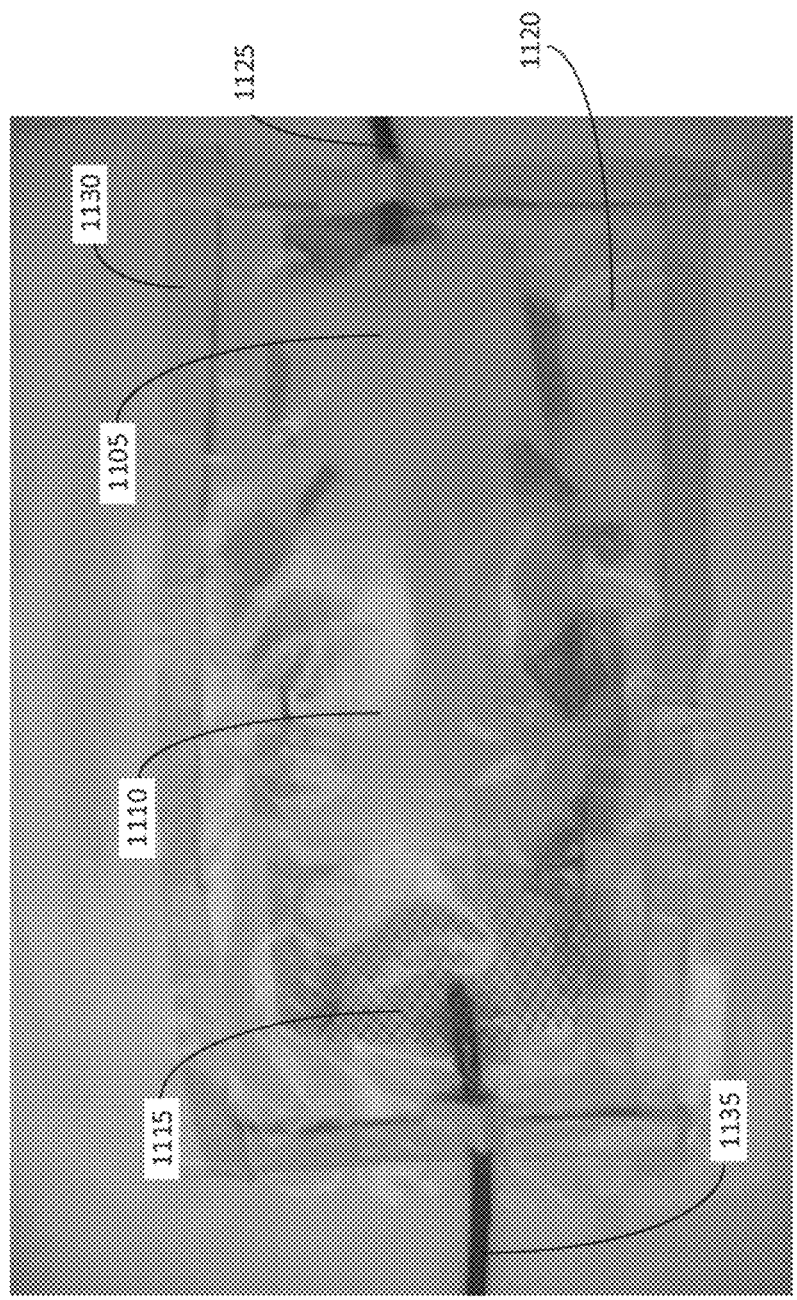
Figure 11C:
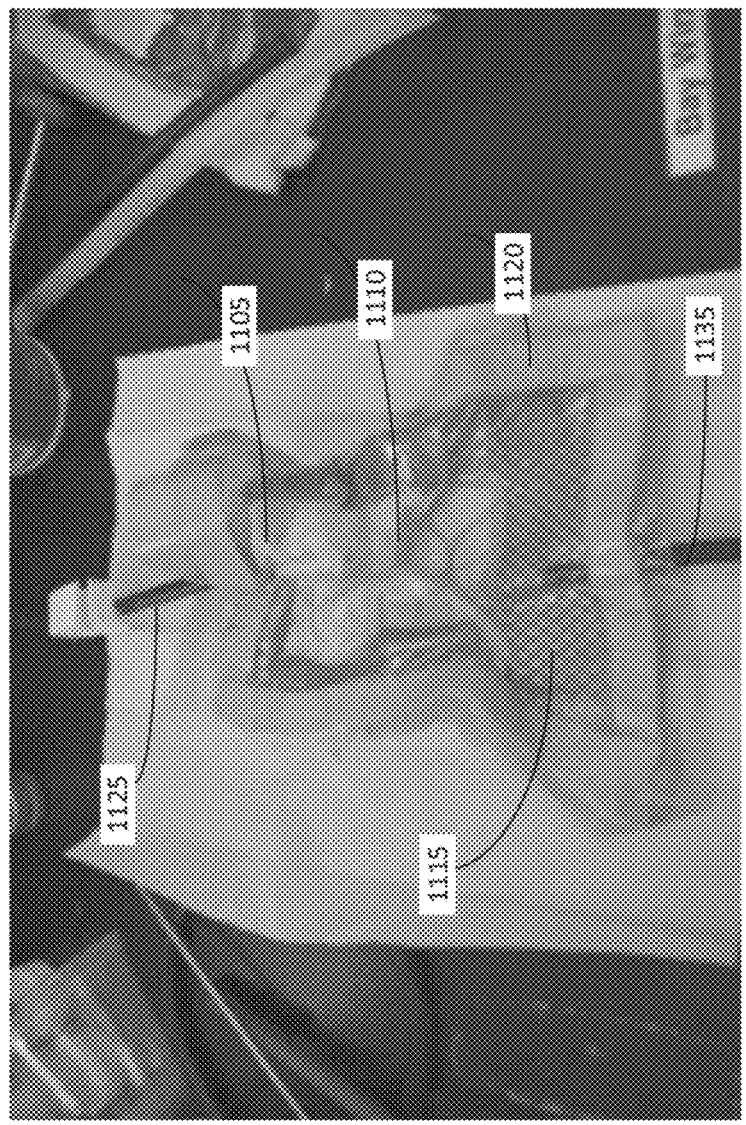

FIGS. 11A-11C show stages of a process for resin infusion on a 3D object. As illustrate in FIG. 11A, breathers 1105 are positioned to overlap with fabric 1110 (e.g., Kevlar) and a resin infusion mesh 1115. The fabric 1110 is laminated on a 3D object and then sealed in a vacuum bagging film 1120.

As shown in FIG. 11B, vacuum sealing tape 1130 can be used to seal the vacuum bagging film 1120. A tube 1125 is connected to the breathers 1105. Another tube 1135 is connected to the resin infusion mesh 1115. Each of the tubes 1125 and 1130 can be opened and shut off using hose clamps.

First, the vacuum bag is vacuumed via the tube 1125 while the resin infusion tube 1135 is closed, as shown in FIG. 11C. In some implementations, thermoset biopolymer can be mixed and degassed, and then the resin infusion tube 1135 can be placed in the resin infusion mesh 1115 and a hose clamp can be opened. Consequently, resin can be infused in the vacuum bag 1120 through the vacuumed pores of the fabric 1110. Upon completion of infusion in the fabric 1110, both tubes 1125 and 1135 can be shut off and the vacuum bag 1120 can be placed in an oven for curing. Finally, the fabric 1110 and the resin infusion mesh 1115 can be cured with the shape of the 3D object on which they were laminated.

Figure 12A:
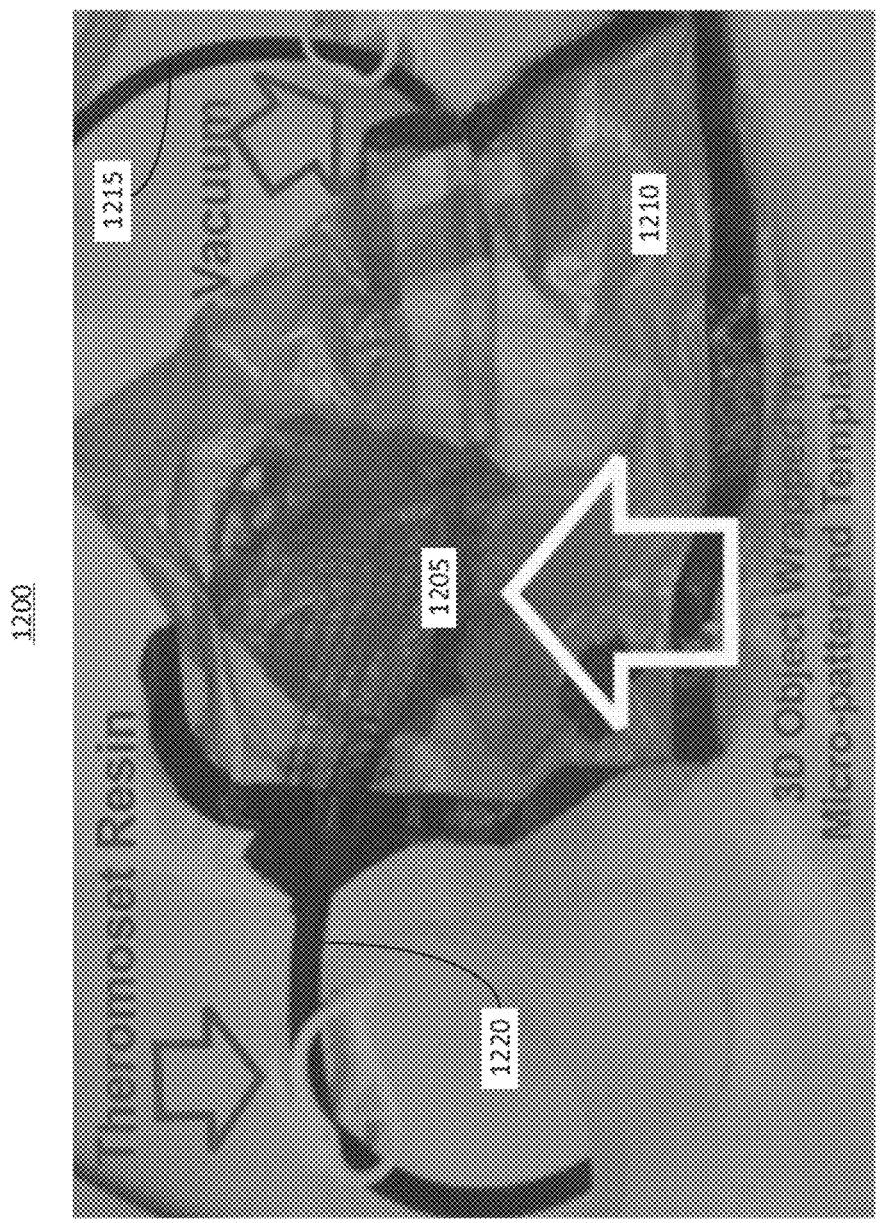
FIGS. 12A and 12B illustrates a setup that can be used for resin infusion and micropatterning of a 3D object formed from PDMS.
Figure 12B:
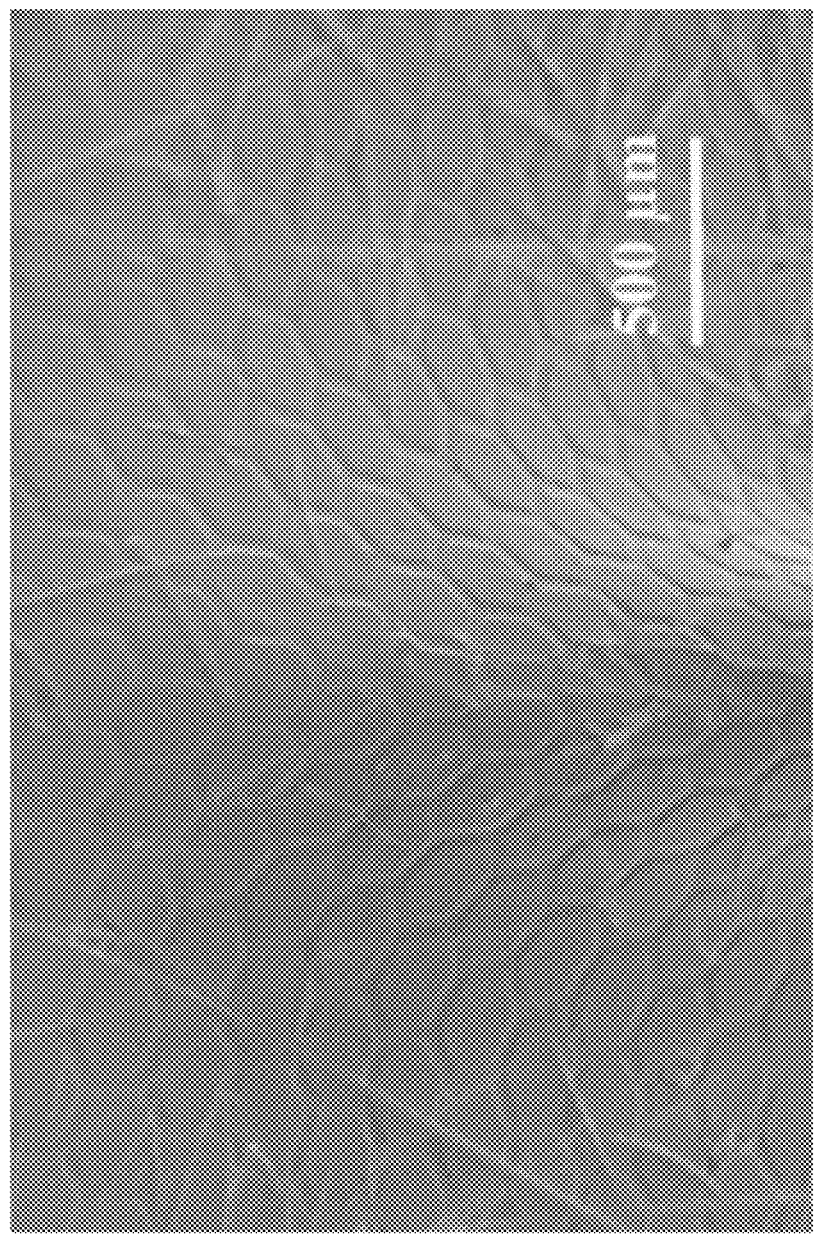

FIG. 12A illustrates a setup 1200 that can be used for resin infusion and micropatterning of a 3D object formed from PDMS. The setup 1200 combines the principles of the method 200 for imprinting a micropattern on a 3D object, along with principles of the resin infusion process of FIGS. 11A-11C. In the setup 1200, ultrathin glass tissue is laminated onto an object formed from PDMS, and a micropatterned template (e.g., a flexible stamp as described above in connection with the method 200) is wrapped around the PDMS object. The glass tissue can be a porous film made from glass fibers. In some implementations, the PDMS object and the glass tissue can be plasma treated to result in formation of covalent bonds after curing the resin. The PDMS object wrapped in the flexible stamp (labeled 1205 in FIG. 12A) is inserted into a vacuum bag 1210. Vacuum is applied within the vacuum bag 1210 via a tube 1215, and resin is infused into the vacuum bag 1210 via a tube 1220 in a manner similar to that described above in connection with FIGS. 11A-11C. As a result, resins are passed through pores in the flexible stamp and the glass tissue, thereby forming a pattern 1250 on the surface of the PDMS object as shown in FIG. 12B. In this example, the pattern 1250 is the tree from inspired hexagonal pattern, however any arbitrary pattern can be applied using this technique.

Figure 13A:
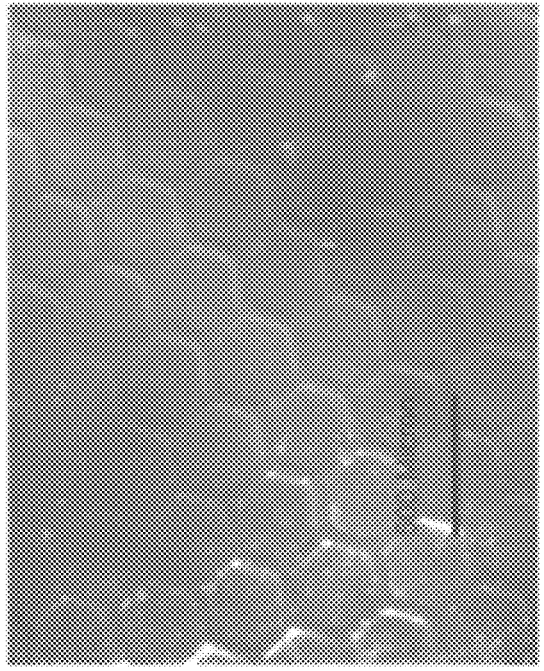
FIGS. 13A and 13B show a comparison between micropatterns formed via 3D printing and conformal template vacuum bagging.
Figure 13B:
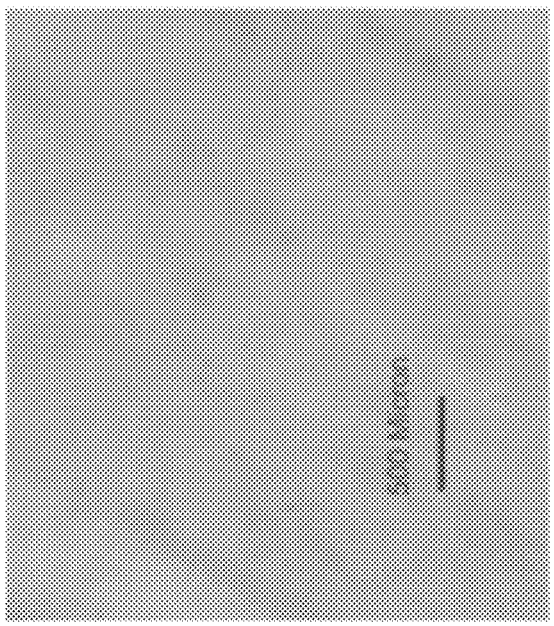

FIGS. 13A and 13B show a comparison between micropatterns formed via 3D printing and conformal template vacuum bagging. FIG. 13A illustrates a magnified image of a 3D printed part 1305. The 3D printed part 1305 was fabricated using a CAD file that included a hexagonal pattern having hexagons of approximately 500 microns in width on its surface. However, as shown, despite the inclusion of the pattern in the file used to print the part 1305, the surface of the part 1305 does not exhibit any observable hexagon pattern. This can be due to limitations in the resolution of typical 3D printing devices, for example. In contrast, FIG. 13B shows a part 1310 that was patterned according to the conformal template vacuum bagging technique described in connection with the method 200 of FIG. 2. The flexible stamp used to fabricate the part 1310 had a pattern having hexagons of approximately 500 microns in width, similar to the pattern that was incorporated into the file used to fabricate the part 1305. However, the pattern is more reliably transferred and is easily visible on the part 1310, due to the superiority of the vacuum bagging technique as compared to 3D printing.

Figure 14:
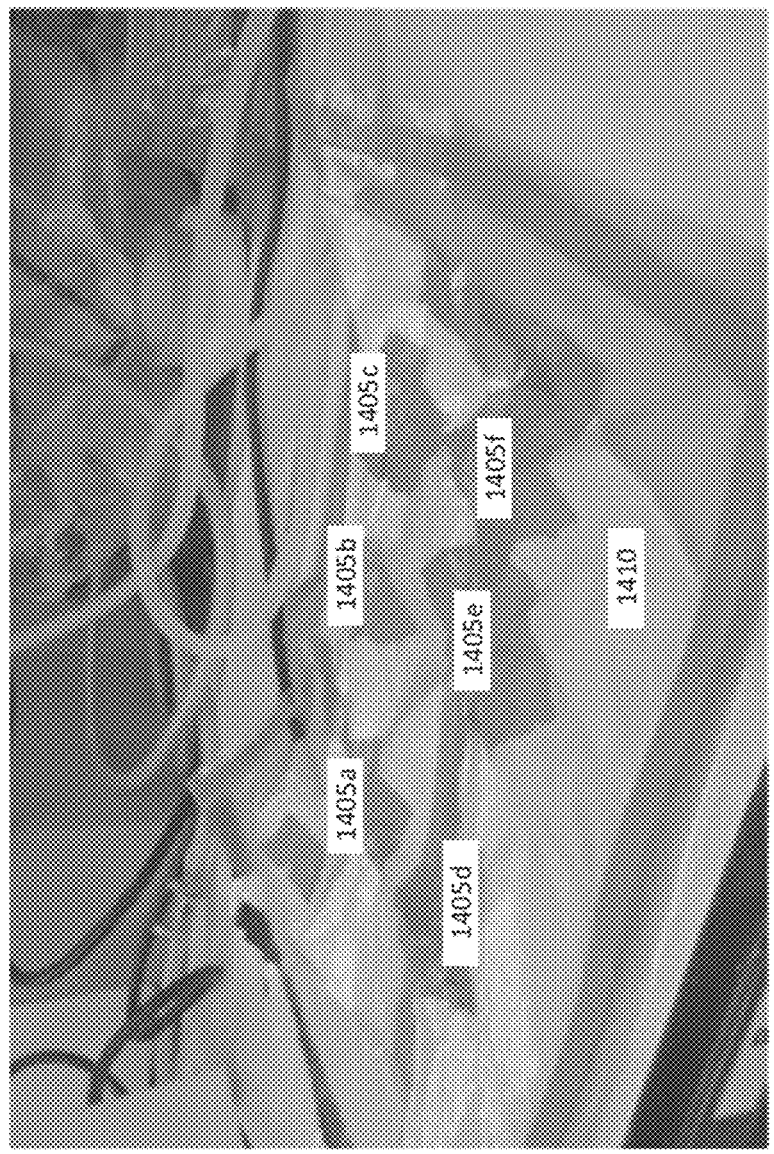
FIG. 14 shows a setup demonstrating the scalability of vacuum bagging for patterning 3D objects.

FIG. 14 illustrates a setup 1400 demonstrating the scalability of vacuum bagging for patterning 3D objects. The setup 1400 and its principles of operation are similar to that described above in connection with the method 200 of FIG. 2. However, six micropatterned templates each wrapped around a respective 3D object (labeled 1405a-1405f in FIG. 14) are place inside a single vacuum bag 1410. Vacuum can be applied to the objects 1405a-1405f simultaneously, and the entire assembly can be put into an oven at once. In some implementations, any arbitrary number of 3D objects wrapped in a respective template could be inserted into a single vacuum bag similar to the vacuum bat 1410. Thus, the setup 1400 demonstrates that the method 200 can be scalable for patterning multiple objects simultaneously. It should also be understood that the objects 1405a-1405f need not have the same shape as one another, and that the patterns applied to each need not be the same, as the principles of operation are not dependent on the particular geometry of the objects or the patterns of the templates.

Figure 15:
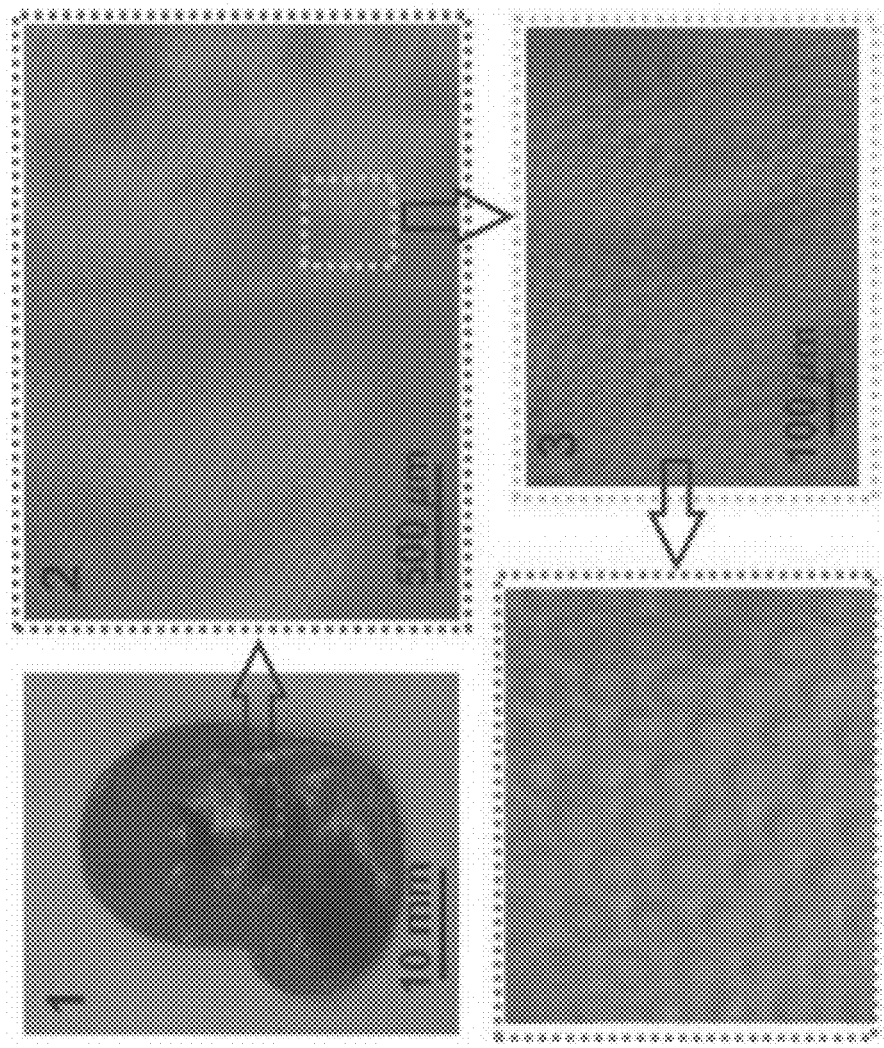
FIG. 15 shows a nonplanar object 1500 at various levels of magnification.

FIG. 15 shows a nonplanar object 1500 at various levels of magnification. In some implementations, the object 1500 can be formed from silicone in any arbitrary, nonplanar shape. The object 1500 can be coated on its surface with a polyurethane material, such as ChronoFlex. The object 1500 can then be patterned according to the method 200 of FIG. 2, as shown as the higher levels of magnification in FIG. 15. Such an object can be useful for medical applications, such as implantable devices, because silicone is a biocompatible material while ChronoFlex also features excellent hemocompatibility and biocompatibility. Thus, the object 1500 could be safely used as an implantable medical device in a human subject without significant risk of bio-incompatibility.

Figure 16:
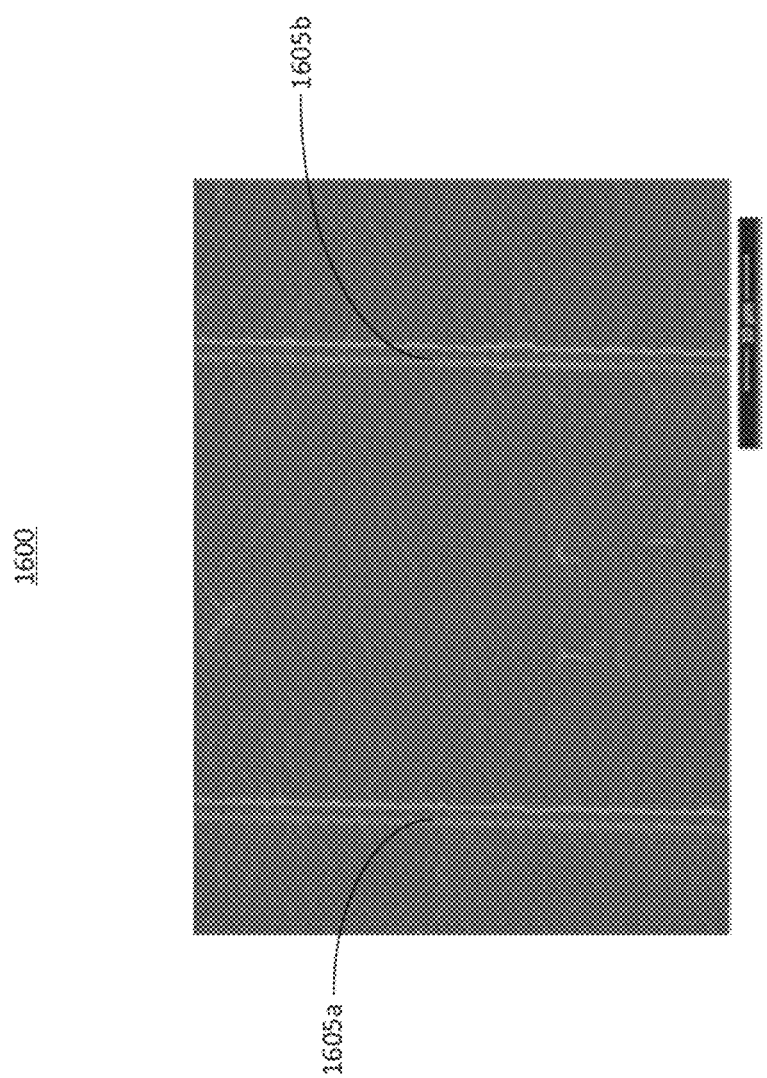
FIG. 16 shows a magnified view of a pattern transferred to the surface of an object using conformal template vacuum bagging.

FIG. 16 shows a magnified view 1600 of a pattern transferred to the surface of an object using conformal template vacuum bagging. The pattern includes two parallel lines 1605a and 1605b. Each of the lines 1605a and 1605b has a width of significantly less than 10 microns. In this example, the surface was coated with Tecoflex MG8020. The flexible stamp used to imprint the lines 1605a and 1605 was formed from PDMS. For illustrative purposes, contrast was enhanced via metal deposition onto the surface of the object. In particular, a 10 nm layer of titanium was deposited on the surface of the object.

B. Micropatterned Implantable Balloons

Anchoring and adhesion to biological tissues are critical for most cardiovascular implants. Cardiovascular plugs, occluders, stents, and valves are typically anchored by one or more of the following mechanisms: radial pressure against tissue, active fixation with barbs or hooks that penetrate tissue, sutures, and surgical adhesive or tissue glue. All of these mechanisms, especially fixation by hooks and anchors could potentially cause damage to tissues. A variety of technologies exist that provide anchoring of implants with inflating balloons or other soft conformable surfaces bringing the implant into contact with surrounding tissues. These approaches can be useful because they provide large areas of contact between the tissue and the implant surfaces. They exert uniform forces against the tissues thus facilitating anchoring of the implant. However, the extent to which an implant is anchored utilizing these approaches can be limited by the anatomy of the patient (which dictates the shape the balloon with take) and the friction created between the tissue and the surface.

The various concepts introduced above and discussed in greater detail below may be implemented in any of numerous ways as the described concepts are not limited to any particular manner of implementation. Examples of specific implementations and applications are provided primarily for illustrative purposes.

The subject matter disclosed herein relates to a patterned balloon device including an expandable balloon wherein at least a portion of the outer surface of the balloon includes a pattern. In some implementations, the patterned balloon device enhances friction and aids in anchoring of a first object to a second object in an aqueous environment. The first object can be a medical device, implant or any other biocompatible object, which needs to be immobilized in a subject's body. The second object can be any tissue, organ, or previously implanted biocompatible object in a subject's body. The aqueous environment can be blood, lymph, saliva or any other bodily fluid. For example, cardiovascular implants, such as a stent supporting a blood vessel, must be anchored to the tissue to remain in place in spite of all hemodynamic forces acting on the implant inside the subject's body.

In some implementations, the balloon is radially or outwardly expandable from a deflated state wherein the balloon has a first volume to an inflated state wherein the balloon has a second volume, which is greater than the first volume. In some implementations, the inflated state of the balloon may have one or more levels of expansion. For example, one or more portions of the balloon may expand sequentially rather than simultaneously depending on the amount of pressure required. In some implementations, at least a portion of the outer surface of the balloon is coated in anti-microbial, anti-bacterial and/or anti-inflammatory substance. In some implementations, at least a portion of the outer surface of the balloon is coated in an adhesive substance to enhance contact with surrounding tissues or organs. The balloon can be manually coated prior to implantation or it can be provided pre-coated with one or more of the above substances.

Figure 17:
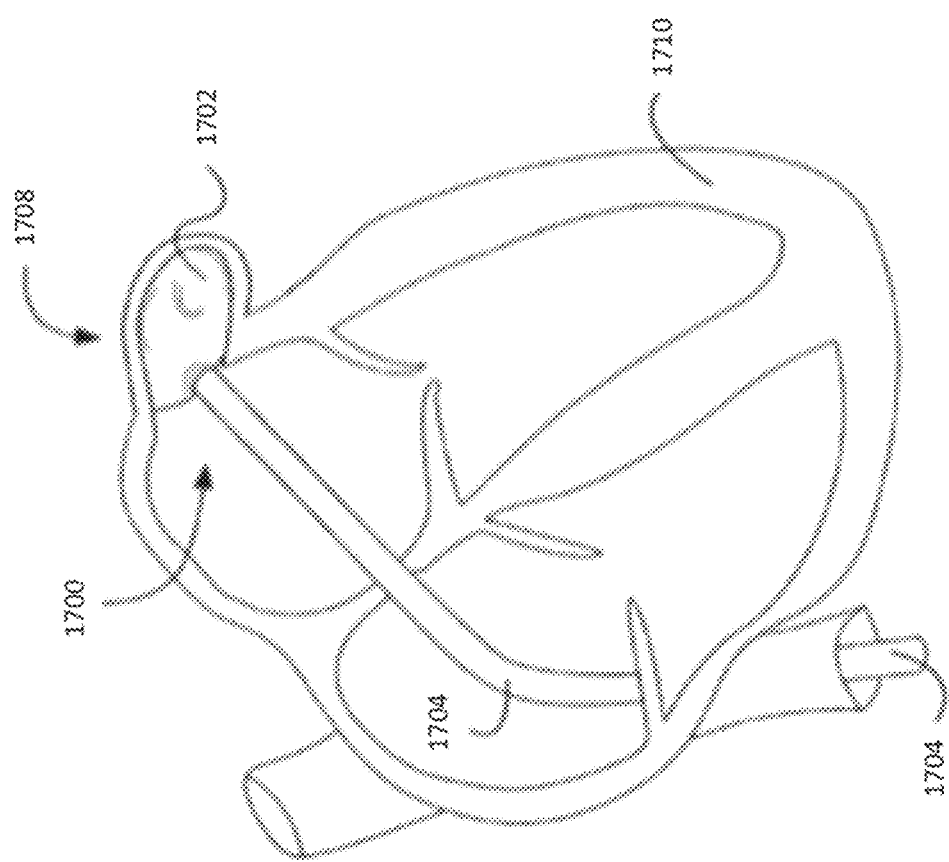
FIG. 17 illustrates an example of a patterned balloon device within the heart of a subject.

FIG. 17 illustrates an example patterned balloon device 1700 within a heart 1710 of a subject. The patterned balloon device 1700 includes an expandable balloon 1702 that can be deployed through a catheter 1704. The balloon 1702 can be deployed from the catheter 1704 and a left atrial appendage (LAA) 1708 of the heart 1710 as it is shown in the example in FIG. 17. Once deployed, the patterned balloon device 1700 is immobilized to the LAA 1708 and can be detached from catheter 1704. In some implementations, the patterned balloon device 1700 immobilizes a biocompatible object in the LAA 1708. In some implementations, the patterned balloon device 1700 is a surgical kit or other kit that includes the balloon 1702 and catheter 1704. The balloon 1702 can be configured, selected, or manufactured for the subject or patient into whom the balloon 1702 is implanted. The balloon 1702 can have a volumetric shape or geometry that substantially matches the anatomical morphology of the patient's LAA 1708. In some implementations, the balloon 1702 can include a plurality of lobes that when inflated substantially complement the LAA shape of a specific subject. In some other implementations, the balloon 1702 can be made complementary to the shape of any other body cavity having an implant. In some implementations, the morphology of a subject's LAA 1708 can be ascertained by non-invasive computer tomography (CT) imaging. The balloon 1702 can be non-spherical when inflated since a spherical device may need to be over-inflated to fill a subject's LAA 1708. The inflation of a spherical device can induce strain on both the elastomeric material of the spherical device, the multi-lobular LAA structures, and the tissue surrounding the LAA. Over-inflation of a spherical device can also compress the circumflex artery that runs underneath the LAA. In some implementations, the balloon 1702 can be manufactured for a specific subject. The catheter 1704 is configured for insertion through the subject's femoral artery. The tip of the catheter 1704 is advanced through a subject's arterial system toward the subject's LAA. The catheter 1704 includes an elongate flexible body that can include PET, nylon, polyethylene, polyether ether ketone, or any combination thereof. In some implementations, the catheter 1704 is configured for insertion through a laparoscopic or other surgical opening. In some implementations, the catheter 1704 has a length between about 50 cm and about 150 cm. In some implementations, the outer diameter of the catheter 1704 is between about 0.2 mm and about 6 mm, between about 0.5 mm and about 5 mm, between about 0.5 mm and about 4 mm, and between about 1 mm and about 3 mm. In some implementations, the catheter 1704 includes a solid core to enable the deployment tip of the catheter 1704 to be controlled. For example, the core can include a stainless steel, nitinol, nickel titanium alloy, or polymeric materials that can be rotated by the surgeon to control the rotation of the catheter 1704. In some implementations, the catheter 1704 includes radiopaque to enable the surgeon to visualize the placement of the catheter 1704 within the patient with the use of X-ray imaging. In some implementations, the catheter 1704 includes an inflatable balloon. The inflatable balloon is configured to inflate and at least partially block the LAA during the deployment of the balloon 1702.

Figure 18:
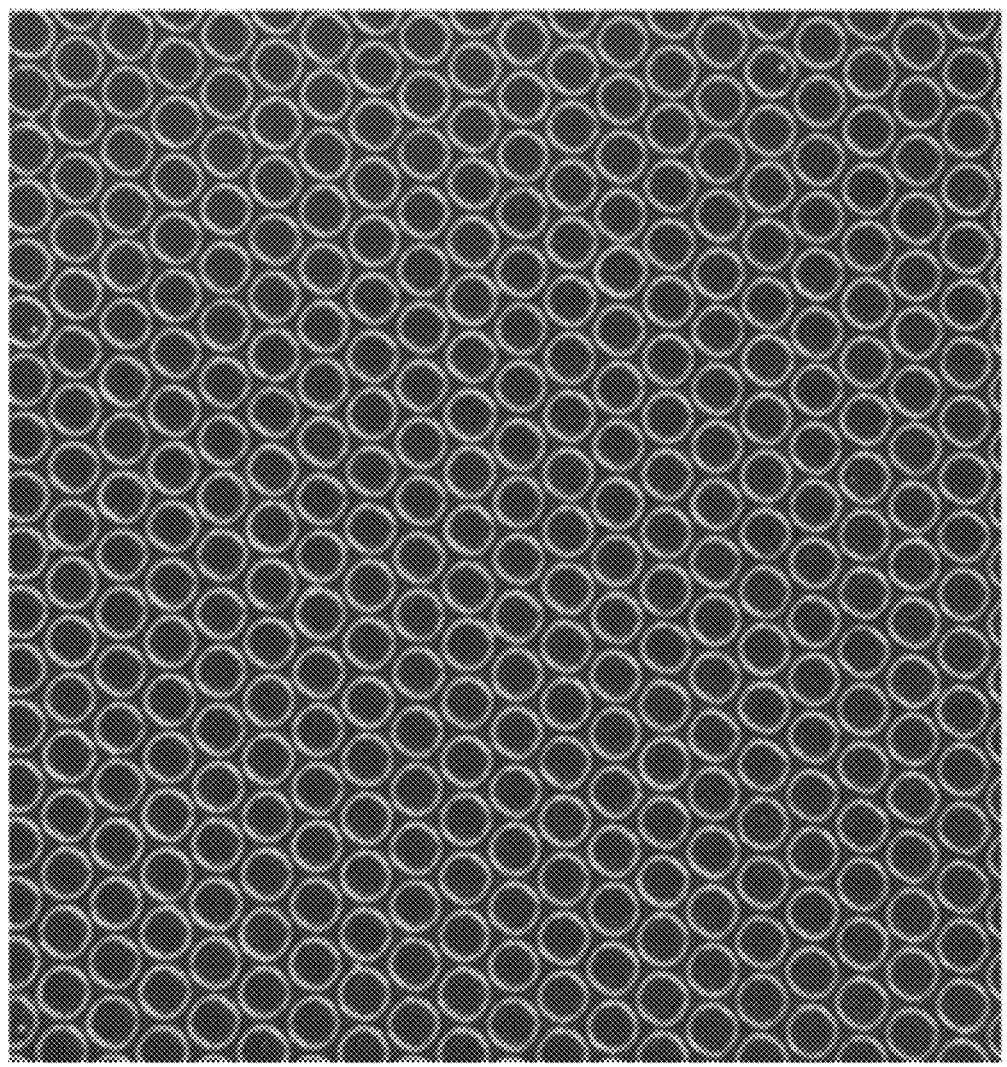
FIG. 18 shows an example of a pattern.
Figure 19:
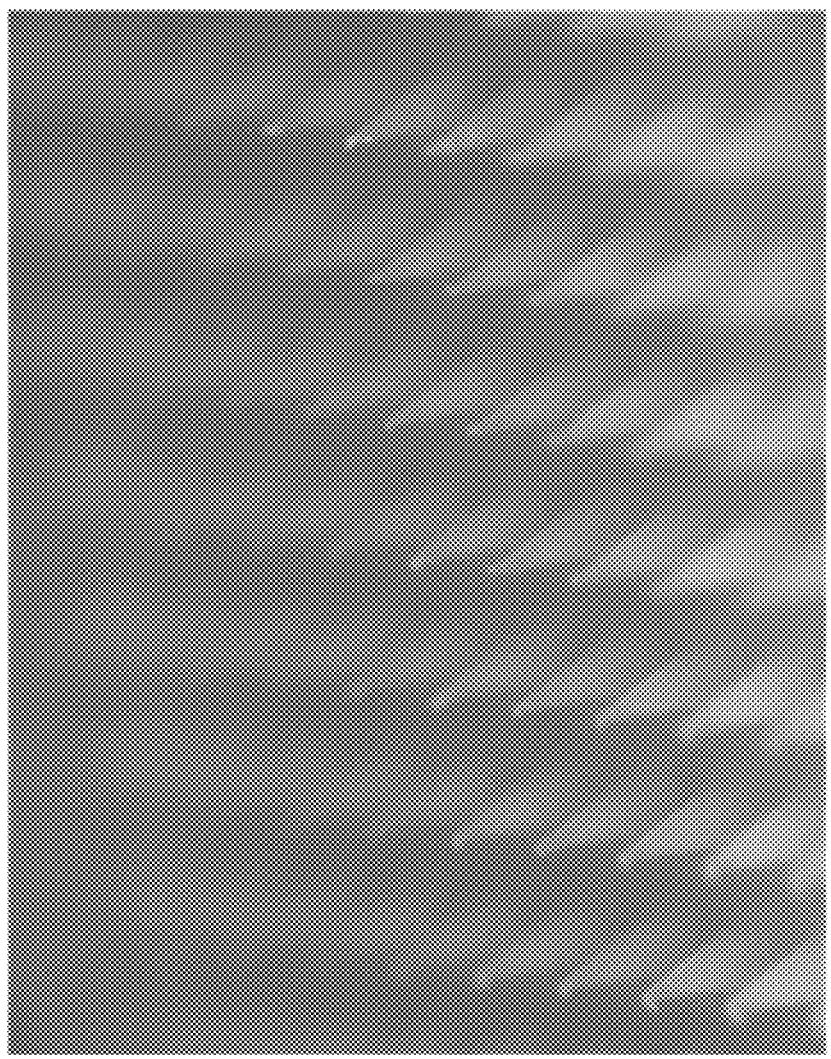
FIG. 19 shows an example of a corrugated pattern.

In some implementations, the patterned balloon device includes a pattern, which enhances friction with the application of pressure between tissues and the patterned surface of the balloon. For example, FIG. 18 shows a pattern 1800 that can be used to enhance friction. However, other patterns also may be selected. For example, patterns can be selected to help move fluid away from the interface between the patterned balloon surface and tissues, and/or deform or penetrate tissues to increase surface area or provide mechanical interlocking between the patterned balloon device surface and tissues. In some implementations, the pattern can be a hexagonal array inspired by tree frogs as described above in connection with Section A. Other patterns may also provide pathways for fluids such as blood to be displaced allowing for areas of dry contact dry contact between tissues and the patterned balloon device. Other array patterns can also include cylindrical, rectangular, spherical, polygonal, triangular, circular, and ellipsoid features or any geometrical shape suitable for increasing contact friction or any combination thereof. In some implementations, the selected pattern can be a corrugated pattern, which can deform tissues increasing the surface area of contact. In some implementations, the pattern is a microneedle pattern, such as the pattern 1900 shown in FIG. 19, which can penetrate or interlock with tissues. The pattern can be a micro- or nano-pattern depending on the size of an individual feature in the pattern. The pattern can also be a combination of micro- and nano-patterns. In some implementations, the pattern is embedded in the walls of the balloon as part of the design. In some implementations, the pattern is attached to the outer surface of the balloon in a permanent or a removable manner. In some implementations, the pattern encompasses the whole outer surface of the balloon. In some implementations, the pattern covers at least a portion of the outer surface of the balloon. In some implementations, the pattern includes features uniformly distributed in an array. In some other implementations, the pattern includes a higher number of features distributed in at least a portion of the patterned and a lower number of features distributed in another portion of the pattern, forming a non-uniform distribution. In some implementations, features can be disposed perpendicularly to the surface. In some other implementations, features can be disposed at an angle to the surface or to be slanted. In some implementations, all features are slanted in the same direction. In some other implementations, features in the same array can be slanted in different directions or they can be perpendicular.

FIG. 20A illustrates an example patterned balloon device 1700 in an uninflated state. FIG. 20B illustrates a cross-sectional view of the example patterned balloon device 1700 in an inflated state. The inflated state can be any state where the balloon 1702 is expanded with respect to the configuration of the balloon 1702 prior to being deployed, for example when the patterned balloon device is within the catheter 1704. The balloon 1702 can be expanded or otherwise inflated with a fluid, gas, foam, or other material. In some implementations, the balloon 1702 can be self-expanding. For example, the walls of the balloon 1702 can include nitinol ribs that deploy to an expanded state once the patterned balloon device 1700 is deployed from the catheter 1704. In some implementations, the patterned balloon device 1700 includes a valve 1712 through which the balloon 1702 can be filled. The valve 1712 can enable a lumen 1722 to be inserted in a first direction and into an interior space of the balloon 1702 but substantially prevents fluid from flowing in the opposite direction. The balloon 1702 can be monolithically integrated with the valve 1712. The valve 1712 can enable a surgeon to fill the balloon 1702 without leakage once disengaged from the catheter 1704. The balloon device 1702 can be filled with a hardening material to stabilize the balloon 1702 within the body cavity or in the example the LAA 1708 after implantation. The fluid to inflate the balloon 1702 can be passed to the interior of the patterned balloon device 1700 via a lumen 1722. In some implementations, the lumen 1722 is inserted through a valve 1712 during the patterned balloon device's non-deployed state, for example when the balloon 1702 is in the catheter 1704.

The valve can be monolithically integrated into the patterned balloon device 1700 during the molding process. Monolithically integrating the valve 1712 with the patterned balloon device 1700 can enable the balloon 1702 to be inflated to a high pressure without delamination of the valve 1712 from its walls of the patterned balloon device 1700. The valve 1712 can include a polymeric septum that is pierced by lumen 1722. Once the patterned balloon device 1700 is deployed and secured in the LAA 1708, the lumen 1722 can be retracted. The polymeric septum valve can seal the location where lumen 1722 previously pierced the septum, sealing the interior of the patterned balloon device 1700. The valve 1712 can also include a cured material, for example quick setting epoxy can be applied to the opening left by the retracted lumen 1722. The valve 1712 can include a mechanical valve that is open to fill the balloon 1702 and then closed once the balloon 1702 is filled. The valve 1712 can include wings 1714, coupled to the internal side of the valve 1712 to protect the opposing wall of the patterned balloon device 1700 from being pierced accidentally by the lumen 1722 during deployment of the filling of the balloon 1702. A portion of the valve 1712 can extend past the walls of the balloon 1702. The portion can include attachment anchors 1718, which can be sutures. The attachment anchors can be used to secure and anchor the patterned balloon device 1700 to the surrounding tissues such as the LAA 1708. In some implementations, the attachment anchors 1718 can be coupled with the outer surface of the wall 1720 of the patterned balloon device 1700.

In some implementations, the balloon 1702 of the patterned balloon device 1700 can be fabricated using rapid prototyping techniques, such as direct 3D printing of polyurethane materials or molding from 3D printed templates of silicone materials. These materials can have a wide range of stiffness (ranging from kPa to tens of MPa) and extensibilities (e.g., up to 700%). In some implementations, the material used to fabricate the balloon 1702 is intrinsically soft as to not damage tissues or impede their function. In some implementations, the material used to fabricate the balloon 1702 is robust enough to withstand the forces exerted on the device when implanted. In some implementations, the patterned balloon device 1700 can include polyurethane, silicone, nylon, PET, or a combination thereof. In some implementations, the walls 1720 (or other components of the balloon 1702) can include a non-stretchable polymer, such as polyethylene terephthalate (PET), polytetrafluoroethylene (PETE), nylon, or polyvinyl chloride (PVC). In some implementations, the walls 1720 of the balloon device 1702 can be reinforced with fabric, metal mash or wire, or other materials.

In some implementations, the balloon 1702 can be manufactured using a mold that includes both a hard portion (Veroclear, Stratasys) and soft portion (Tango+, Stratasys). One mold can be manufactured for each side of the balloon 1702. Each mold can be filled with a homogeneous silicone blend of 69 wt % Dragon Skin®20 (DS20; Smooth-On, Inc.), 10.3 wt % Silicone Thinner® (Smooth-ON, Inc) and 20.7 wt % Sylgard®184 mixture. The silicone blend and molds can then be baked in an oven at 100° C. for 35 minutes. Nest, the partially cured silicone blend can be removed from the molds. The two halves of the balloon 1702 can be aligned and bonded together with DS20 pre-polymer. The coupled halves can be returned to the oven at 100° C. for one hour. Pure DS20 can be used instead of the silicone blend for the seams because pure DS20 has a higher viscosity and stays in position after placement on the seam, Once fully cured and cooled, the balloon 1702 can be plasma treated and soaked in 12 vol % 3-glycidoxypropyltrimethoxysilane (GPTS; Sigma Aldrich) for one hour. After cleaning and drying, the balloon 1702 can be rinsed in a solution of −10 wt % PCU in DMAC (e.g., provided by Sigma Aldrich). The balloon 1702 can be baked in an over at 70° C. for 2 hours, and then dipped again into PCU solution. The balloon 1702 can be placed in a 70° C. overnight to fully cure PCU surface coating. In some implementations, other injection molding processes can be used to manufacture patterned balloon devices described herein.

Figures 21A, 21B, 21C:
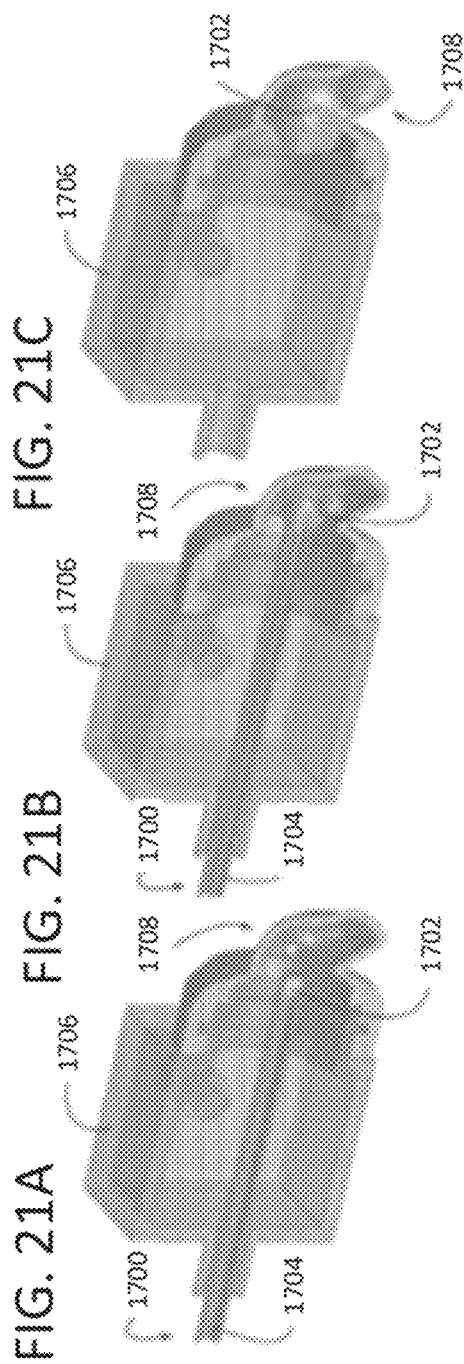
FIGS. 21A-21C illustrate example methods for implanting a subject-specific patterned balloon device.

FIGS. 21A-21C and 6A-6D illustrate example methods for implanting a patterned balloon device 1700. The patterned balloon device 1700 can be deployed via a number of procedures. In some implementations, the patterned balloon device 1700 can be deployed via a transcatheter method or surgically. For example, inflated from the ostium of the LAA 1708 or from the distal end of the LAA 1708. FIGS. 21A-21C illustrate an example patterned balloon device 1700 during different stages of transcatheter deployment. FIGS. 21A-21C illustrate deployment of patterned balloon device into an in vitro testing system 1706. The in vitro testing system 1706 includes an artificial LAA 1708. While illustrated in relation to the in vitro testing system 1706, the patterned balloon device described herein is also configured for in vivo testing. FIG. 21A shows the patterned balloon device 1700 contained within catheter 1704. The patterned balloon device 1700 can be fully contained with the catheter 1704 in an undeployed or deflated stated during the procedure to snake the tip of the catheter 1704 from an insertion site to the target body cavity or a subject's left atrium. FIG. 21B shows the patterned balloon device 1700 after partial deployment into the artificial LAA 1708 from catheter 1704. FIG. 21C shows the patterned balloon device 1700 fully deployed into the artificial LAA 1708. As illustrated in FIG. 21C, the catheter 1704 can be retracted from the artificial LAA 1708 after deployment of the patterned balloon device 1700. As illustrated in FIG. 21A, the patterned balloon device 1700 can be collapsible to fit within the catheter 1704 and then expanded to fir within a subject's LAA. In some implementations, the balloon 1702 is expanded and deployed by infusing a fluid into the balloon 1702. The fluid used to fill the balloon 1702 can be cured (chemically, thermally, or with fiber coupled to UV light) to ensure the deployed patterned balloon device 1700 retained its shape and stayed immobilized or anchored within the body cavity or the LAA. Furthermore, by solidifying the liquid, potential issues of balloon rupture will be reduced. As described above, the curable fluid is configured to have mechanical properties, such that the solidified balloon 1702 can accommodate the natural movement of body tissues such as the natural contractions of the left atrium and other portions of the heart. The balloon 1702 can be filled with epoxies, polyethylene glycol, collagen-based biocompatible polymeric gels, silicon, polyurethane, poly(methyl methacrylate), saline, self-expanding foam particles, or any combination thereof. The fluid or other material that fills and inflates the balloon 1702 can be referred to as an inflation fluid. In some implementations, a contrast agent or radiopaque material can be added to the filling of the balloon 1702 to make the patterned balloon device 1700 visible to imaging devices. In some implementations, the fluids used to fill the balloon 1702 are stored in reservoirs that are coupled to the patterned balloon device 1700 via the catheter 1704. The balloon 1702 can be filled by injecting the fluid from the reservoir and into the balloon 1702 via the lumen 1722.

Figure 22A:
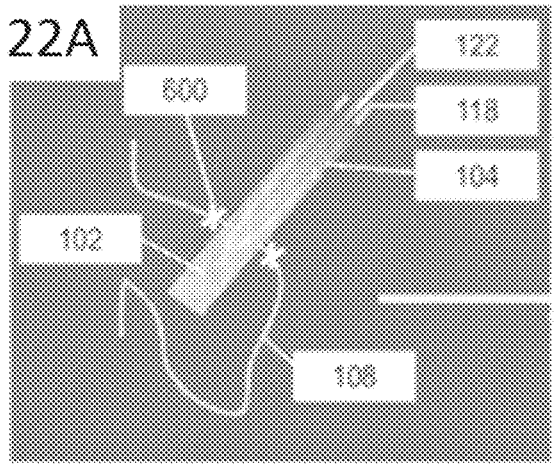
FIGS. 22A-22D illustrate example methods for implanting a subject-specific patterned balloon device.
Figure 22B:
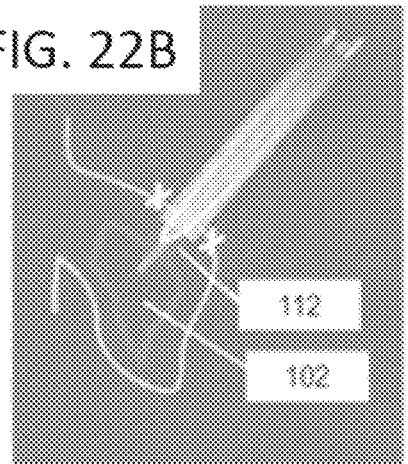
Figure 22C:
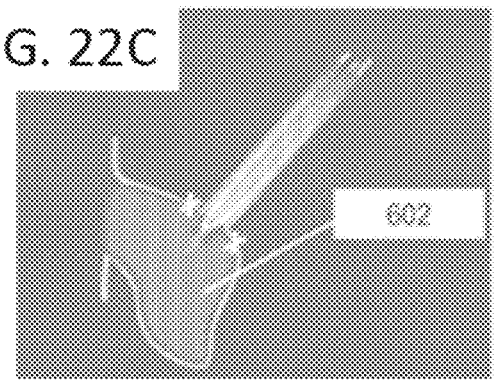
Figure 22D:
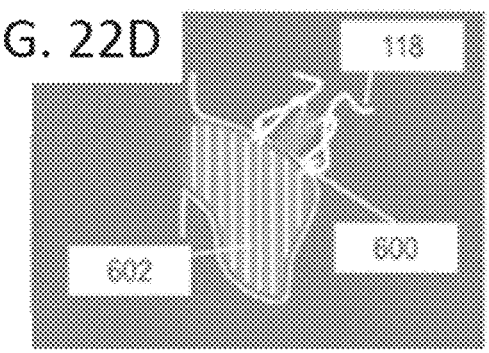

FIGS. 22A-22D illustrate an example patterned balloon device 1700 during the stages of deployment from the distal end of the LAA 1708. FIG. 22A illustrates a first step where a small incision is made in the LAA 1708. The catheter 1704, which during the initial steps contains the patterned balloon device 1700, attachment anchors 1718, and a lumen 1722, is inserted through the incision and in to the LAA 1708. As illustrated in FIG. 22A, purse string sutures 600 are made near where the catheter 1704 is inserted into the LAA 1708. FIG. 22B illustrates the retraction of the catheter 1704. As the catheter 1704 is retracted, the patterned balloon device 1700 is deployed into and remains within the LAA 1708. FIG. 22C illustrates the filling (also referred to as the expansion or inflation) of the balloon 1702. The lumen 1722 passes through the valve 1712 and into the interior of the balloon 1702. The interior of the balloon 1702 can be filled with fluid 602, such as liquid epoxy. As the balloon 1702 is filler, the balloon 1702 expands to fill the volume of the LAA 1708. After a predetermined amount of time, the fluid 602 cures and hardens. In some implementations, the patterned balloon device 1700 can be filled with a fluid or other material that does not cure or otherwise harden over time, for example saline. FIG. 22D illustrates the anchoring of the patterned balloon device 1700 to the LAA 1708. The attachment anchors 1718 can be sutures that are tied or otherwise coupled with the purse string sutures 600 placed in the LAA 1708. The attachment 1718 can hold the patterned balloon device 1700 in place and within the LAA 1708. In some implementations, the attachment anchors 1718 can hold the balloon 1702 in place as the fluid filling the balloon 1702 cures. In some implementations, the patterned balloon device 1700 does not include attachment anchors and immobilization is achieved through friction forces generated between the patterned balloon device 1700 and surrounding tissues or other implanted devices.

In some implementations, the patterned balloon device is integrated into the body of the object, which is to be implanted. In some implementations, the object is manufactured such that the design of the object includes a patterned balloon device permanently integrated. In some implementations, the patterned balloon device is attached to the object prior to implantation. In some implementations, the patterned balloon device is implanted separately from the object depending on which surface of the object requires anchoring to surrounding tissues or organs.

In some implementations, the patterned balloon device can transition from a deflated state to an inflated state be introducing gas, liquid or malleable semi-solid into the interior of the balloon. The balloon can be inflated by a manual or automatic pump or any suitable inflation device known in the art. The patterned balloon device can be pressurized to a desired level. In some implementations, once the patterned balloon device has been inflated it yields a conformal contact with surrounding tissues or organs such that the implant is anchored in place. In some implementations, the portion of the patterned balloon device forming a conformal contact with tissues or organs is maximized allowing for the largest possible portion if not all of the patterned surface to interface with tissues or organs, which would yield the strongest attachment forces for the implant. In some implementations, inflation of the patterned balloon device is initiated once the implant is positioned in the target location in a subject's body. For example, in the interior of a blocked blood vessel.

In some implementations, the subject is a human patient in need of medical device implantation. The subject can also be any mammal such as a monkey, mouse, rat, dog, cat, sheep or ant animal that requires medical device implant.

The subject matter disclosed herein also relates to a method of fabrication of a patterned balloon device. The method includes fabricating a thin-walled balloon by means known in the art such as blow molding, dip coating, vacuum bagging, or conventional molding or casting or a combination thereof. In some implementations, fabrication of a patterned balloon device includes utilizing a soluble core, which can be solubilized and removed following curing of the balloon. In some implementations, the balloon is prefabricated in the shape desired for the application.

The method also includes fabricating of the pattern. In some implementations, patterns with a desired features or geometry are fabricated on a planar template via methods known in the art such as lithography, 3D printing, laser cutting, and stereolithography or any combination thereof. Once patterns are formed on a planar template, they can be transferred to flexible elastomeric masters. These masters can either be used to cast the patterns in or to emboss those patterns onto the balloon.

In some implementations, the method includes pattern transfer. Pattern transfer can include, for example, bonding patterns prefabricated in an elastomeric master to the surface of the balloon through methods such as thermoplastic bonding, solvent welding, or adhesive bonding or any combination thereof.

In some implementations, the method includes embossing patterns on the balloon. Pattern embossment includes laminating the patterned master in conformal contact to the balloon surface, applying pressure and heat to thermoform the pattern in the balloon surface.

Figure 23:
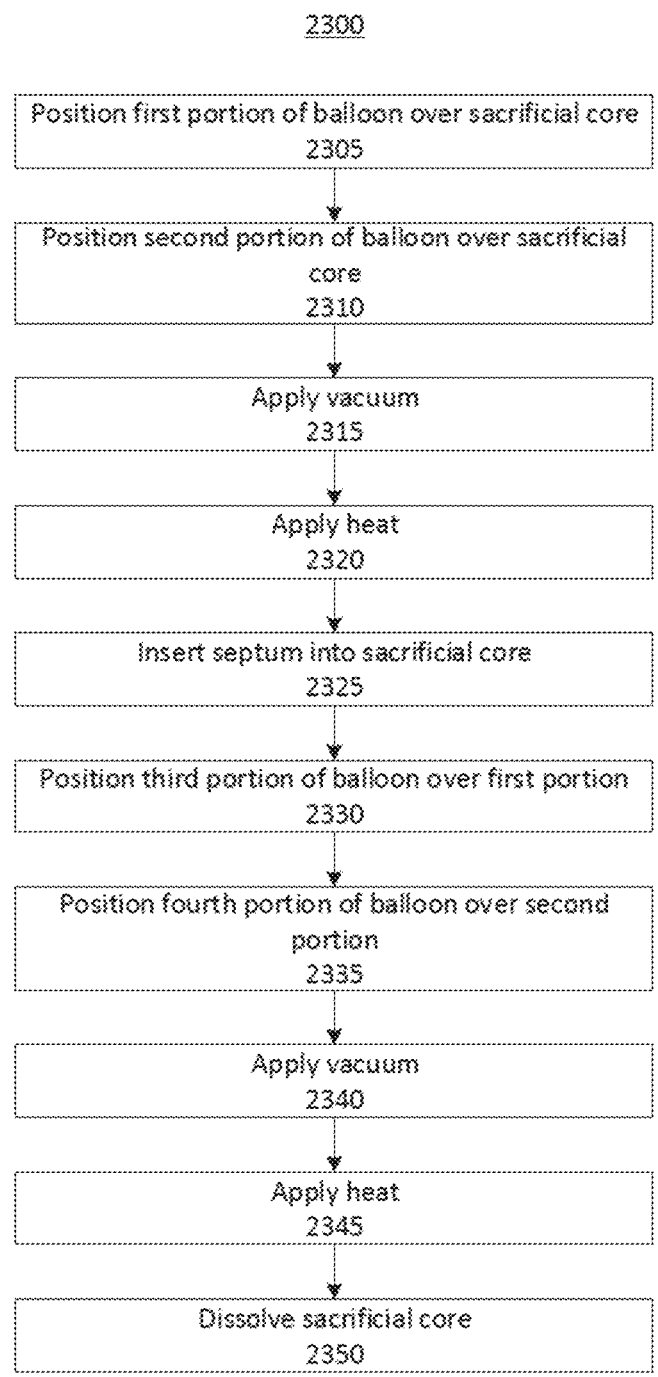
FIG. 23 illustrates a flowchart of a method for fabricating an implantable balloon device.

FIG. 23 illustrates an example method 2300 for fabricating an implantable balloon device. FIGS. 24A-24E show stages of construction of an implantable balloon device according to the method of FIG. 23. FIGS. 23 and 24A-24E are described together below.

Figure 24A:
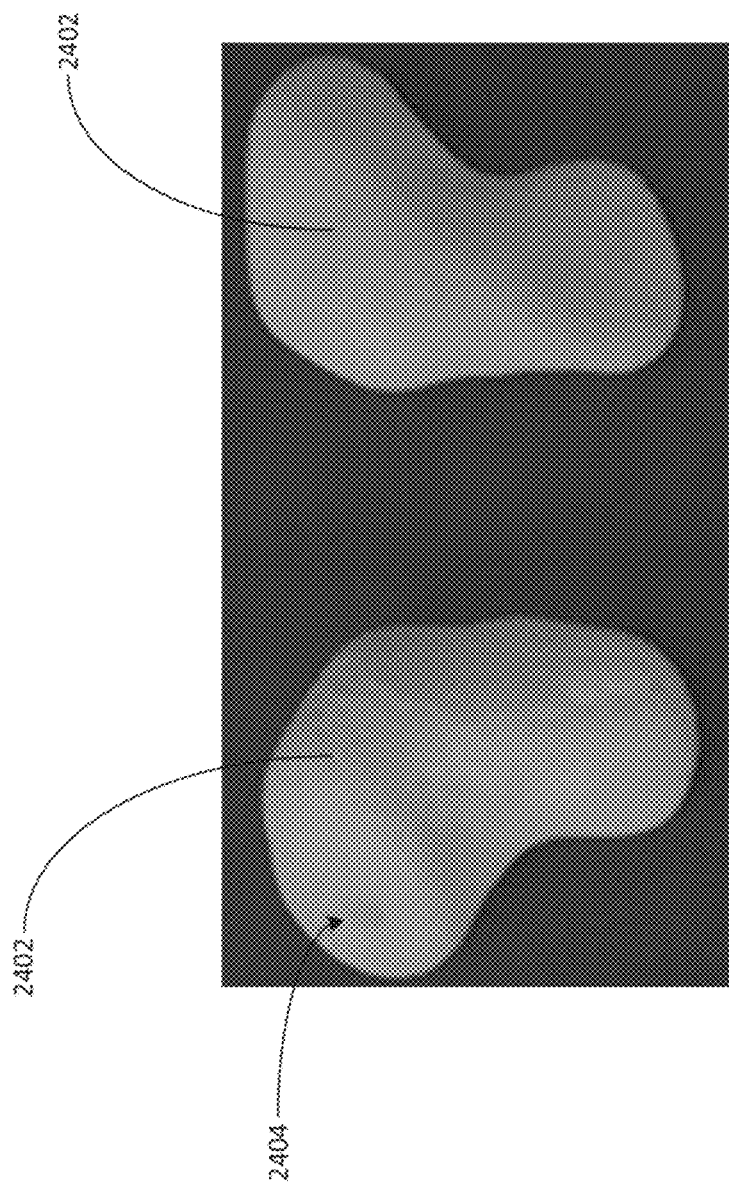
FIGS. 24A-24F show stages of construction of an implantable balloon device according to the method of FIG. 23.

Referring to FIG. 23, the method 2300 may include positioning a first portion of an inflatable balloon over a lower portion of a sacrificial core (stage 2305). FIG. 24A depicts two views of a sacrificial core 2402. The sacrificial core 2402 includes a hole 2404. The hole can be configured for receiving a septum at a later stage of the method 2300. The salt core 2400 can be designed to have an arbitrary geometry. For example, the geometry can be based on volume rendered 3D segmentation from patient CT images such that the salt core is shaped to fit into a particular tissue region, such as the patient's LAA. Different parameters such the location of a septum with respect under-sizing, and irregularity of the geometry can be considered in the design of salt core 2402.

In some implementations, a mold for the salt core 2402 can be initially 3D printed, and can be inverted to a material such as a highly extensible silicone mold made from Ecoflex. In some implementations, fine particulate salt can be mixed with water (e.g., with the ratio of 6 to 1) to form a slurry, and the slurry can be put into the Silicone mold. Vacuum can be used to degas entrapped bubbles. The silicone mold can be dried. For example, in some implementations, drying can be done in two steps, including using a 100° C. oven for a first step and performing a post bake of 2 hours at 140° C. for a second step. The salt cores 2400 can be taken out of the silicone molds and stored for the next stages of the method 200.

Figure 24B:
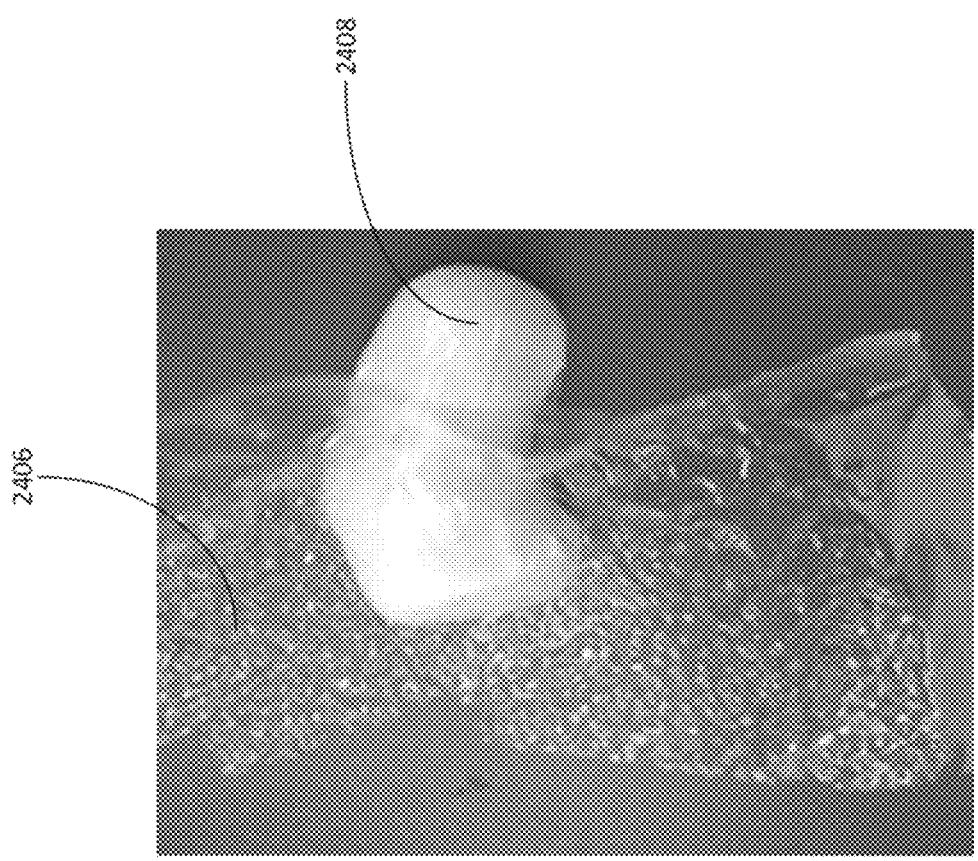

In some implementations, the balloon can be fabricated in two halves using pressure forming of polyurethane films on 3D printed molds. Thus, each half of the balloon can include a respective polyurethane film. For example, a rigid material such as Veroclear can be used to form a mold for the polyurethane film, and the polyurethane film can be pressure formed (e.g., using a MiniSTAR S®, at approximately 5 bar) on the top and bottom of Veroclear molds. After that each side of the balloon can be trimmed to become a half balloon. FIG. 24B shows a half balloon 2406 pressure formed on a mold 2408. The half balloon 2406 has not been trimmed yet in the depiction of FIG. 24B.

Figure 24C:
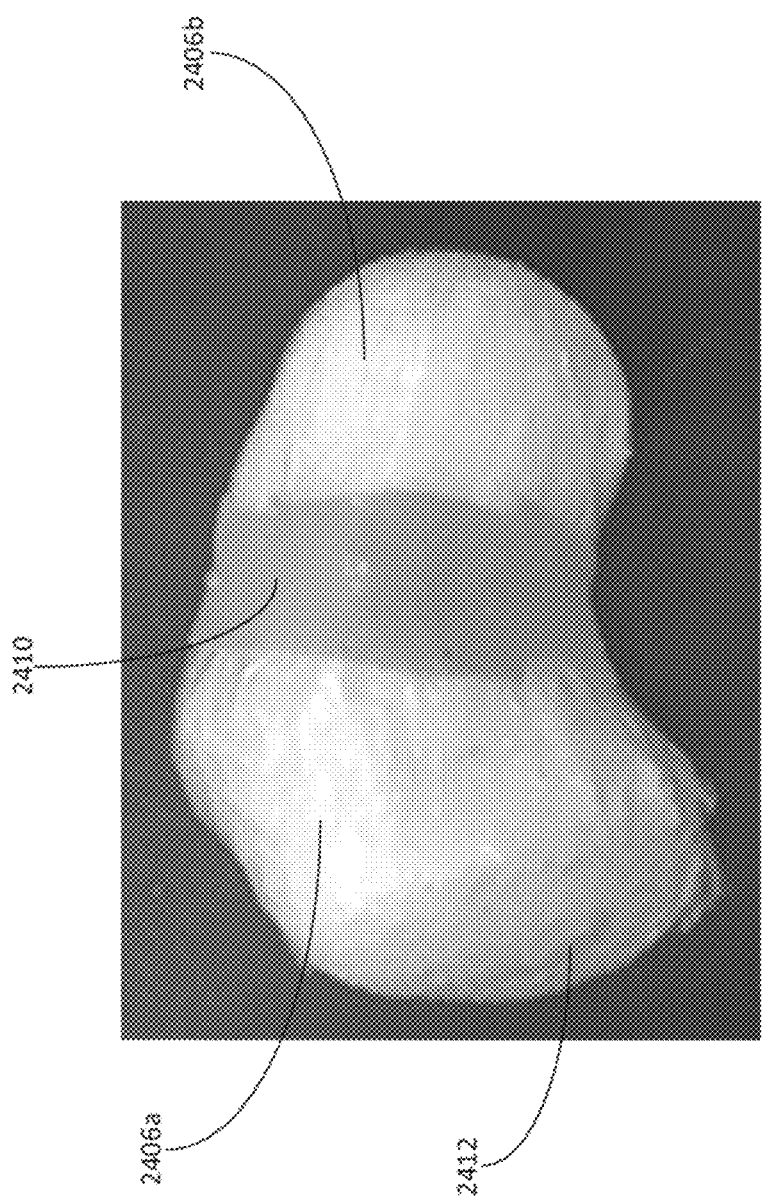

The method 2300 may include positioning a second portion of the inflatable balloon over an upper portion of the sacrificial core (stage 2310). In some implementations, the second portion of the inflatable balloon can be formed from a polyurethane film in the same manner described above in connection with FIG. 24B. For example, the same mold 2408 can be reused to pressure form the second half of the balloon. In some implementations, the second half of the balloon can be positioned over the upper portion of the sacrificial core such that the second portion of the inflatable balloon at least partially overlaps the first portion of the inflatable balloon. This is depicted in FIG. 24C, in which the first half 2406a of the balloon and the second half 2406b of the balloon are positioned over the sacrificial core.

In some implementations, the first half 2406a of the balloon and the second half 2406b of the balloon may overlap by a distance in the range of about 1 mm to about 3 mm. For example, the first half 2406a of the balloon and the second half 2406b of the balloon may overlap by a distance of about 2 mm. In some implementations, an elastomeric string 2410 can be wrapped around the overlapping portions of the first half 2406a of the balloon and the second half 2406b of the balloon, as depicted in FIG. 24C. For example, the elastomeric string can be formed from a material such as Elastosil, and can have a thickness in the range of about 250 microns to about 350 microns.

Figure 24D:
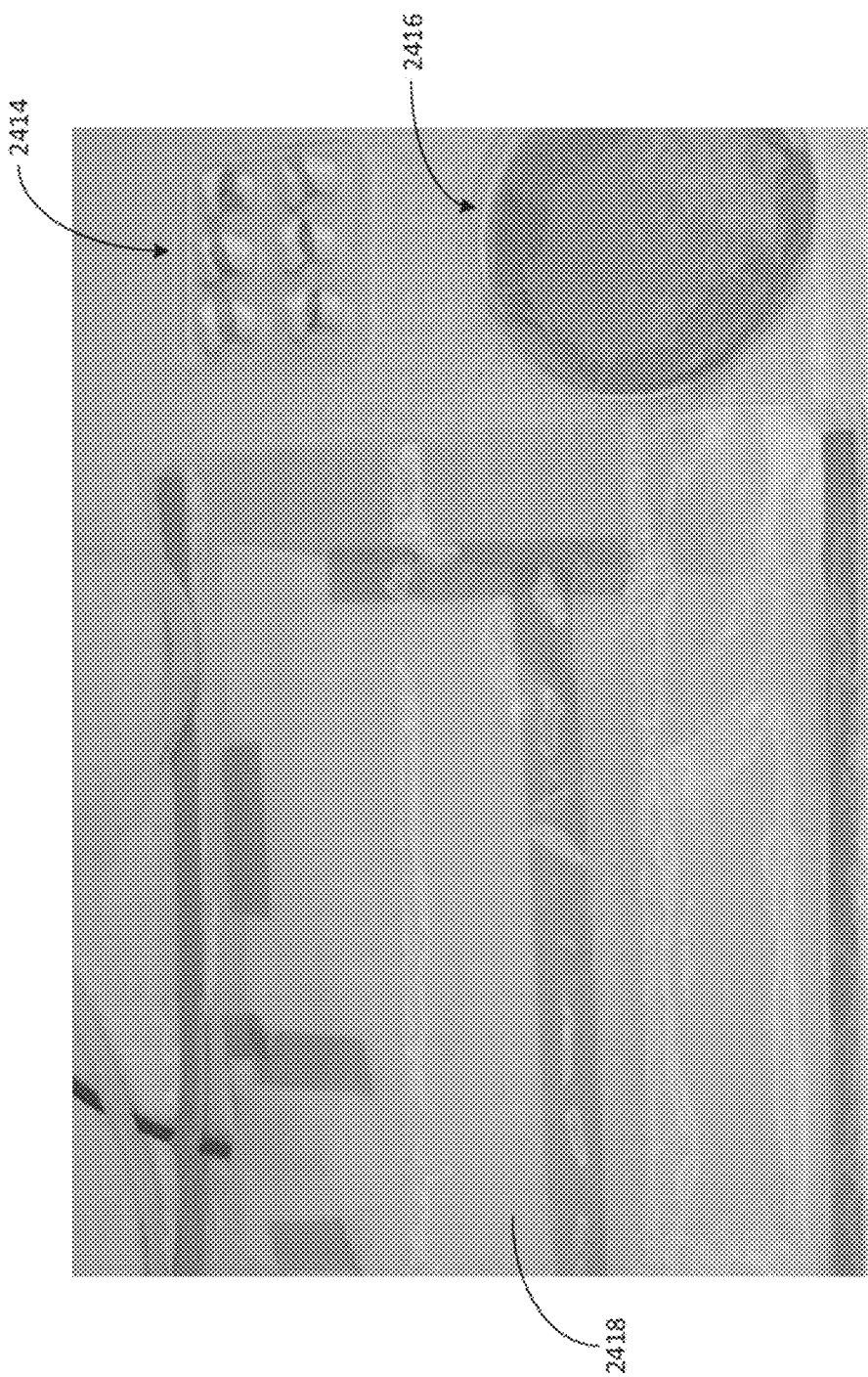
Figure 24E:
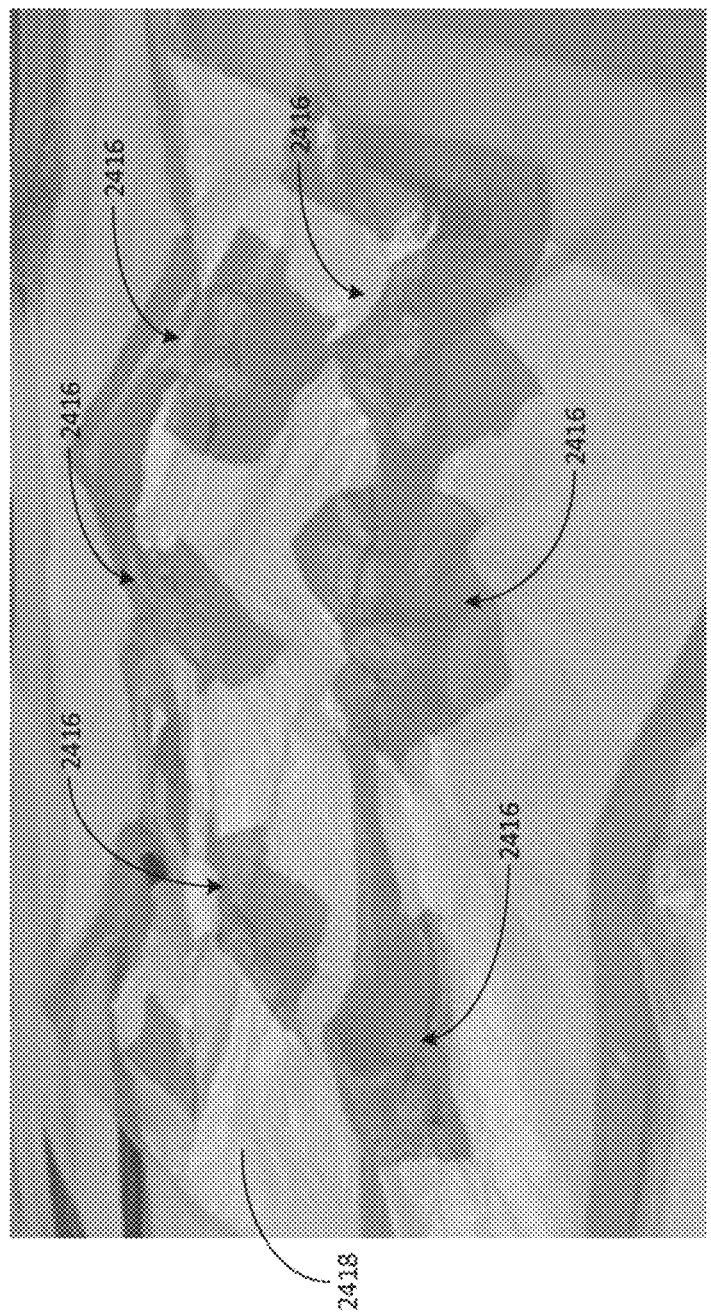

The method 2300 may include applying vacuum to the first portion of the inflatable balloon and the second portion of the inflatable balloon (stage 2315). In some implementations, vacuum can be applied using a vacuum bag assembly similar to those described above, for example, in connection with the method 200 of FIG. 2. For example, the polyurethane-encased sacrificial core can be wrapped inside a larger unpatterned elastomeric film. FIG. 24D shows a plurality of such polyurethane-encased sacrificial cores 2414 ready to be processed in this manner, along with elastomeric films 2416 and a vacuum bag 2418. In some implementations, breathers can also be placed on each side of the elastomeric films inside the vacuum bag 2418, and vacuum (e.g., about −0.75 bar) can be applied. FIG. 24E shows six elastomeric films, each wrapped around a respective polyurethane-encased sacrificial core, inserted into the vacuum bag 2418 with vacuum applied.

The method 2300 may include applying heat to the first portion of the inflatable balloon and the second portion of the inflatable balloon to form a thermoplastic bond between the first portion of the inflatable balloon and the second portion of the inflatable balloon (stage 2320). For example, the vacuum bag 2418 can be placed inside an oven (e.g., around 100° C.) for one to three hours to form a thermoplastic bond between the first portion of the balloon and the second portion of the balloon.

In some implementations, the method 2300 can include inserting a septum into the sacrificial core (stage 2325). For example, as depicted in FIG. 24C, a septum 2412 can be inserted into the sacrificial core (e.g., into the hole originally formed in the sacrificial core, as described above). In some implementations, the septum can have a roughly cylindrical shape with a diameter of about 2 millimeters and a length of about 6 millimeters. The septum can be made from a polyurethane material such as Tecoflex®—SG85A. To accomplish this, a mold of the septum 2412 can be designed, 3D printed from (e.g., using a material such as Veroclear), and then inverted on a silicone mold. The silicone mold can be filled with dry polyurethane pellets and placed inside a vacuum oven (e.g., at the temperature of about 170° C.) to cause the pellets to melt. After the mold is fully filled with the melted polyurethane, it can be cooled down and the septum 2412 can be removed and inserted into the sacrificial core as shown in FIG. 24C.

The method 2300 may include positioning a third portion of the inflatable balloon over the first portion of the inflatable balloon (stage 2330) and positioning a fourth portion of the inflatable balloon over the second portion of the inflatable balloon such that the fourth portion of the inflatable balloon at least partially overlaps the third portion of the inflatable balloon (stage 2335). In some implementations, stages 2330 and 2335 of the method 2300 can be performed in a manner similar to that of stages 2305 and 2310. For example, polyurethane films can be pressure formed over a mold and trimmed to size, and then positioned over opposite halves of the sacrificial core.

The method 2300 may include applying vacuum to the third portion of the inflatable balloon, the fourth portion of the inflatable balloon, and the septum (stage 2340) and applying heat to the third portion of the inflatable balloon, the fourth portion of the inflatable balloon, and the septum to form a thermoplastic bond between the first portion of the inflatable balloon, the second portion of the inflatable balloon, the third portion of the inflatable balloon, the fourth portion of the inflatable balloon, and the septum (stage 2345). In some implementations, these stages may be performed in a manner similar to that of stages 2315 and 2320 described above.

In some implementations, the film used to wrap the polyurethane encased sacrificial core for stage 2340 can be a film having a pattern on its surface. The pattern can allow the film to serve as a stamp. For example, such a stamp can be formed in a manner similar to the flexible stamps described above in Section A in connection with the method 200 of FIG. 2. Thus, in some examples, a silicon wafer can be micropatterned using photolithography techniques. After fully curing the wafer, it can be inverted to a silicone (e.g., Sylgard) master template. After spin coating with an elastomeric material such as Elastosil (e.g., at 800 RPM), the template can be cured, for example by exposure to heat. Finally the elastomeric stamp can be peeled off, for use in thermoplastic assembly using vacuum bagging. The vacuum and heat can cause the pattern on the surface of the balloon to become imprinted on a surface of the balloon, as described above.

Figure 24F:
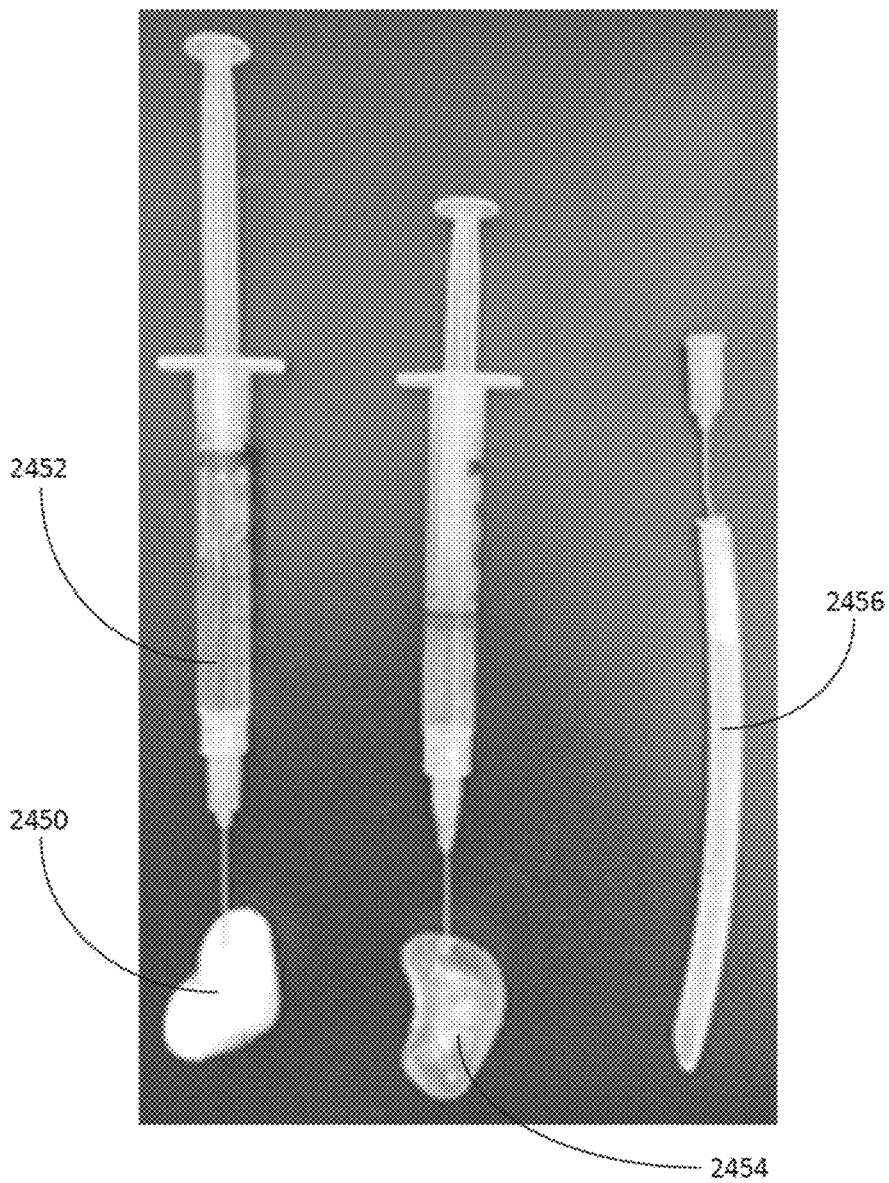

The method 2300 may include dissolving the sacrificial core (stage 2350). In some implementations, the septum of the sacrificial core can be punctured with needles or luer-lock, and attached to a perfusion system that circulates water. The perfusion system can cyclically fill the balloon with water and infuses the water out. Over these cycles, the sacrificial core can be fully dissolved. Eventually, after dissolving the salt cores, the balloon can be dried, for example with cyclic application of pressure and vacuum. The final product after drying may be able to fit inside a French 14 tube, as illustrated in FIG. 24F. For example, on the left hand side of FIG. 24F is a balloon 2450 with a soluble sacrificial core still intact and a needle 2452 puncturing a septum of the balloon 2450. In the middle of FIG. 24 is shown a balloon 2454 whose sacrificial core has already been dissolved as described above. On the right hand side of FIG. 24F is a balloon that has been dried and placed inside a FR 14 tube labeled 2456.

C. Thin Inflatable Actuators

Surgery is an invasive medical procedure requiring incisions of varying sizes, which carries with it an inherent risk. Incisions made by even the most skillful surgeons can leave painful wounds that take a long time to heal and form scar tissue. Therefore, the medical field has been moving toward replacing surgeries with minimally invasive procedures whenever possible. These procedures limit the size of incisions required and thus lessen the wound-healing time, associated pain, and risk of infection. Advances in various medical technologies have made the transition feasible. For example, the advancement of imaging techniques has allowed radiologists to operate interventional instruments through catheters instead of large incisions. Additionally, specialized medical equipment may also be used, including fiber optic cables and miniature video cameras, which increases precision and safety.

However, issues have arisen from the rigid nature of currently available surgical robots. These tools are based on the interaction of metal with soft tissues, which can cause unwarranted physical damage and jeopardize patients. There is a major need in the field for the production of safer medical devices made of compliant materials.

Soft robotics is a sub-field of robotics, which refers to constructing robots from highly compliant materials, similar to those found in living organisms. Organisms, such as Echinoderms (starfish, sea urchins) and Cnidarians (jellyfish) are ancient and relatively simple organisms, capable of movement beyond the reach of even the most advanced hard-robotic systems. Soft robotics draws heavily from the way these living organisms move and adapt to their physical surroundings. Unlike robots built from rigid materials, soft robots allow for increased flexibility and adaptability for accomplishing tasks while simultaneously decreasing risks for humans. These characteristics make soft robots highly desirable in the field of medicine.

The subject matter disclosed herein relates to a soft robotic device, which includes a first layer and a second layer bonded together. One or more of the layers may consist of extensible thermoplastic thermoelastic material. In one embodiment, one of the layers might be of a relatively stiffer, inextensible material compared to the other layers. The first and second layers may be directly bonded to each other or they may be bonded through one or more intervening layers. Additionally, the soft robotic device disclosed herein, can have an initial conformation in which there is negligible, low-volume in the interior of the device. The low-volume initial conformation enables the device to fit within spaces of small diameters such as catheters. In one embodiment, soft robotic devices also include a network that can be located in between the first and the second layers or any of the layers included in the device. This network can be pressurized in order to actuate the soft robotic device with a pneumonic mechanism facilitate a transition of the soft robotic device to from a flat, low-volume or zero-volume conformation to an extended or actuated conformation.

In one embodiment, the soft robotic device can be a bending device, a rotary device, a robotic swimmer, or a gripping device, which can be utilized in performing mechanical tasks such as moving objects in space. In another embodiment, the soft robotic device can be a heart valve or a stent and be utilized in the field of medical devices.

The subject method disclosed herein also relates to a laser welding method for constructing a soft robotic device. The method includes heat-pressing two or more layers together. In an embodiment of the laser welding method, the layers are polyurethane films. The method also includes laser welding a desired pattern from the heat-pressed layers.

The subject method disclosed herein further relates to a thermobonding method for constructing a soft robotic device. The method includes cutting a layer into a pattern. In an embodiment of the thermobonding method, the layer is water-soluble. The method also includes heat-pressing the layer between two or more external layers. In an embodiment, the external layers are polyurethane films. The method further includes dissolving the initial internal layer and cutting along seams, which formed following heat-pressing.

Soft robotic devices are based on cephalopods: animals without a skeleton, like octopus and squid. They mimic the movements of the cephalous by pressurizing a soft device having embedded channels. Soft robotics can be actuated using pneumatic pressure to cause the robot to undergo a range of motions. The basic soft robotic actuator includes an extensible channel or bladder that expands against a stiffer or less extensible backing. Soft robotic devices utilize soft materials, such as soft elastomer, or flexible materials, such as papers and a nitrile. Soft robotic systems can provide a complex range of motions when different parts of the system are pressurized independently or in sequence. The soft robotic devices can be integrated into subject-specific, anatomically-guided shapes that would optimize access while increasing dexterity for micromanipulation in an era of increasingly complex percutaneous interventions.

Thermoplastic materials are polymers, which can become pliable or moldable when heated above a specific temperature and solidify upon cooling. Most thermoplastics have a high molecular weight and melt into a molten state relatively quickly. Thermoplastic materials have long polymer chains linked through intermolecular forces such as van der Waals forces, forming linear or branched structures. With increased temperatures, these intermolecular forces weaken rapidly, yielding a viscous liquid. Thus, thermoplastics may be reshaped by heating and are typically used to produce parts. However, each particular thermoplastic exhibits different physical properties, making it critical to select the right material for the application at hand. Examples of thermoplastic materials include but are not limited to polyurethane, high-pressure polyethylene, low-pressure polyethylene elastic, polystyrene, polyamide, and polyvinyl chloride (PVC).

The subject matter disclosed herein relates to a soft robotic device, which can have multiple conformations including an unactuated or non-expanded conformation, an actuated or extended/inflated conformation, and an initial conformation in which there is negligible volume in the interior of the device. This initial conformation can be referred to as a "low-volume" or a "zero-volume" initial conformation of the soft robotic device. The "low-volume" initial conformation may also refer to a soft robotic device, in which there is virtually zero-volume or zero-volume visually present in the interior of the device. In a low-volume conformation, the sides of the soft robotic device may be collapsed onto each other. For example, the soft robotic device can be substantially planar in its low-volume initial conformation. A low-volume initial conformation device may require an additional step of collapsing and expanding such as rolling it up and then unrolling it before actuation. The low-volume initial conformation enables the device to fit within spaces of small diameters such as catheters. For example, the low-volume initial conformation of the device can be a rolled up conformation that allows the device to be inserted into a catheter. These soft robotic devices may be scalable in size depending on purpose of use and can be utilized in a number of fields including but not limited to soft robotics engineering to facilitate directional movement of robots, minimally invasive surgery to control the movement of robotic arms or gripping devices, and trans-catheter delivery of medical devices or tissues such as prosthetic heart valve delivery through a catheter system. In an embodiment, the thickness of the soft robotic device is less than 70 μm. In another embodiment, the thickness may exceed 70 μm.

The soft robotic device includes a first layer and a second layer bonded together. One or more of the layers may consist of extensible thermoplastic material such as polyurethane or any other polymer that may be suitable for the purpose of expanding under applied pressure. In one embodiment, at least one of the thermoplastic layers might be made of a thermoelastic material. Thermoelastic materials change elasticity with changes in temperature, such that when thermal energy is added to an elastic material, the material expands. Thermoplastic polyurethane is a type of a thermoelastic material. Thermoelastic materials also include rubber-like polymers. In one embodiment, one of the layers might be of a relatively stiffer, inextensible material. In another embodiment, one or more reinforcing layers can also be included, such as a paper or mesh fabric. The first and second layers may be directly bonded to each other or they may be bonded through one or more intervening layers.

In one embodiment, all layers included in the soft robotic device may be of the same thickness. In other embodiments one or more of the layers may have a variable thickness along their length. One or more of the layers may be thicker or thinner than one or more of the other layers along their entire length. Additionally, soft robotic devices may utilize differences in layer thicknesses to create the differences in extensibility used for actuation. For example, a thicker layer might not expand upon pressurization to the same extent as a thinner layer would. The difference in expansion can create curvatures in the design of the actuated soft robotic device.

Soft robotic devices can also include a network that is located in between the first and the second layers or in either of the layers, or in a third central layer positioned between the first and second layers. In an embodiment, the network is pneumatic, meaning it contains and/or is operated by air or another gas that is under pressure. The pneumatic network can be pressurized in order to actuate the soft robotic device. In another embodiment, the network may be actuated by utilizing a fluidic system, may be electric, or optical. Pressurizing the network allows for the soft robotic device to transition from a relatively flat, low-volume or zero-volume conformation to an extended or actuated conformation. The network may be pressurized using any suitable pressurizing device or pump. In an embodiment, soft robotic devices made from a thermoplastic material can return back to an initial conformation after pressurization. In one embodiment, plastic materials that cannot undergo an elastic recovery may be used for single-actuation soft robotic devices. In one embodiment, wherein one or more of the layers is made of a relatively inextensible material compared to the other layers in the soft robotic device, the inextensible layer may require a greater pressurizing force for expansion and extension of the inextensible layer may not occur even after pressurizing the network.

Figure 25:
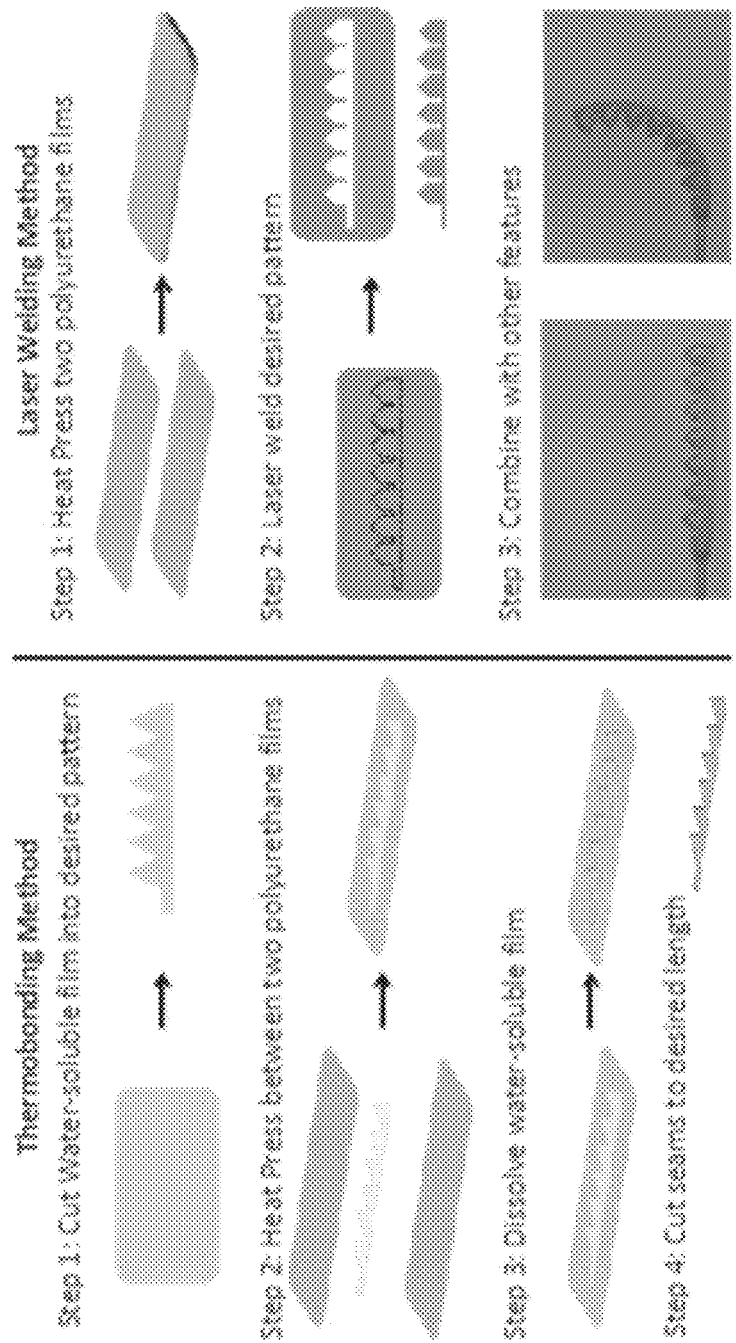
FIG. 25 depicts a schematic representation of two methods for constructing low-volume thin soft robotic devices. Thermobonding method is shown on the left. Laser welding method is shown on the right.

In one embodiment of the subject matter disclosed herein, a thermobonding method for constructing a soft robotic device may be the method of choice in order to minimize thickness of the device. As described in FIG. 25 (left), this method includes inserting a pre-cut layer pattern between two or more external layers and directly sealing the layers using a heat press. In an embodiment, the external layers are thermoplastic films. The layer pattern defines a pneumatic network between the two or more external layers. In one embodiment, the pre-cut layer has a higher transition temperature compared to other layers included in the device in order to prevent bending. In one embodiment, the pre-cut layer is made from a material that can be dissolved after thermal bonding, for example water-soluble films are used for more effective actuation of the pneumonic network. The thermobonding method may result in a more desirable or higher burst strength of the soft robotic device. Furthermore, thermoplastic materials can become pliable or moldable above a specific temperature and solidify upon cooling.

In some embodiments the subject matter disclosed herein relates to a laser welding method for constructing soft robotic devices. Laser welding using a $CO_2$ laser provides a cheap and rapid method for soft robotic device construction. As described in FIG. 25 (right) this method includes forming of the soft robotic device by applying heat, pressure, or both to sheets of thermoplastic material. The laser welding method further includes laser heating or welding applied to those areas where bonding is desired. In one embodiment, heating and/or pressure can be applied by physical contact with a hot surface, or by laser heating or any conventional methods. In those areas where heat is applied, the thermoplastic materials can soften and bond together. The soft robotic device can then be cooled in order to resolidify the thermoplastic materials and to form a solid bond. In some embodiments, additional layers can be bonded to the laser welded layers in order to achieve solid impermeable layers since the laser welding method may cut the layers it seals them, leaving holes in the device.

Figures 26A, 26B, 26C, 26D:
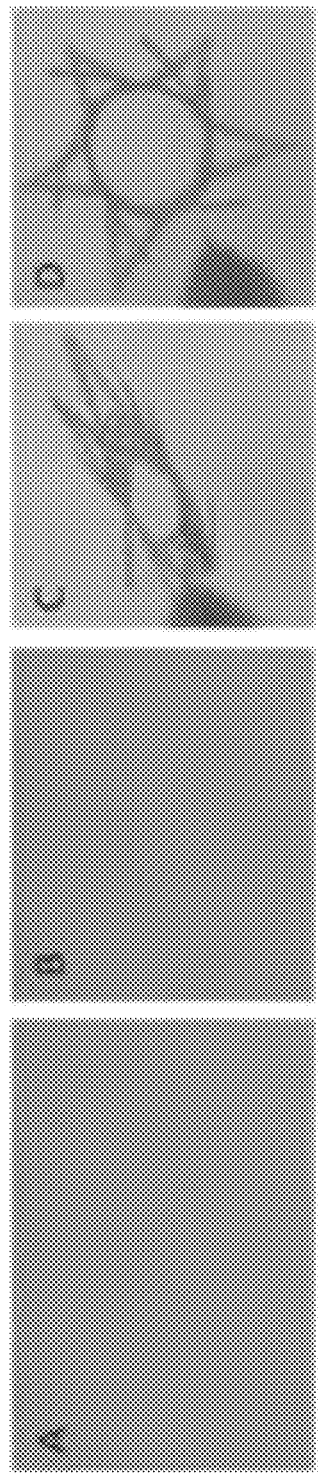
FIGS. 26A-26D show different conformations of two soft robotic devices.

FIGS. 26A-26D depict different conformations for two embodiments of a soft robotic device. FIG. 26A shows an unactuated, low-volume initial conformation of a bending device with a flat geometry. FIG. 26B shows an actuated conformation of a bending device with a flat geometry. Following pressurization, one or more layers can expand to a higher degree compared to one of more of the other layers allowing for the bent shape of the actuated conformation. FIG. 26C shows an unactuated, low-volume initial conformation of a soft robotic device with complex geometry. FIG. 26D shows an actuated conformation soft robotic device with complex geometry.

FIG. 27 illustrates actuation of a soft robotic device, a prototype heart valve according to one or more embodiments. In this embodiment, at rest (left), the soft robotic device is rolled up in low-volume initial conformation. This conformation allows for the prototype heart valve to fit into spaces with small diameters such as catheters and other medical devices. Once unrolled, the prototype heart valve assumes an unactuated conformation such that the layers of the device remain flat (center). Once pressurized, the pneumatic network expands and bows outward in an actuated conformation, causing "fingers" to bend away (right).

Soft robotic devices can be made of soft and compliant materials such as polymers-metal composites, elastomers, and hydrogels. These soft robotic devices operate based on pneumatic, electrical, chemical, and optical actuation mechanisms. Soft robotic devices with pneumatic actuation mechanisms include a series of interconnected inflatable chambers, which can be made from elastomers, fabrics, or a combination of both types of these materials. The geometry and material properties of these chambers dictate the motion of the device, upon actuation. Fabrication can be achieved by rapid casting with two-part mixtures of liquid elastomer precursors into 3D printed molds with manually embedded fabrics. Although this process is relatively simple compared to other manufacturing methods for soft and hard robotic devices, the full process of creating a new design for an actuator can take several hours, since it requires the following steps: i) design geometry in CAD, ii) 3D print mold, iii) prepare and degas elastomer, iv) pour and bake elastomer (with or without fabric layers), and v) de-mold and bond parts of an actuator. Furthermore, fabricating thin (<0.5 mm) soft robotic devices can be particularly challenging since currently typical 3D printed parts do not provide sufficient resolution, and de-molding such thin features can be difficult. Thin soft robotic devices can be constructed by means of soft lithographic techniques, photolithography, and micro-casting. Alternatively, thin soft robotic devices can be constructed using membrane micro-embossing by excimer laser ablation (MeME-X). These methods, although effective, are laborious and time-consuming, limiting their adoption to a broader community. A simple fabrication method for the development of small-scale soft robotic devices with a pneumatic actuation mechanism can be based on dip-coating of cylindrical templates. A drawback to the simplicity of this method, however, is that only a limited number of designs can be fabricated easily. Therefore, a simple yet versatile method that allows the production of thin actuators with arbitrary features is desirable for soft robotics applications.

The subject matter disclosed herein also relates to a simple and effective laser welding method for rapid fabrication of thin soft robotic devices. In an embodiment, the thin soft robotic devices may utilize a pneumatic mechanism of actuation. In another embodiment, the soft robotic devices can utilize an electrical, chemical or optical actuation mechanism or any combination of these mechanisms or any other suitable mechanism that would lead to activation of the soft robotic device. The method includes simultaneously cutting and laser welding a stack of thin films made of thermoplastic polyurethane. The method may further include utilizing inexpensive and commercially available materials and tools for constructing soft robotic devices. In an embodiment, the thickness of the soft robotic devices is 70 µm or less. In another embodiment the thickness can be more than 70 µm. In an embodiment of the laser welding method embodiment, several different types of thin soft robotic devices can be constructed, whose motions occur in-plane and out-of-plane. The soft robotic devices constructed via the laser welding method can also include grippers for pick and place applications and a swimming soft robot. The trajectory of these soft robotic devices can be modeled using Finite Element Method (FEM).

Figures 28A, 28B, 28C:
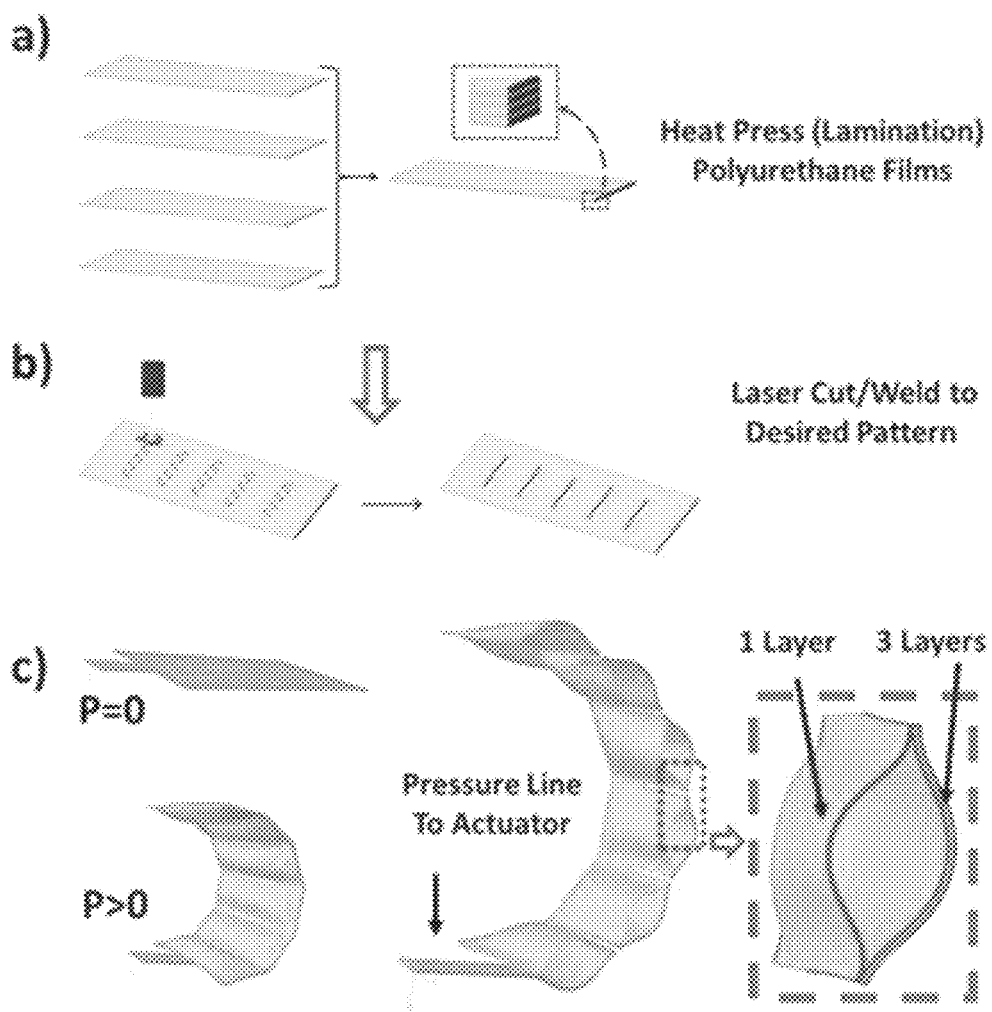
FIGS. 28A-28C depict a schematic representation of the fabrication process using a laser welding method.

The laser welding method for constructing soft robotic devices includes laminating layers by means of a heat press as illustrated in FIG. 28A, which ensures that polyurethane layers are flat and in conformal contact without creating a permanent bond between the layers. The layers may be thermoplastic polyurethane films. The method further includes cutting out a desired shape of the soft robotic device under constructing using a laser-cutting machine. The laminated layers can also be welded by the laser-cutting machine. In an embodiment of the laser welding method embodiment, a single pass of a laser beam can both cut and bond the edges of the layers of the soft robotic device, forming a sealed soft robotic device as shown in FIG. 28B. In an embodiment of the laser welding method, the soft robotic device under construction can be functional immediately after the cutting process. In one embodiment of this method, a two-layered soft robotic device can be constructed that can hold ~10 psi for a square geometry with a size of 20×20 mm. In another embodiment, the soft robotic device constructed via the laser welding method can hold more or less than 10 psi for any square geometry larger or smaller than 20×20 mm. In some embodiments, the two layers bonded as described above can form a single actuator. In some embodiments, additional actuators (e.g., formed from additional layers) can be laminated to the first actuator, such that the soft robotic device includes more than one actuator.

Figures 29A, 29B, 29C:
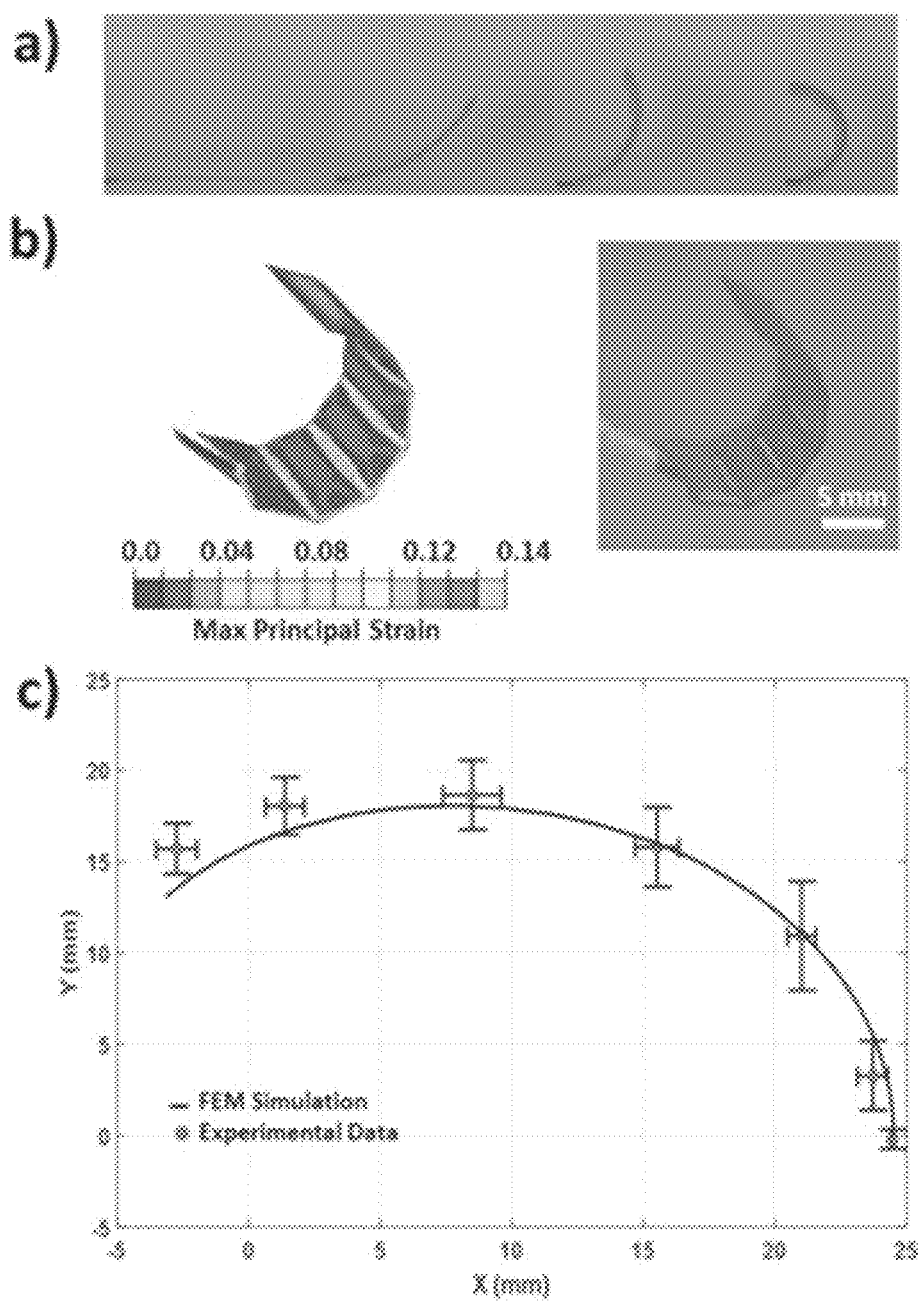
FIGS. 29A-29C elaborate on the bending motion of a soft robotic device.

In one embodiment of the subject matter disclosed herein, the soft robotic device is a bending soft robotic device. The bending device can be made by utilizing an asymmetrical profile achieved by making one side of the soft robotic device thicker or less compliant than the other side. This allows for the bending device to bend upon inflation due to asymmetric stiffness and strain on the sides as demonstrated in FIG. 28C showing a 4-layer soft robotic device (Actuator Type I), with in-plane symmetry. The inflated soft robotic device is bounded by single and triple layered films as shown in FIG. 28C, which leads to the asymmetry across the actuator. The bending motion of the bending device embodiment is shown in FIG. 29A. FIG. 29B shows a heat-map of maximum principle strain in different portions of the bending device while in ultimate bent configuration. FIG. 29C shows a comparison between the simulated and experimental lateral displacements of a thin soft robotic device using FEM simulation.

Figures 30A, 30B, 30C, 30D:
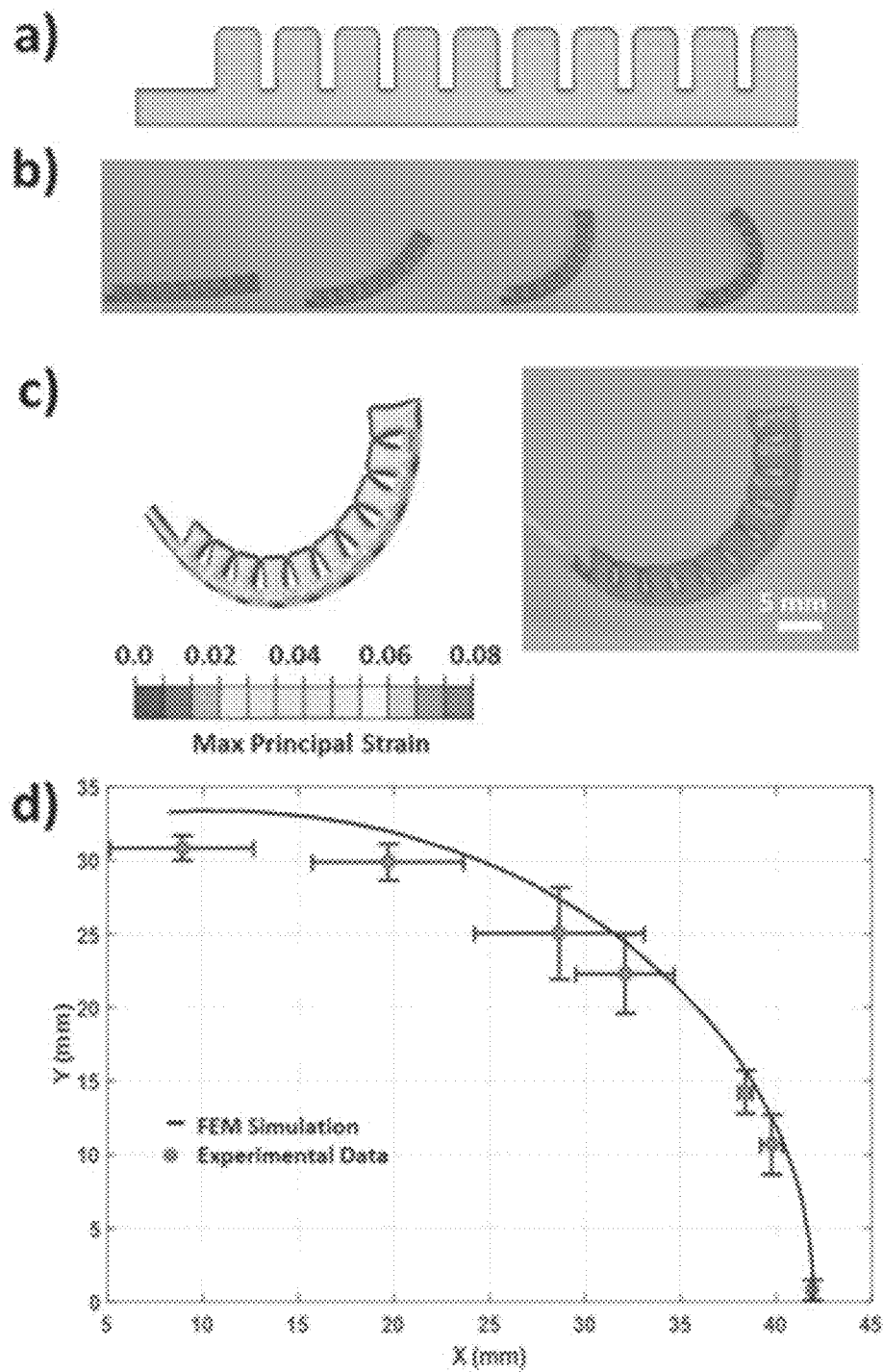
FIGS. 30A-30D depict a soft robotic device of type II.

In one embodiment, an asymmetrical profile for a soft robotic device can be achieved by applying specific geometrical construction. For example, FIG. 30A depicts a soft robotic device with a geometry consisting of several pockets, which are connected only on one side (soft robotic device of Type II). In one embodiment, the motion of a soft robotic device of Type II can occurs in-plane as demonstrated in FIG. 30B.

The motions for both Type I and Type II soft robotic devices with in- and out-of-plane bending can be accurately simulated using a Finite Element Method (FEM) as shown in FIG. 30C as well as FIGS. 30C and 30D. In an embodiment of the bending device embodiment, the level of strain for bending devices of Type I and Type II is less than 15%. Furthermore, the majority of the soft robotic device may undergo even lower levels of strain, less than 5%. In comparison, conventional soft robotic devices might require more than 50% strain. In another embodiment, the level of strain for bending devices of Type I and Type II can be more than 15%.

In one embodiment, the mechanism of bending for these soft robotic devices is primarily dependent on folding of the walls of the chambers, which is fundamentally different than most soft robotic devices, which rely on large levels of strain of the chamber walls. As shown in FIGS. 30C and 30D, soft robotic devices of Type II can have a lower and more uniform strain distribution for nearly the same degree of bending.

Figure 35:
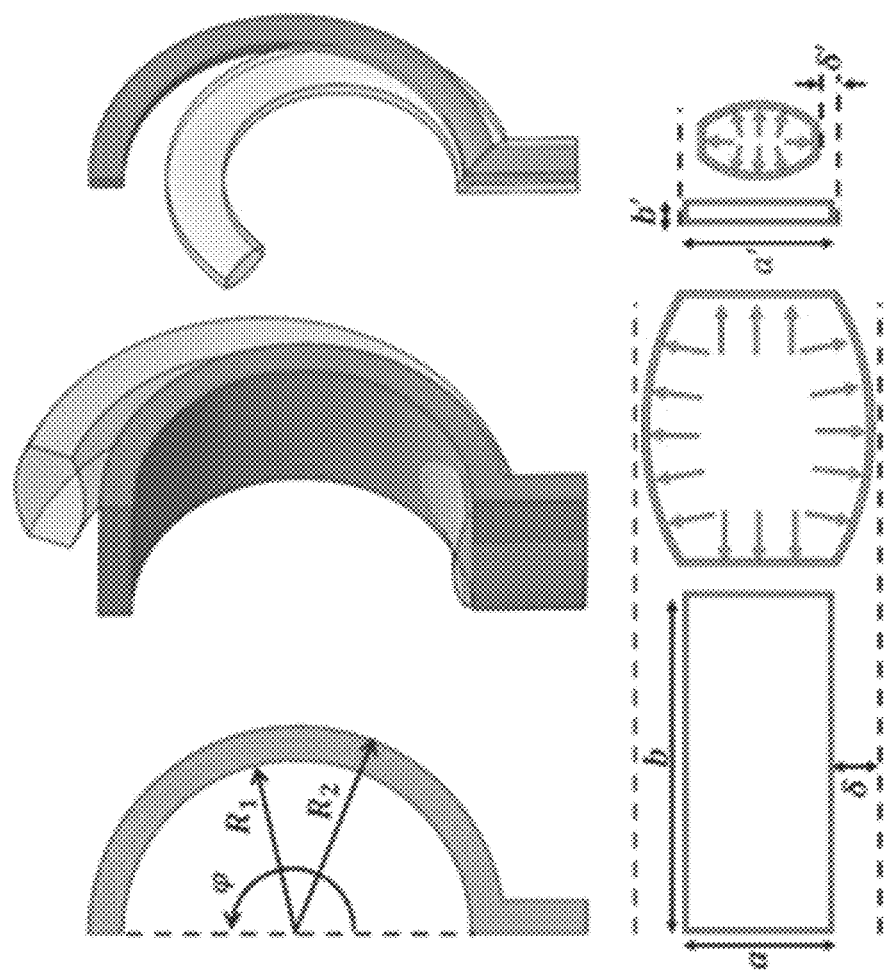
FIG. 35 shows a comparison between the bourdon tube and the soft thin rotary soft robotic devices.

In one embodiment of the laser welding method embodiment, design of functional soft robotic devices with complex motions such as a rotary or a linear device can be achieved by changing the design of the CAD file used to laser cut the devices. In one embodiment of the subject matter disclosed herein, the soft robotic device is a rotary device. Designing a rotary device consists of generating a curved tube with a flattened cross-sectional area. The cross section can be compared to a Bourdon tube, which is rectangular where its longer side is parallel to the normal of the plain of the curved tube. Upon inflation, the cross section can tend towards a nearly round shape causing the tube to straighten out. In one embodiment, relating the tip displacement to the pressure inside the tube can be used as a pressure sensor. A rotary device can also be utilized as a hydraulic soft robotic device for Micro-Electro-Mechanical Systems (MEMS) or in soft surgical robots. In some embodiments, a soft robotic device can be configured to actuate in a combination of rotary, linear, and or other motion patterns. For example, the pneumatic network contained within a device (e.g., one or more channels or tubes) can be arranged in a pattern such that, when inflated, the device can exhibit both rotary motion and linear motion, or any other combination of types of actuation. In some embodiments, the cross section of the thin soft robotic device can be flattened in-plane whereas that of the Bourdon tube is flattened out-of-plane as shown in FIG. 35. Upon inflation, the thin rotary soft robotic device can curl up whereas the Bourdon tube straightens as exemplified in FIG. 35.

Figures 31A, 31B, 31C:
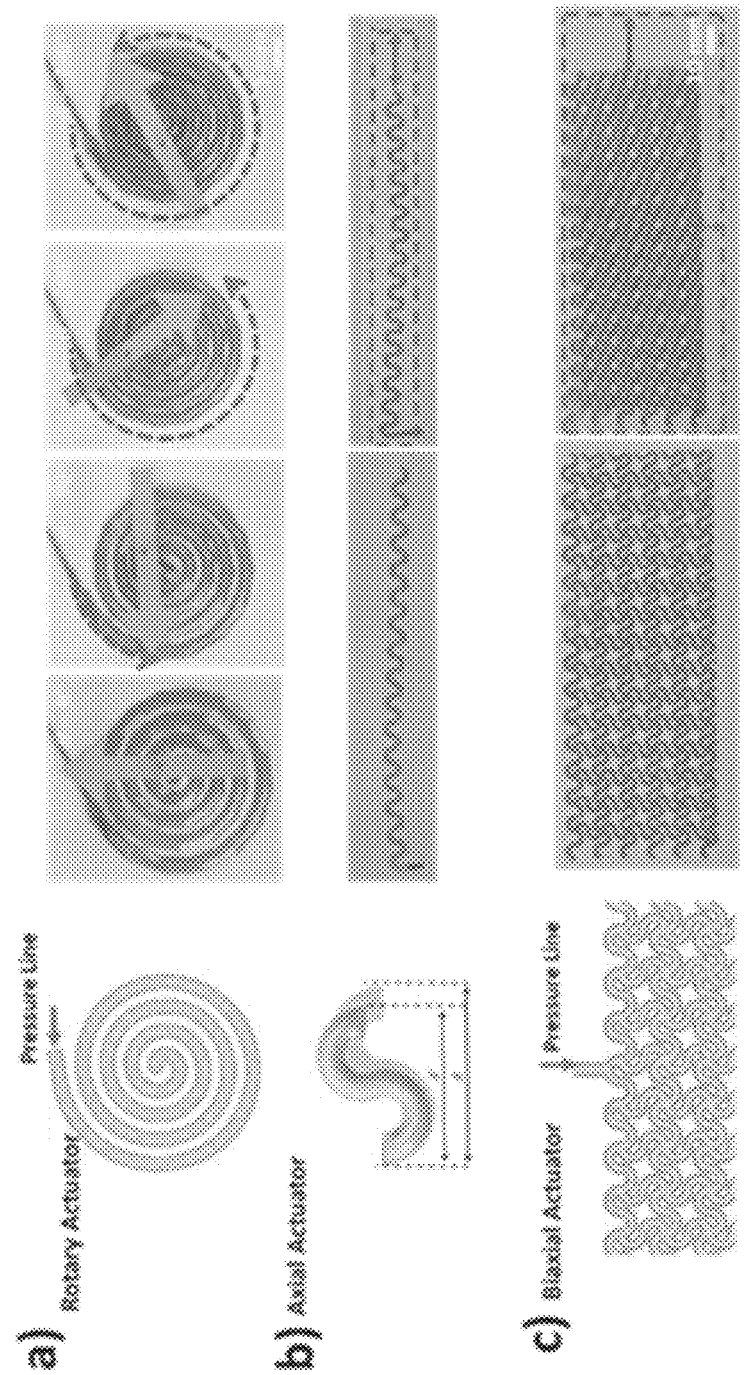
FIGS. 31A-31C depict a schematics and prototypes of two soft robotic devices.

FIG. 31A demonstrates how a spiral curve can act as a rotary device. In an embodiment, upon inflation the spiral curve can rotate up to 300° at the pressure of 4.5 psi. In another embodiment, the rotary device can rotate more than 300° at pressures less than or more than 4.5 psi. A curved tube design can be further applied to produce axial and biaxial soft robotic devices by defining a proper unit cell. For instance, axial soft robotic devices can be developed from combination of semi-circle curves, with an S-shaped unit cell as shown in FIG. 31B. This unit cell is known as a horseshoe serpentine structure and can be used for stretchable electronic applications. Each semi-circle curve can curl up upon inflation and thus the overall length of an S-shaped unit cell can be decrease. In one embodiment, changing the shape and total number of unit cells can modify the overall displacement of the linear soft robotic device. For instance, a linear device with 15 unit cells might generate approximately 20 mm displacement at a pressure of 7 psi, suggesting each unit cell displaces 1.3 mm as shown in FIG. 31B. The developed axial soft robotic device can be extended to a biaxial soft robotic device as shown in FIG. 31C, by extending the array of unit cells in 2D. The S-shaped unit cell can be rotated 90° and joined to itself to create the unit cell of the biaxial actuator. The overall displacement in each axis can be linearly proportional to the number of S-shaped unit cells used in that direction. For example, a biaxial actuator as shown in FIG. 31C, which has 15 and 6 unit cells along x and y directions, respectively, shrinks by 20 and 7.4 mm at a pressure of 7 psi.

Figures 32A, 32B, 32C:
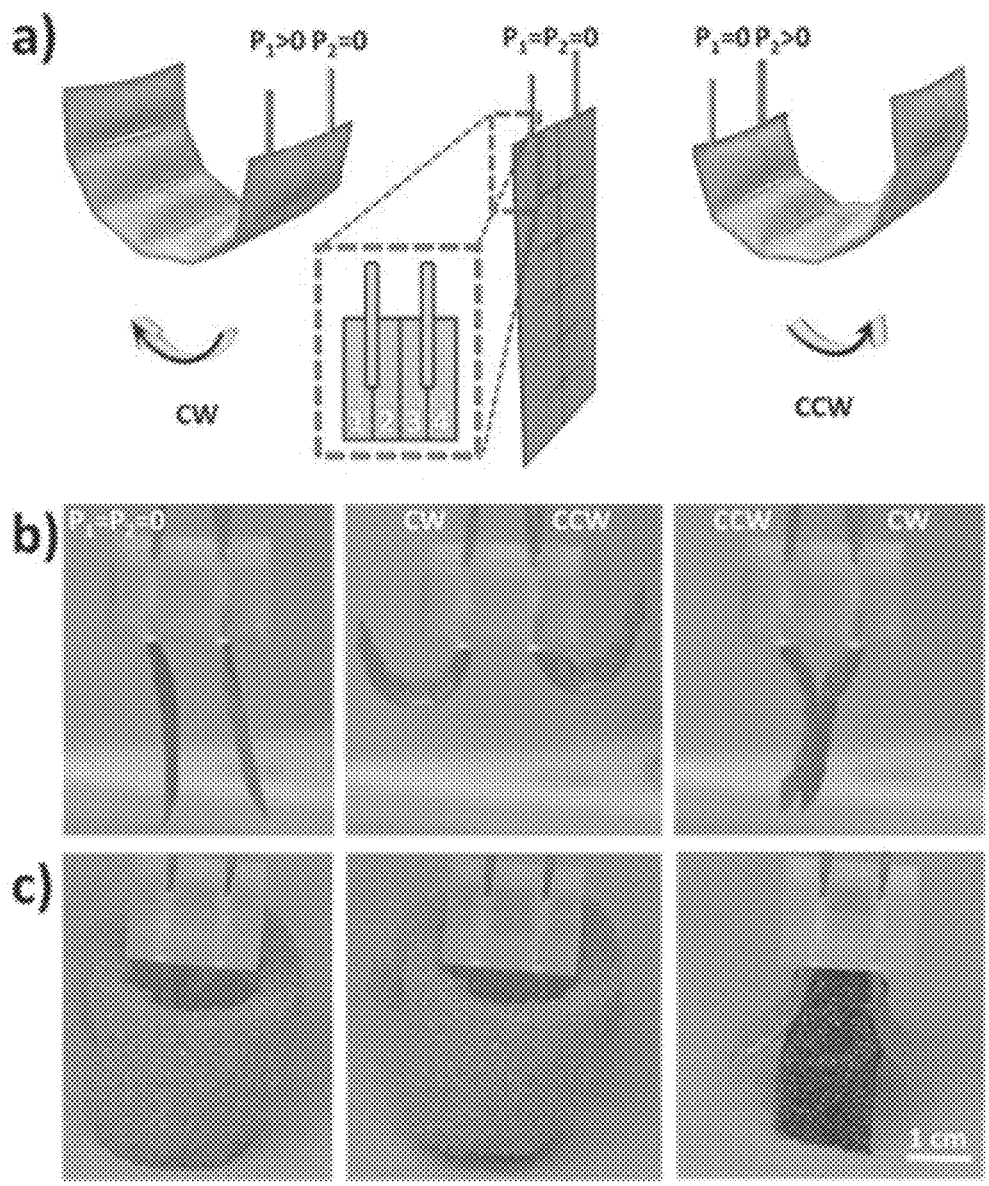
FIGS. 32A-32C show a bi-directional soft robotic device.

In one embodiment, a soft robotic device of Type I can function as a bi-directional device by being inflated between its different layers. Specifically, inflating the chamber bounded by layers 1 and 2 can result in a clockwise motion, and inflating the chamber bounded by layers 3 and 4 can result in a counter clock wise motion as shown in FIG. 32A. In another embodiment, the soft robotic device is a soft gripper. A soft gripper can be constructed by combining two bi-directional soft robotic devices with a robotic arm. In an embodiment of the soft gripper embodiment, the soft gripper is capable of performing pick and place tasks. FIGS. 32B and 32C show the unactuated (left), actuated open (center), and actuated closed (right) conformations of the soft gripper, as well as images taken during the pick-and-place operations for various objects. In an embodiment of the soft gripper embodiment, the soft gripper can lift an object with a mass of 2.66 g at a pressure of 41 kPa (6 psi) in its open conformation. In another embodiment, the soft gripper can lift an object with a mass of more or less than 2.66 g at pressures below or above 41 kPa (6 psi). Furthermore, in an embodiment of the soft gripper, the soft gripper can weigh as little as 0.098 g and can lift an object 30 times heavier than its own weight. In another embodiment the soft gripper can weight more or less than 0.098 g and lift an object more or less than 30 times its own weight.

Figures 33A, 33B, 33C, 33D:
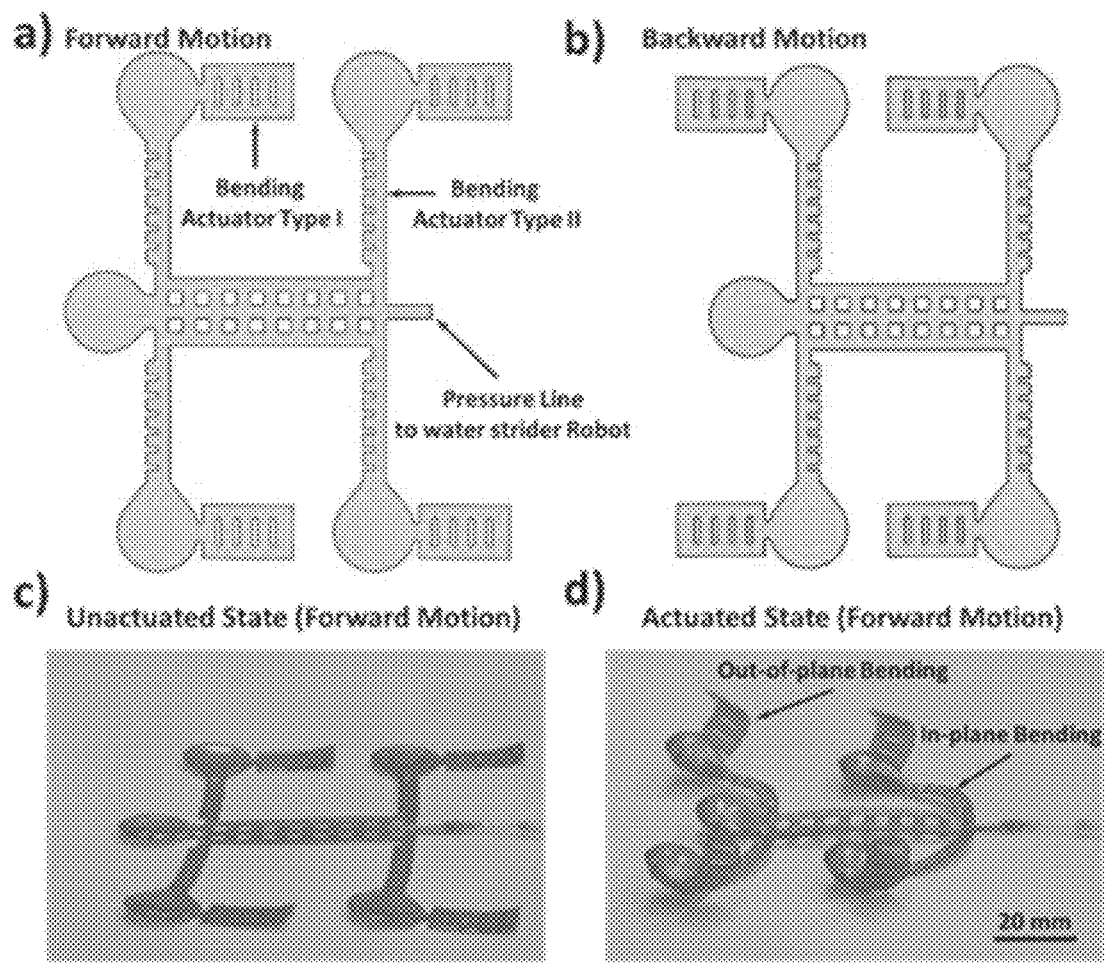
FIGS. 33A-33D depict a schematic design of a water strider soft robotic device for generating forward in FIG. 33A and backward in FIG. 33B swimming motions. Unactuated and actuated conformations in forward motion mode are shown in FIG. 9C and FIG. 33D, respectively.

In one embodiment, the soft robotic device may be a four-arm swimming robotic device referred to as a robotic swimmer hereafter. The CAD file can be directly fabricated into a robotic swimmer in one step without requiring any assembly. Each arm can have two degrees of freedom (DOF) and consist of two bending devices. The first soft robotic device can be of Type II with in-plane bending motion, functions as the arm of the swimmer, and the second soft robotic device can be of Type I with out-of-plane bending motion, acting as a fin as shown in FIG. 33A. The palm of this robotic swimmer can be a circular balloon that connects the fin to its arm. In an embodiment, the palm can inflate more than the rest of the arm, due to its large and circular surface area, serving as the point of contact of the robotic swimmer to the water ensuring the arm stays level with the surface of the water during actuation. In another embodiment, the palm can inflate as much as or less than the rest of the arm. In one aspect, the robotic swimmer can be as light as 0.62 g allowing it to float in both its actuated and unactuated conformations. In another aspect, the robotic swimmer can weigh more than 0.62 g. The robotic swimmer can be powered by a mini compressor or any other pressure source and can be controlled by a microcontroller that controls two three-way valves. In one aspect, as shown in FIG. 33B the robotic swimmer includes mirrored soft robotic devices allowing the robotic swimmer to move in the opposite direction. FIGS. 33C and 33D show the unactuated (left) and actuated (right) configurations of the forward swimming robotic swimmer positioned upside down (i.e., laying on its back) to better visualize its motion.

Figures 34A, 34B, 34C, 34D:
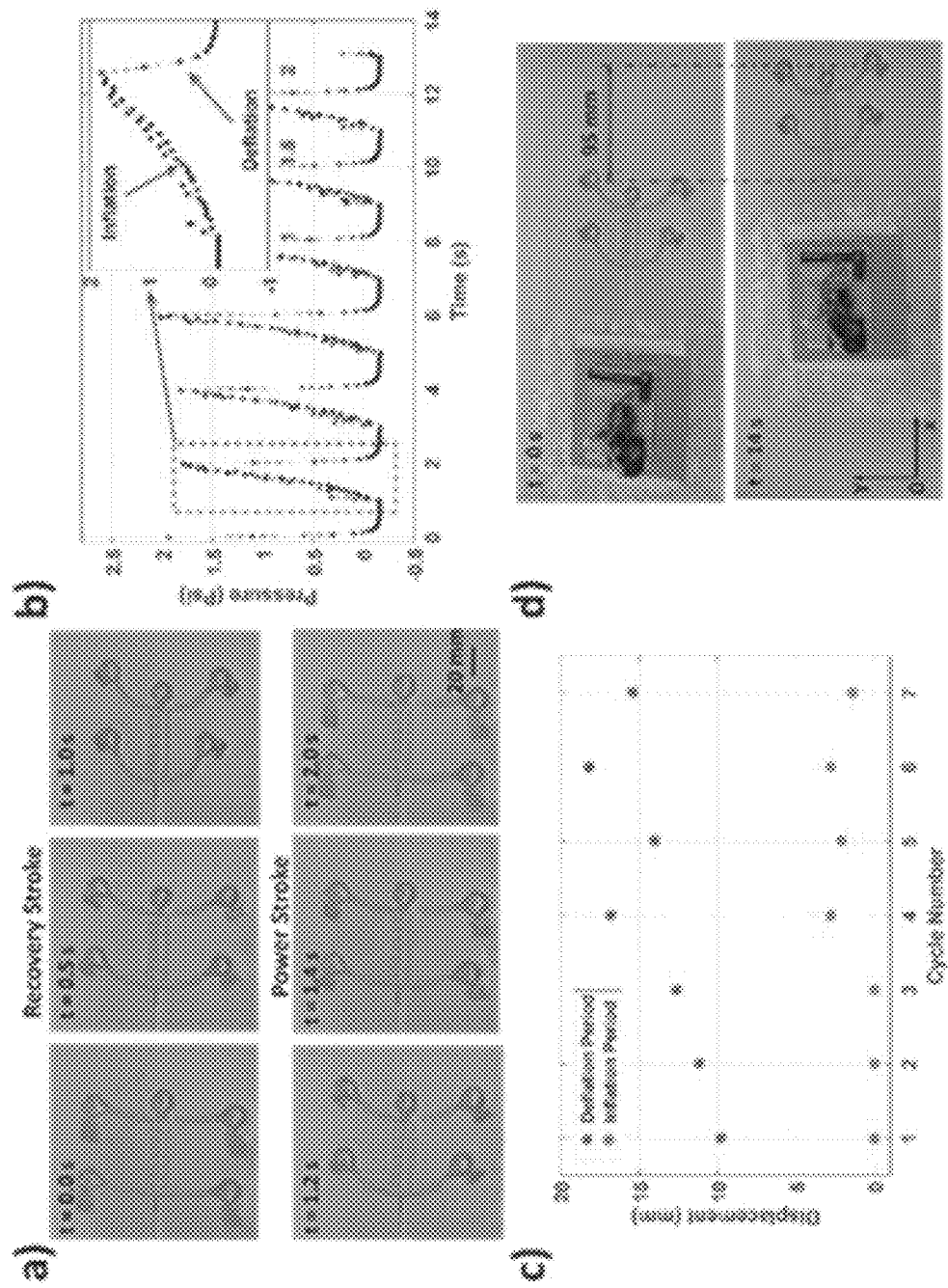
FIGS. 34A-34D depict a water strider soft robotic device.

FIG. 34A shows a sequence of images depicting the forward swimming motion of the robotic swimmer for a single cycle, where a cycle consists of an inflation and deflation phases. In an embodiment of the robotic swimmer embodiment, the arms of the robotic swimmer bend gradually and produce little thrust. That can be achieved with a low flow rate of the compressor. In an embodiment, the flow rate of the compressor is 250 ml/min or less. In another embodiment, the compressor flow rate can be more than 250 ml/min. In an embodiment of the robotic swimmer embodiment, during the deflation phase the arms are allowed to return to their original position quickly, creating a relatively greater thrust than during inflation phase. Therefore, the inflation phase can serve as the recovery stroke, and the deflation phase can serve as the power stroke for this swimming robotic device. FIG. 34B shows the pressure inside the robotic device during the inflation and deflation phases. The graph shows that the inflation can occur in a near linear fashion, while the deflation can occur exponentially. FIG. 34C shows the displacement of the robotic device for the deflation and inflation phases over a series of seven cycles. Initially during the first three cycles, the robot can have a near zero movement during its inflation phase and a progressively increasing displacement during its deflation phase. In one embodiment, the average velocity of the robotic device can be 6.7 mm/s over the seven cycles as shown in FIG. 34D. In another embodiment, the robotic swimmer can have an average velocity above or below 6.7 mm/s. In an embodiment, the robotic swimmer can pull a load as heavy as 127 g, which is 204 times its own weight. In another embodiment, the robotic swimmer can pull any load heavier or lighter than 127 g.

Figure 36:
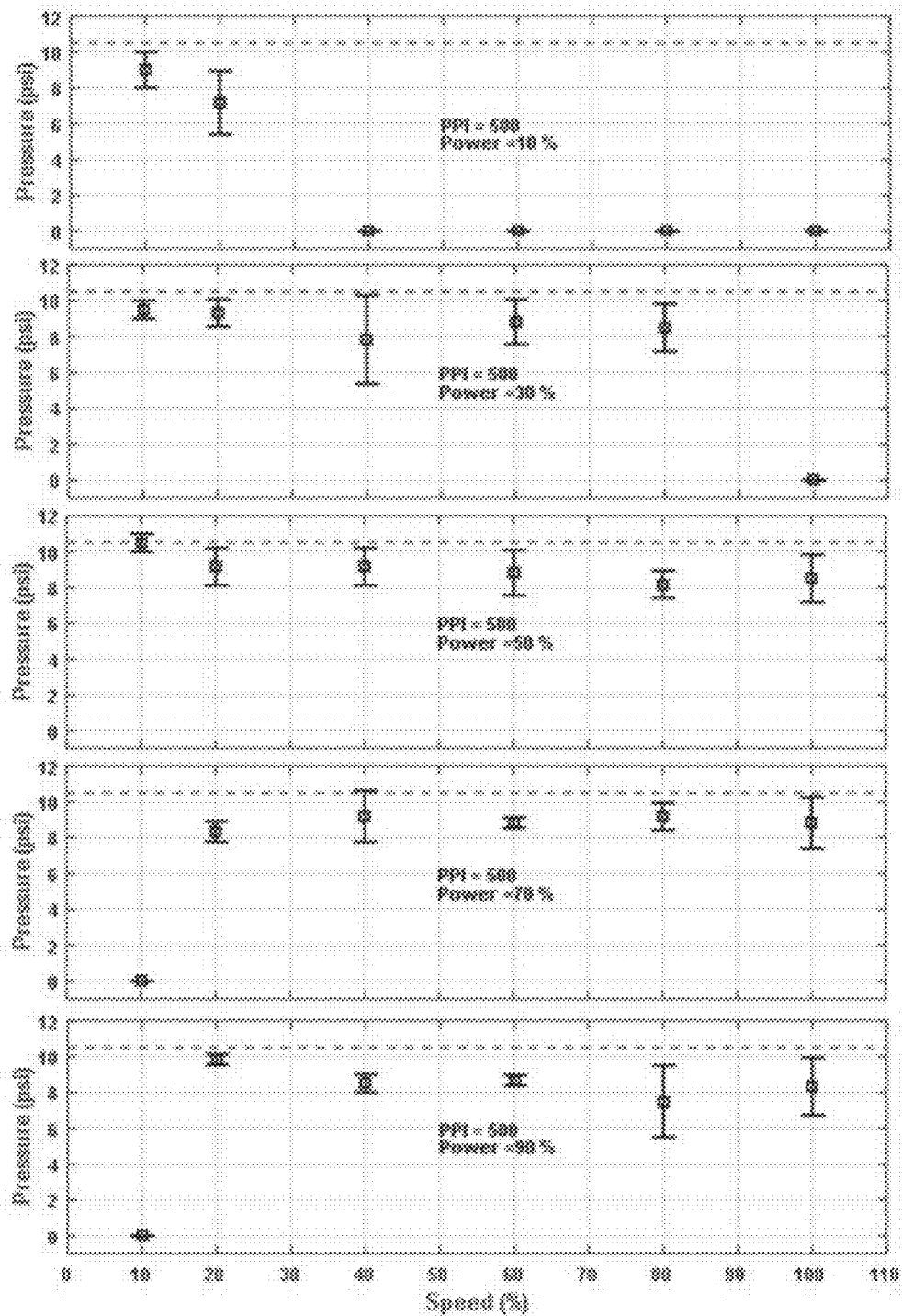
FIG. 36 shows a mean burst pressure of the balloon as a function of speed and power. The red dotted line refers to the maximum burst pressure of 10.5 psi achieved for all conditions.

In one aspect, two layers can be laminated and laser welded into square balloons. The average burst pressure of the balloons can be measured for any constant power ranging from 10% to 90% and the speed varied from 10% to 100% as shown in FIG. 36. In an embodiment, the balloons can be made with the power ranging between 30% and 90% and the speed ranging between 20% and 90%. Average burst pressure of 10.5 psi can occur in the case of 50% power and 10% speed.

Figures 37A, 37B:
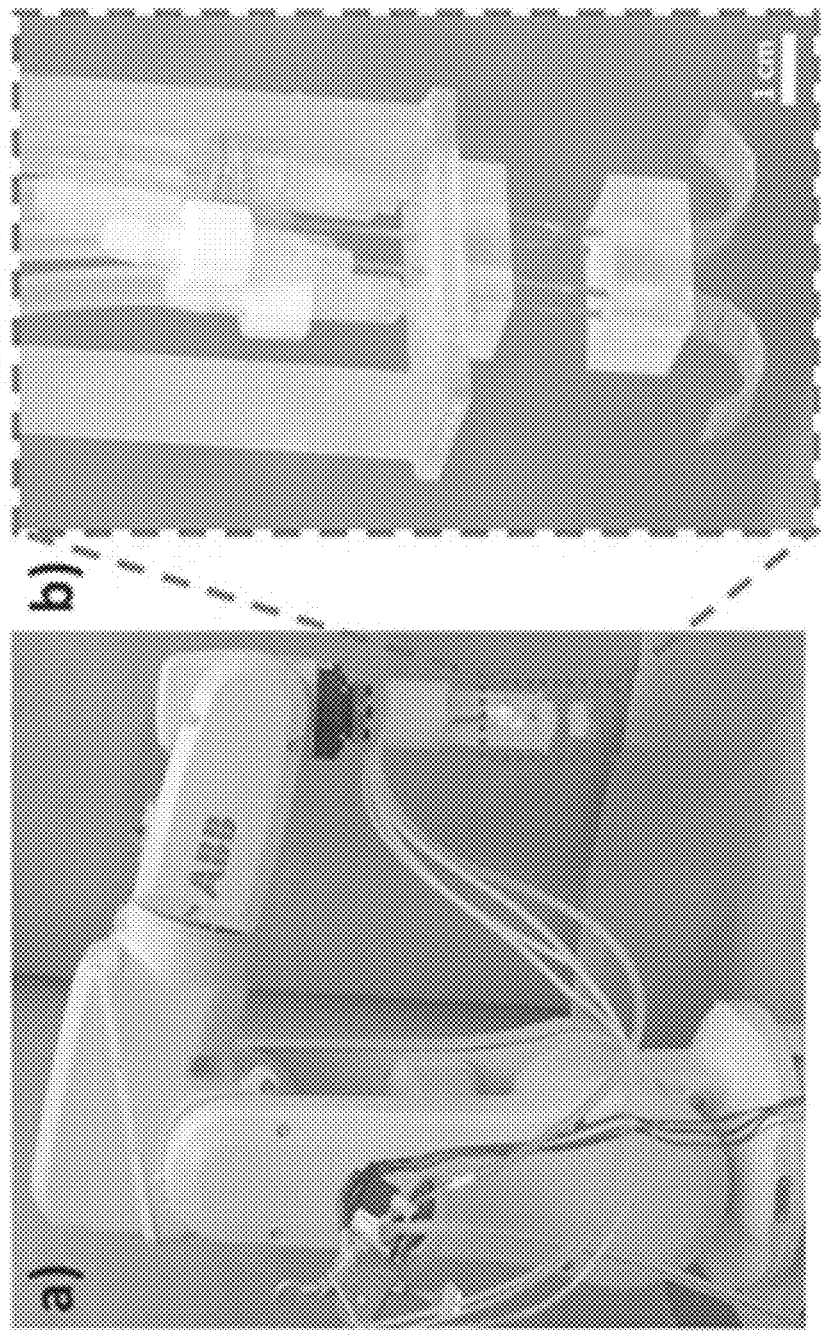
FIGS. 37A and 37B show a 6 DOF ABB (IRB120) robot arm, 3D printed adaptor and a soft robotic bidirectional gripper.

In one aspect of the robotic gripper utilized for the pick and place task, the robotic gripper can be attached to the an ABB robotic arm (6 DOF ABB, IRB120) by means of a 3D printed adaptor as shown in FIG. 37. The robotic gripper can further be controlled by means of four solenoid valves (VQ110U-5M) and can be actuated by four digital outputs of a robot control system. ABB RAPID programing language can be utilized to control both robot and its soft gripper robotic device. The ABB RAPID code used to both control the solenoid valves and the ABB robot arm includes:

```
"
MODULE Soft Robot
PERS tooldata Extruder:=[TRUE,[[0,0,190],[1,0,0,0]],[0.25,[0,0,1],[1,0,0,0],0,0,0]];
PERS wobjdata wobj_plate:=[FALSE,TRUE,"",[[300,0,0],[1,0,0,0]],[[0,0,0],[1,0,0,0]]];
CONST robtarget target:= [[28, 40,
200],[0,1,0,0],[0,0,0,0],[9E9,9E9,9E9,9E9,9E9,9E9]];
VAR num i:=1;
VAR num j:=2;
VAR num k;
VAR num s;
PROC main( )
i:=1;
TPErase;
MoveL
[[0,100,80],[0,1,0,0],[0,0,0,0],[9E9,9E9,9E9,9E9,9E9,9E9]],v50,fine,Extruder\WObj:=wobj_plate;
SetDO DO10_1,0;
SetDO DO10_2,1;!open
WaitTime 2.5;
!first obj
MoveL
[[0,100,10],[0,1,0,0],[0,0,0,0],[9E9,9E9,9E9,9E9,9E9,9E9]],v50,fine,Extruder\WObj:=wobj_plate;
SetDO DO10_2,0;
SetDO DO10_1,1;!keep
waittime 2.5;
MoveL
[[0,100,150],[0,1,0,0],[0,0,0,0],[9E9,9E9,9E9,9E9,9E9,9E9]],v50,fine,Extruder\WObj:=wobj_plate;
MoveL
[[0,300,150],[0,1,0,0],[0,0,0,0],[9E9,9E9,9E9,9E9,9E9,9E9]],v50,fine,Extruder\WObj:=wobj_plate;
MoveL
[[0,300,110],[0,1,0,0],[0,0,0,0],[9E9,9E9,9E9,9E9,9E9,9E9]],v50,fine,Extruder\WObj:=wobj_plate;
WaitTime 0.5;
SetDO DO10_1,0;
SetDO DO10_2,1;!drop
WaitTime 1;
MoveL
[[0,300,150],[0,1,0,0],[0,0,0,0],[9E9,9E9,9E9,9E9,9E9,9E9]],v50,fine,Extruder\WObj:=wobj_plate;
!2nd obj
MoveL
[[0,30,80],[0,1,0,0],[0,0,0,0],[9E9,9E9,9E9,9E9,9E9,9E9]],v50,fine,Extruder\WObj:=wobj_plate;
SetDO DO10_2,0;
SetDO DO10_1,1;!close
WaitTime 2;
MoveL
[[0,30,10],[0,1,0,0],[0,0,0,0],[9E9,9E9,9E9,9E9,9E9,9E9]],v50,fine,Extruder\WObj:=wobj_plate;
WaitTime 0.5;
SetDO DO10_1,0;
```

```
SetDO DO10_2,1;!keep
WaitTime 2.5;
MoveL
[[0,30,80],[0,1,0,0],[0,0,0,0],[9E9,9E9,9E9,9E9,9E9,9E9]],v50,fine,Extruder\WObj:=wobj_plate;
MoveL
[[0,200,150],[0,1,0,0],[0,0,0,0],[9E9,9E9,9E9,9E9,9E9,9E9]],v50,fine,Extruder\WObj:=wobj_plate;
MoveL
[[0,200,30],[0,1,0,0],[0,0,0,0],[9E9,9E9,9E9,9E9,9E9,9E9]],v50,fine,Extruder\WObj:=wobj_plate;
WaitTime 0.5;
SetDO DO10_2,0;
SetDO DO10_1,1;!drop
WaitTime 1;
MoveL
[[0,200,150],[0,1,0,0],[0,0,0,0],[9E9,9E9,9E9,9E9,9E9,9E9]],v50,fine,Extruder\WObj:=wobj_plate;
MoveL
[[0,100,150],[0,1,0,0],[0,0,0,0],[9E9,9E9,9E9,9E9,9E9,9E9]],v50,fine,Extruder\WObj:=wobj_plate;
endproc
ENDMODULE
```

Figure 38:
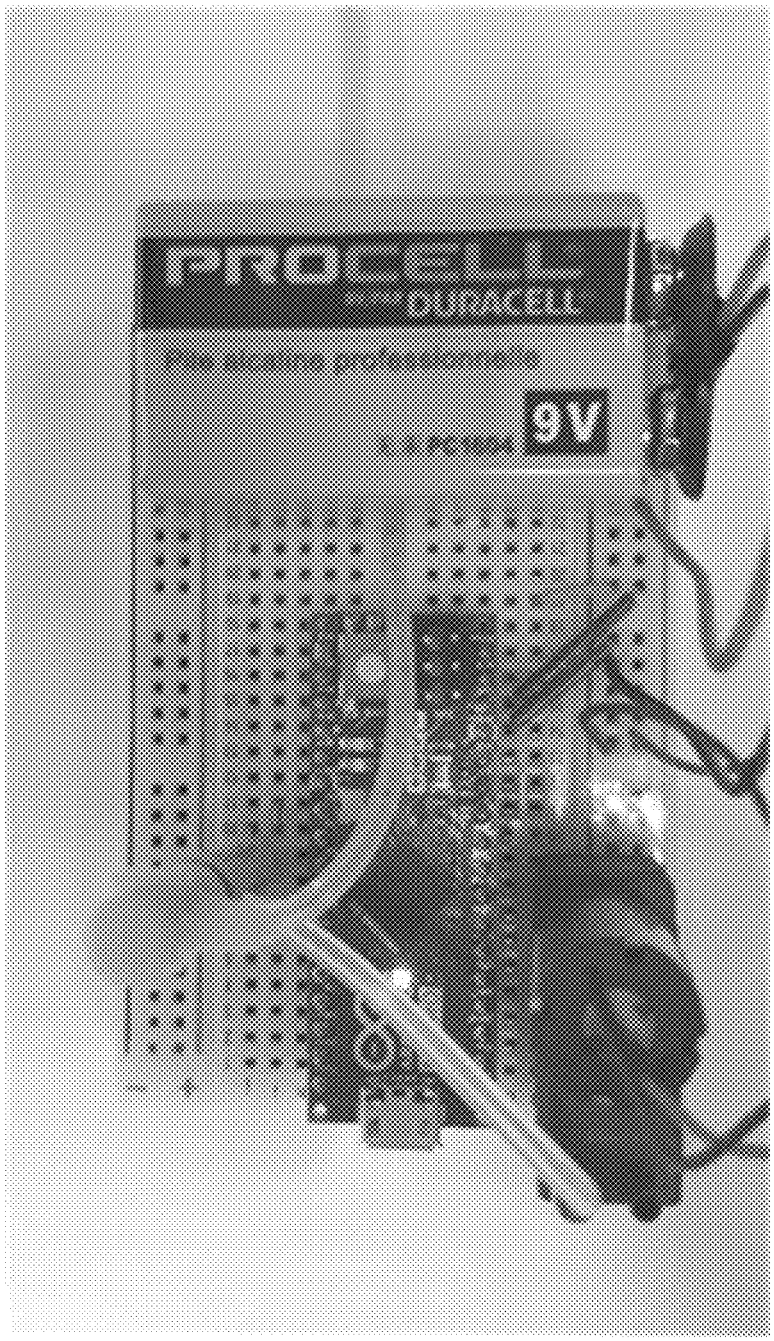
FIG. 38 depicts an actuation system of the Water Strider Robot device.

In one embodiment, the pneumatic system consists of a LHL 3-way latching solenoid valve, a mini compressor (SN 191852), Arduino Micro microcontroller and a 9V battery as shown in FIG. 38 shows the actuation system.

Figure 39:
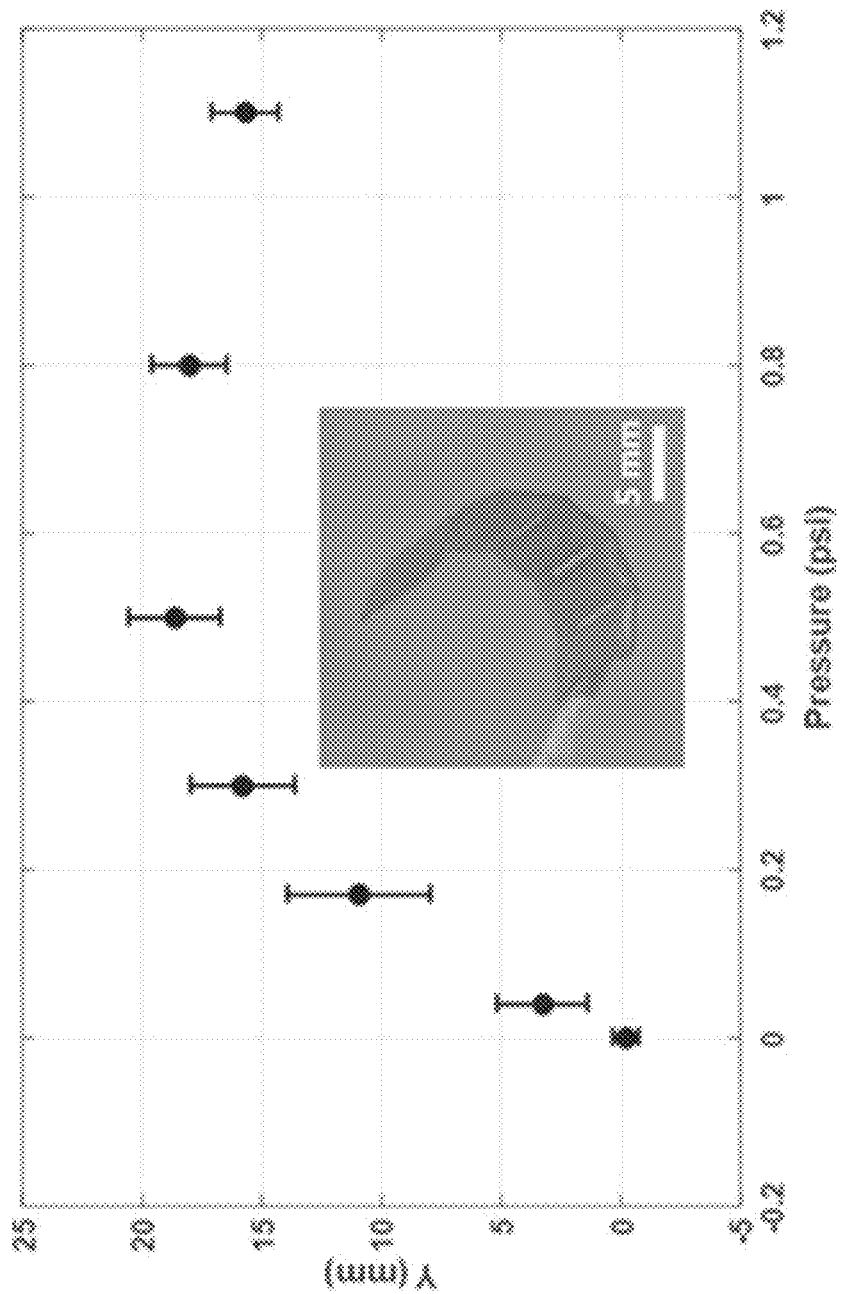
FIG. 39 shows the bending displacement of a soft robotic device of type I under different pressure inputs.

FIG. 39 shows characterization of bending displacement of soft robotic device type I under different pressure inputs.

Figure 40:
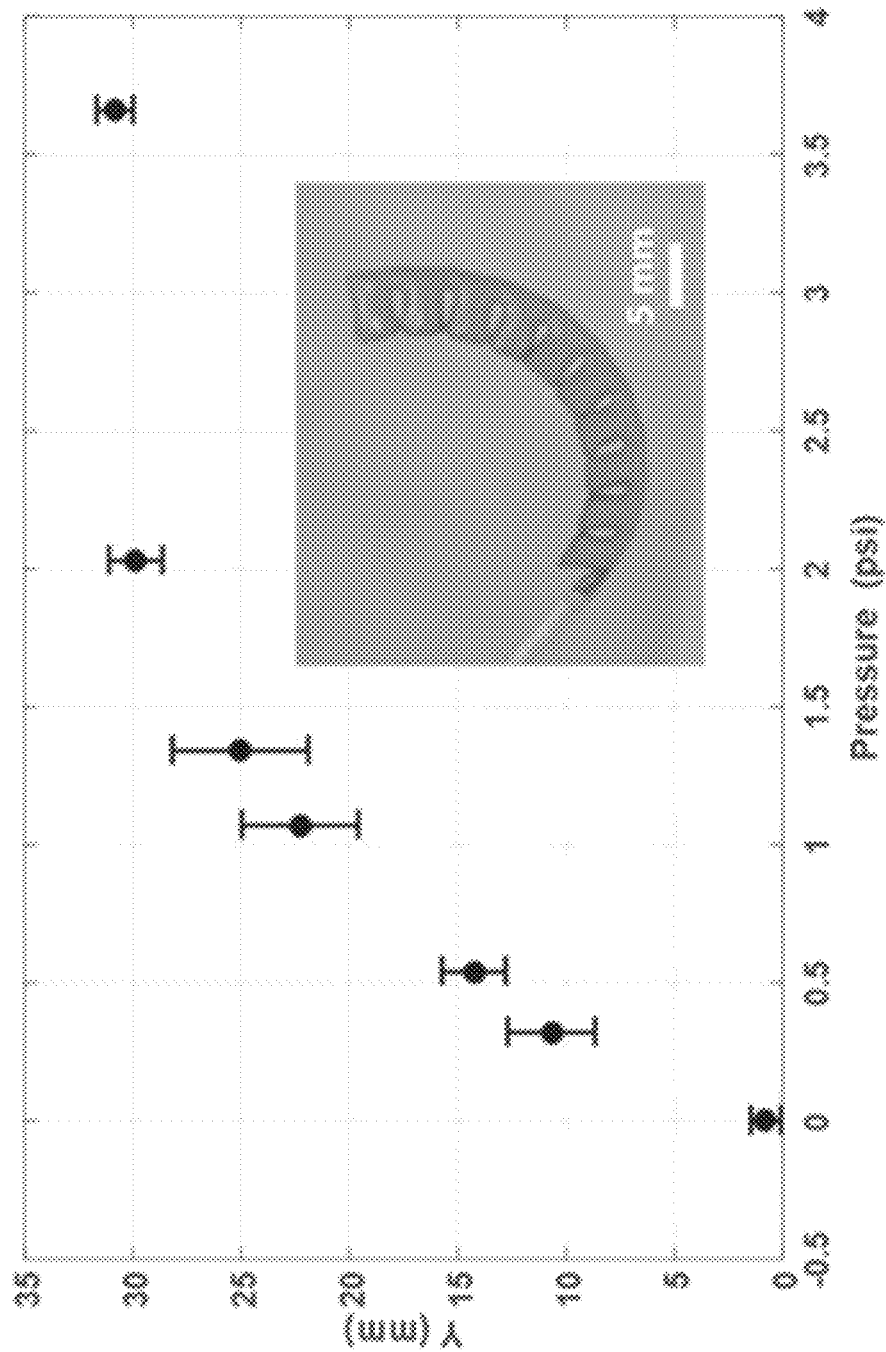
FIG. 40 shows the bending displacement of a soft robotic device of type II under different pressure inputs.

FIG. 40 shows characterization of bending displacement of soft robotic device type II under different pressure inputs.

Figure 41:
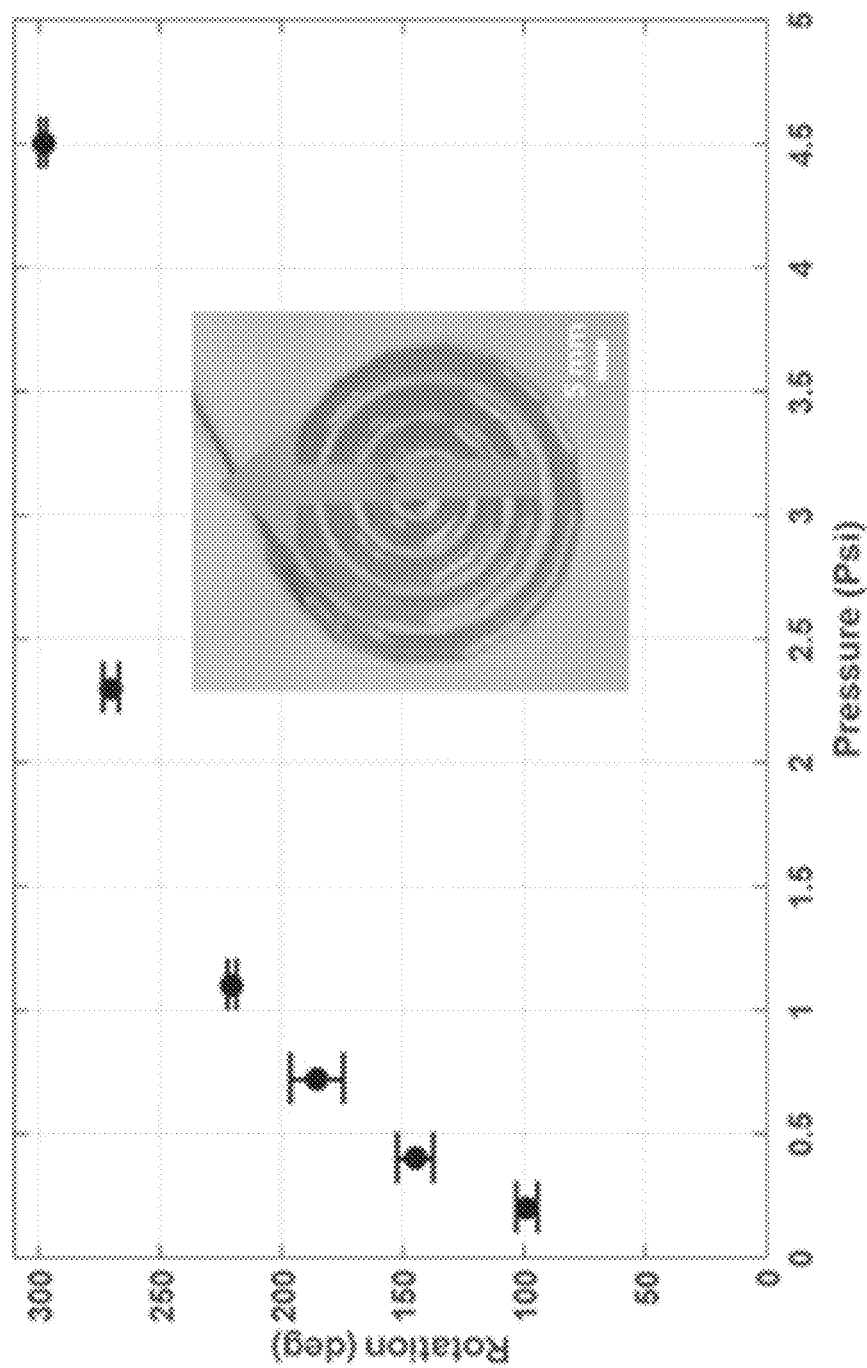
FIG. 41 shows a twisting angle of a rotary soft robotic device for different input pressures.

FIG. 41 shows characterization of twisting angle of rotary device for different input pressures.

Figure 42A:
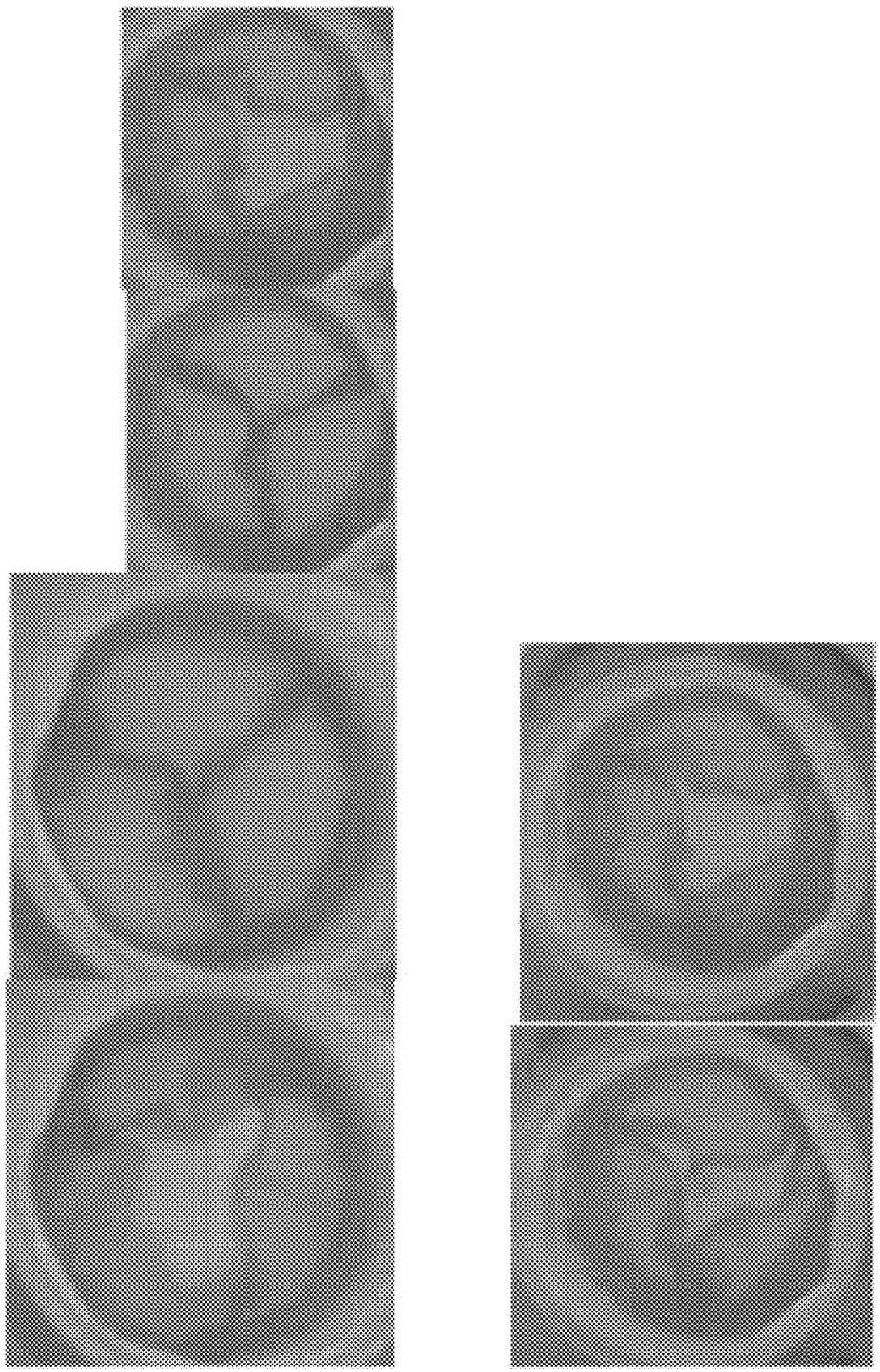
FIGS. 42A-42C show a heart valve embodiment of a soft robotic device.
Figure 42B:
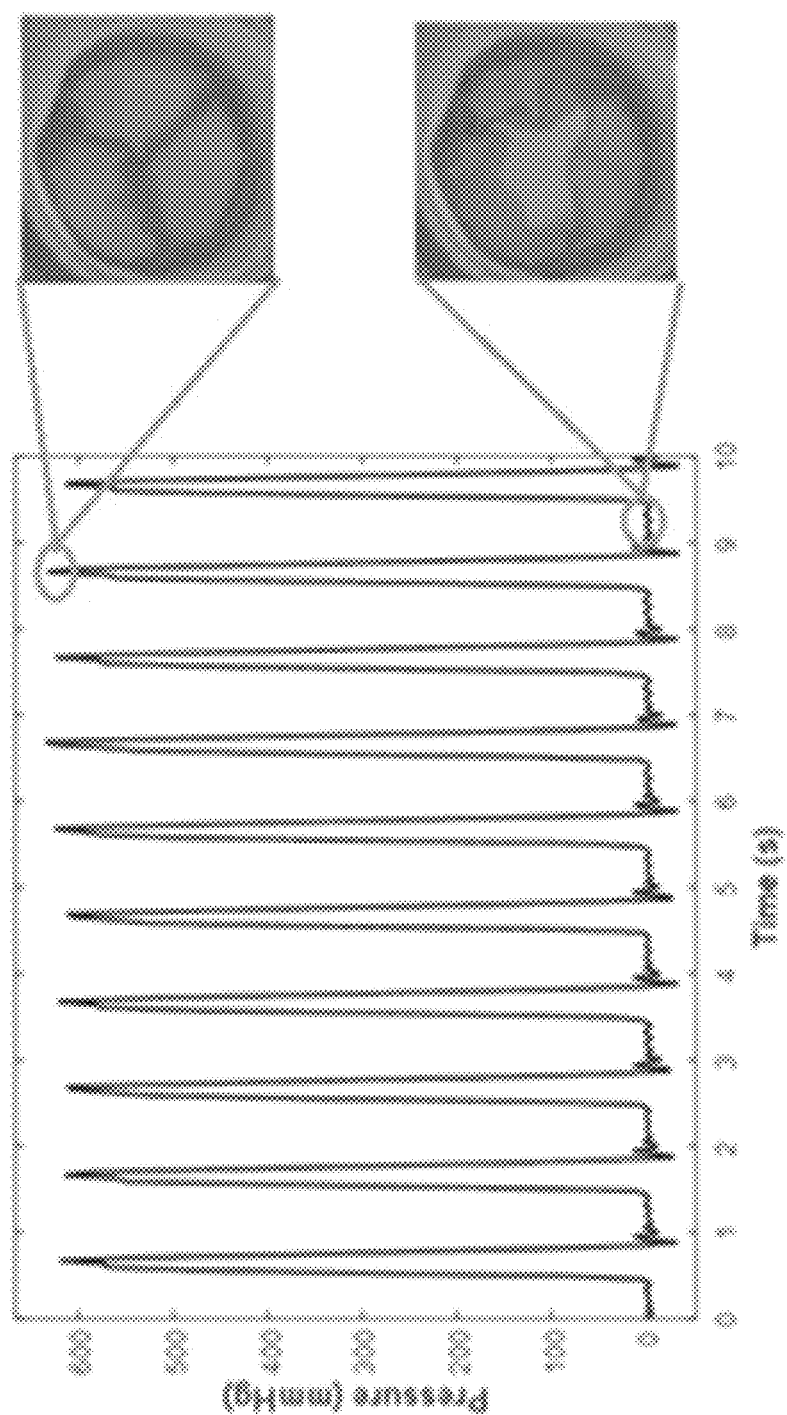
Figure 42C:
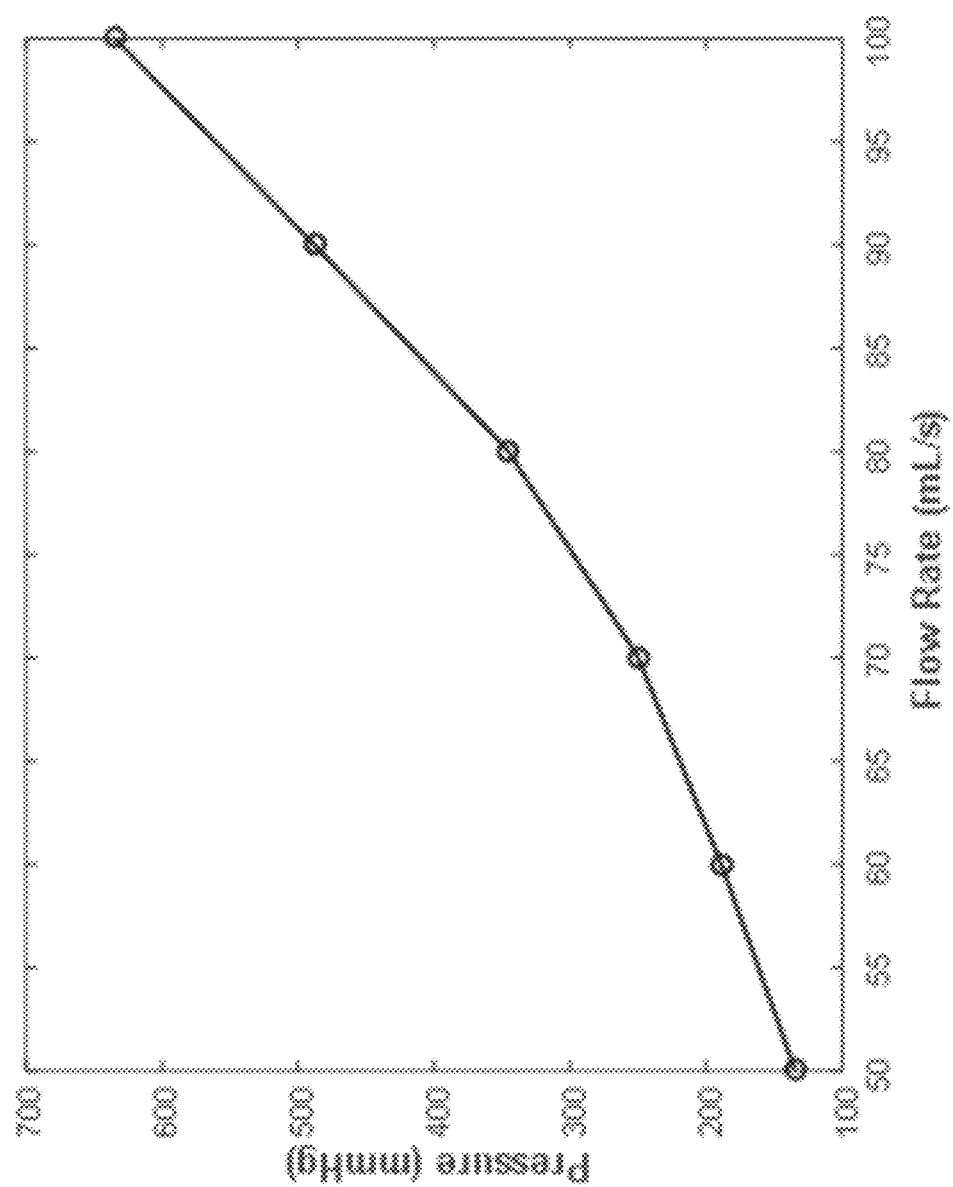
Figure 43A:
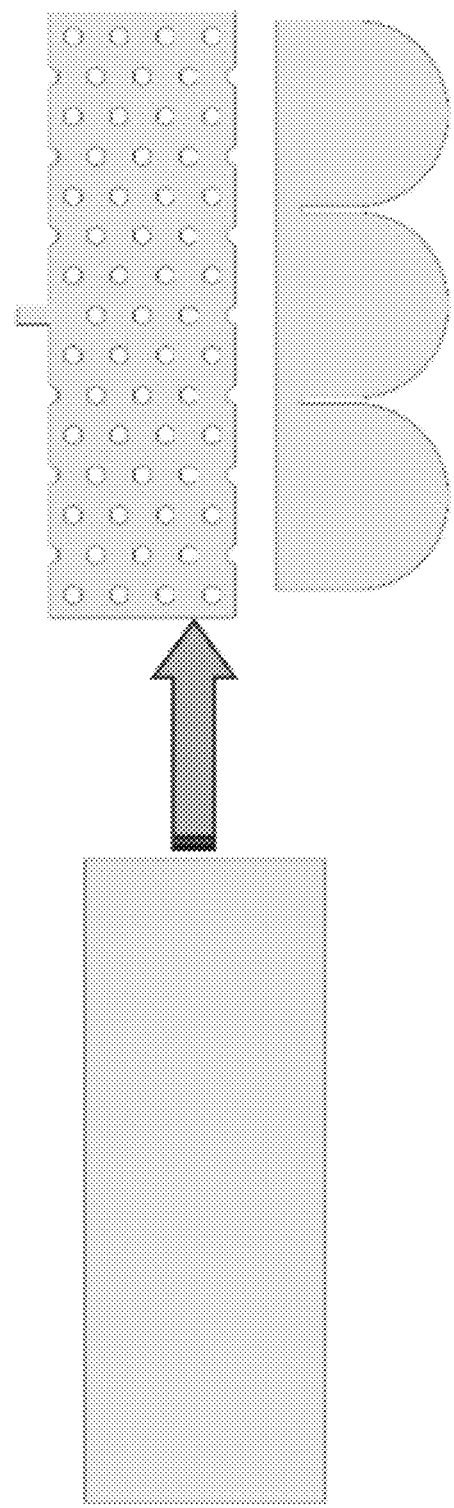
FIGS. 43A-43E depict a thermoplastic bonding method that can be used to integrate multiple layers and a frame of a soft robotic device at a single step.
Figure 43B:
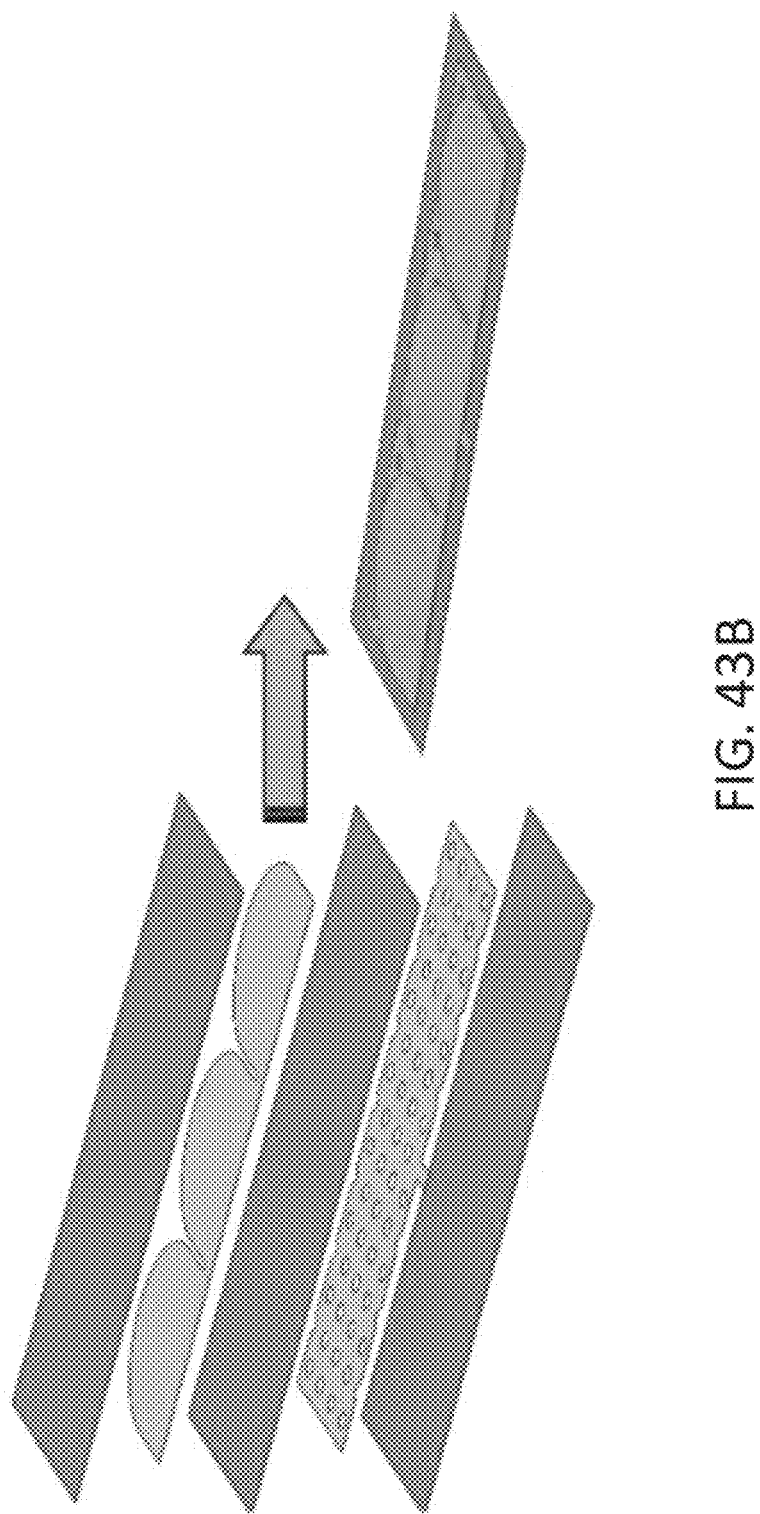
Figure 43C:
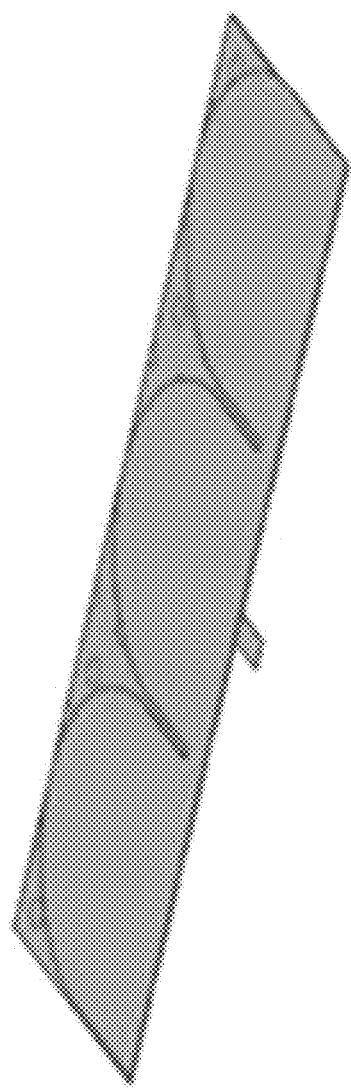
Figure 43D:
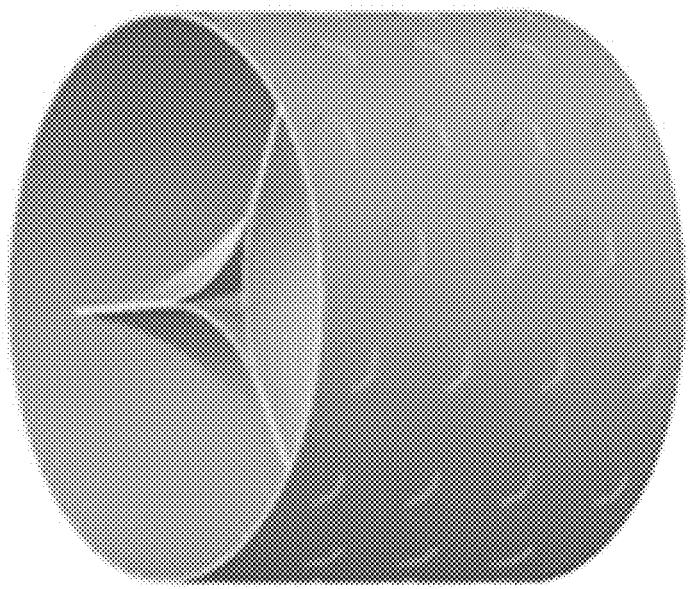
Figure 43E:
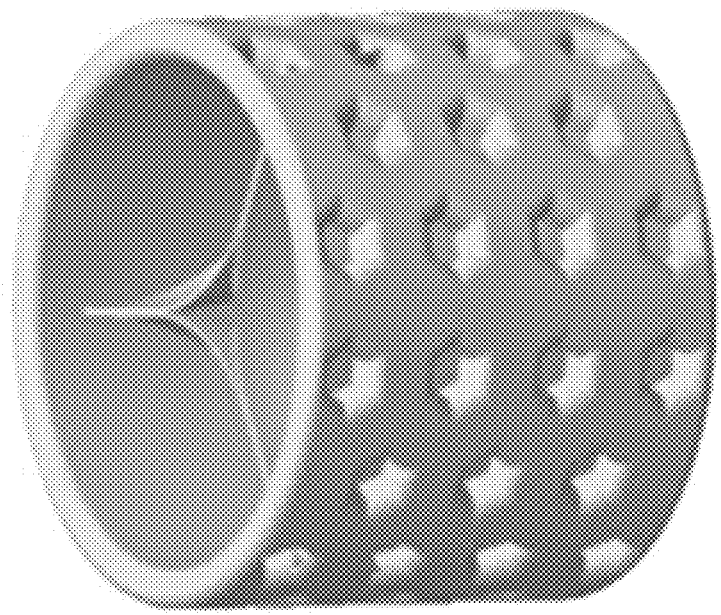

Valvular heart disease including valve stenosis or regurgitation is a big health concern in modern societies. According to American Heart Association, more than 200 000 semilunar and about 70 000 atrioventricular valve replacements are performed annually in USA. It is known that risk factor of heart valve disease increases with age. Thus, heart valve disease will be an important concern for rapid aging countries such as USA. While, surgical valve replacement is not recommended for all patients, transcatheter heart valve replacement is an alternative treatment that has been received great attention among researchers recently. Although this therapy has been relatively established for replacement of aortic valve, it is not well developed for other heart valves such as mitral or tricuspid valves. The existing metallic stent valves cannot efficiently conform to the complex geometry of mitral/tricuspid valves, resulting in paravalvular leak and insufficient anchoring. To tackle this problem, the synthetic heart valves can be made of soft materials such as polymers and elastomers. Recent invention by Direct Flow Medical (DFM) provides an inflatable, non-metallic, fully retrievable, and repositionable percutaneous aortic valve, which may lead to safer implantation of trans-catheter aortic valve. In one embodiment, the soft robotic device disclosed herein can be a heart valve, which is an inflatable unstented prosthetic heart valve and can be deployed to all four naturally-existing heart valves (tricuspid, pulmonic, mitral, and aortic valves). As shown in FIG. 42A, when the heat valve is in an actuated conformation, it is closed and allows low or no flow though. However, when the heart valve is in an unactuated conformation it is open and allows flow though. In an embodiment, the heart valve includes a high-pressure balloon, a low-pressure balloon and soft arms. FIG. 42B depicts change in pressure over time, with highest pressure when the heart valve is closed and lowest pressure when it is open. FIG. 42C shows changes in pressure as flow rate increases. In another embodiment the heart valve consists of any one of the three aforementioned components or any combination and plurality of the three aforementioned components. In an embodiment of the heart valve embodiment, the high-pressure balloon can be a patterned low-thickness balloon which functions as the backbone of the valve, the low-pressure balloon can be a plane low thickness soft balloon which completely conforms to the geometry of the valve annulus and eliminates any paravalvular leaks and finally the soft arms can bend and anchor to the valve annulus. The subject receiving the heart valve can be a human, non-human primate or any subject having one or more naturally existing heart valves. In an embodiment of the heart valve embodiment, a thermoplastic bonding method can be used to construct the heart valve by integrating the layers and the frame of the valve at a single step as depicted in FIGS. 43A-43E. The thermoplastic bonding method includes cutting a water-soluble film into a pattern as illustrated in FIG. 43A, heat-pressing the film between polyurethane films as illustrated in FIG. 43B, cutting seams to a desired length as illustrated in FIG. 43C, and bending the obtained patterned balloon into a cylindrical shape, overlapping and attaching the short edges (e.g., via a binding clip) as illustrated in FIG. 43D. The frame can then be put inside an oven, dissolving the water-soluble film, and the frame can be inflated with polymer or other suitable substance such as a liquid or a gas, as illustrated in FIG. 43E. In another embodiment a laser welding method can be used to construct the heart valve.

In one embodiment, the soft robotic device can be an inflatable soft stent, referred to as stent hereafter. In an embodiment, the stent is ultra-thin, conformable and made of hemo-compatible and biocompatible polyurethane material. In an embodiment of the stent embodiment, a thermoplastic bonding method can be used to construct the stent by integrating the layers and the frame of the stent at a single step as depicted in FIGS. 43A-43E for the heart valve embodiment of a soft robotic device. FIGS. 43A-43E describe the thermoplastic bonding method using a valve frame as an example, however, in another embodiment the method can be applied in the construction of a stent frame or any other soft robotic device. In another embodiment a laser welding method can be used to construct the stent. In an embodiment, the stent is utilized in medical procedures such as percutaneous heart valve replacement. In another embodiment, the stent is relevant in maintaining pressure or supporting blood vessels, canals, or ducts to prevent collapse or re-narrowing of a vessel, aid in healing or to relieve an obstruction. In one embodiment, the stent may be pre-coated with a drug such as a drug, which interrupts the re-narrowing of a blood vessel. In one embodiment, the stem can be constructed from a polymer, which over time dissolves in a patient's body.

Figures 44A, 44B, 44C, 44D:
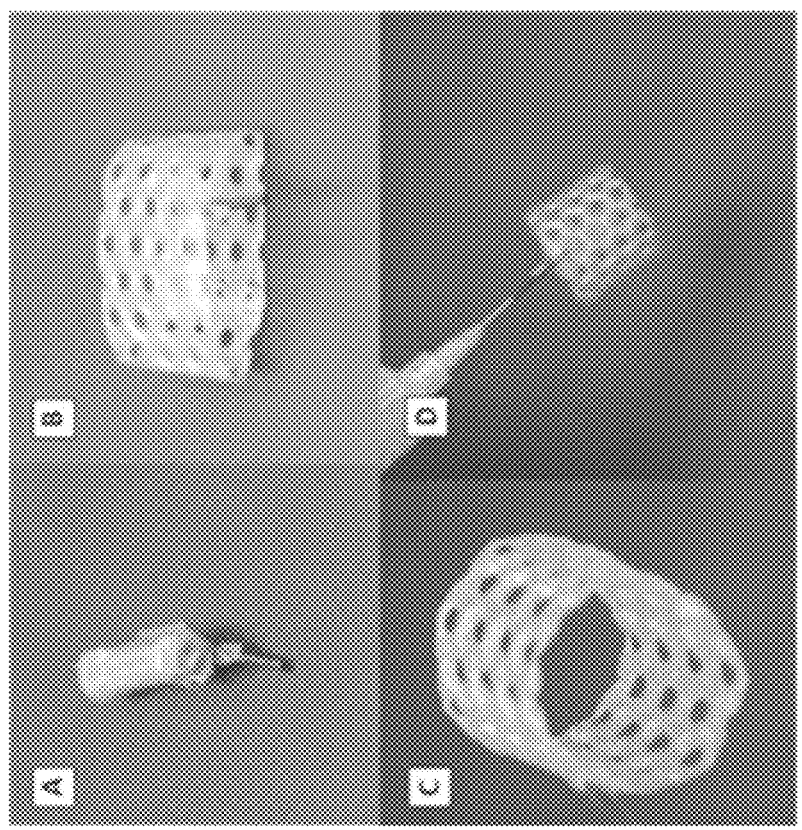
FIGS. 44A-44D show an inflatable polyurethane stent in its low-volume conformation in FIG. 44A, deflated conformation in FIG. 44B, inflated conformation in FIG. 44C and inflated conformation connected to an inflating source in FIG. 44D.

An inflatable polyurethane stent is shown in its low-volume conformation in FIG. 44A, it its deflated conformation in FIG. 44B, in its inflated conformation in FIG. 44C, and in its inflated conformation connected to an inflating source in FIG. 44D. In an embodiment, the stent is 70 μm thick. In another embodiment, the stent thickness can be more or less than 70 μm. In an embodiment, the stent is constructed from polyurethane. In another embodiment, the stent can be made of any suitable polymer, which is biocompatible and can withstand the heating and cooling processes involved in soft robotic device construction.

Figures 45A, 45B, 45C, 45D, 45E, 45F:
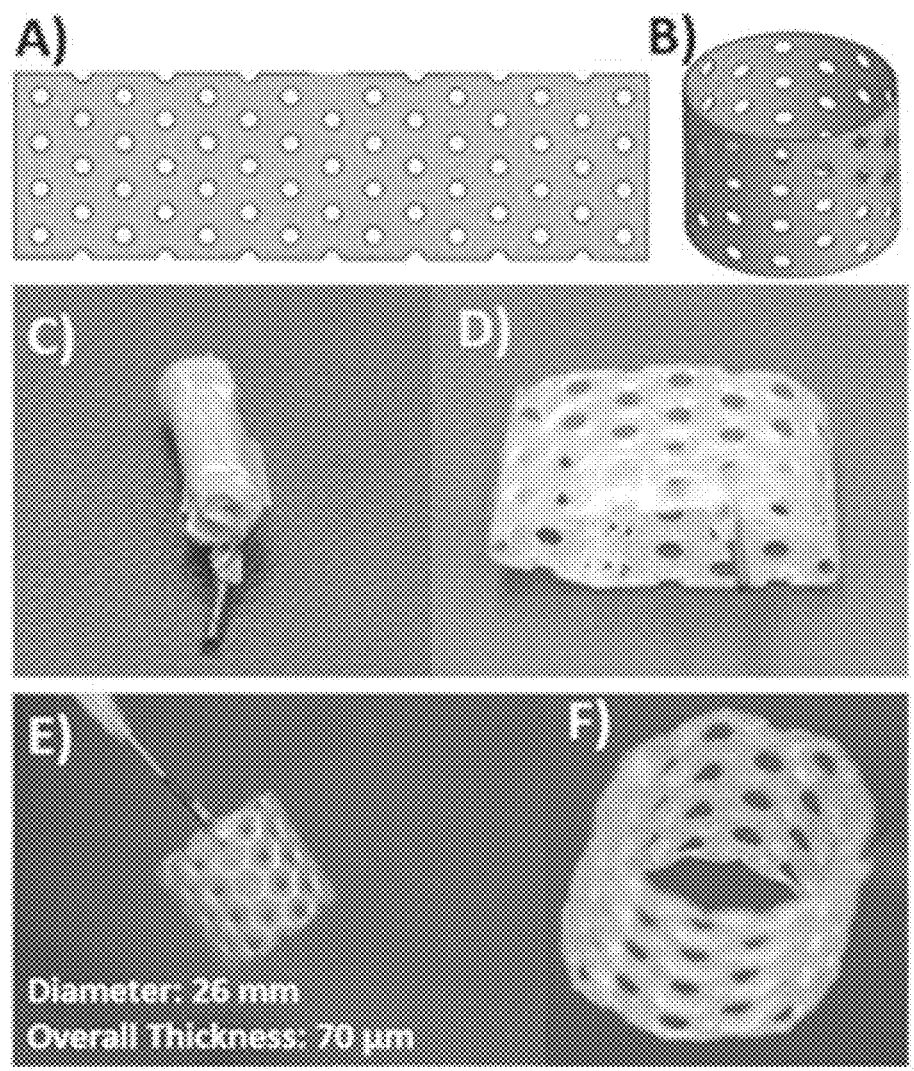
FIGS. 45A-45F show an embodiment in which the soft robotic device is a stent.

In one embodiment of the stent embodiment, the stent can be generated by using a flat plain balloon, bending the balloon to form a cylindrical shape, and gluing along the short edges as illustrated in FIGS. 45A and 45B. The flat plain balloon can also include a pattern to increase flexibility. One example of such a pattern is a honeycomb pattern as seen in FIGS. 45A-45F. FIG. 45C shows the stent in its low-volume conformation. FIG. 45D shows the stent in its deflated conformation. FIG. 45E shows the stent in its inflated conformation with an inflation source attached. FIG. 45F shows the stent in its inflated conformation. Other suitable patterns can also be used to generate a stent. The size and shape of these patterns can change the radial and axial stiffness of the stent.

Figure 46A:
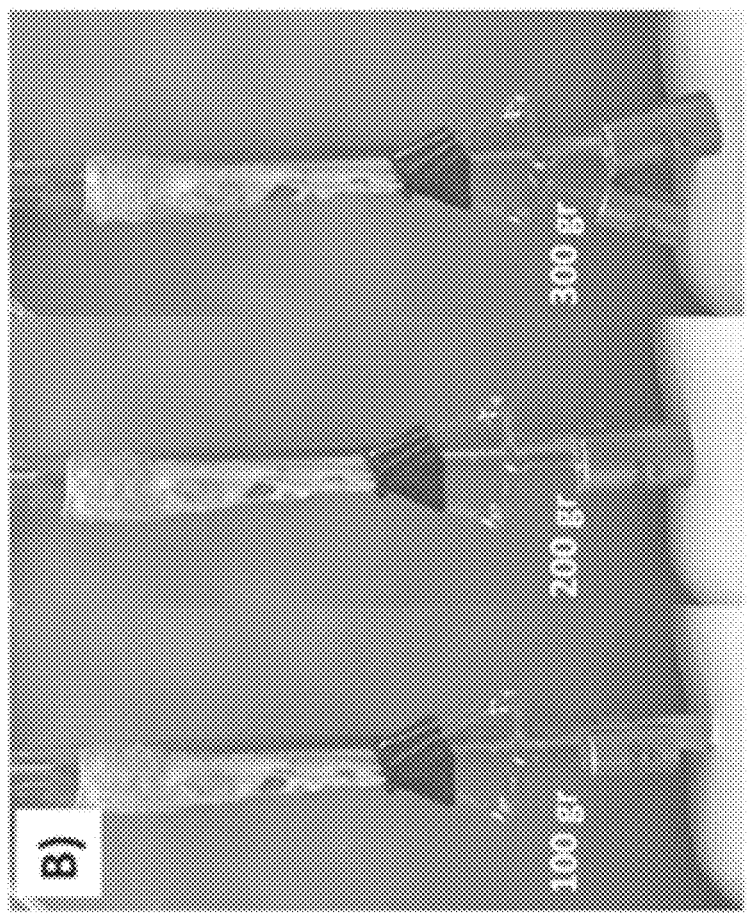
FIGS. 46A and 46B show an embodiment, in which the soft robotic device is a stent. The stent can be attached to a hanging mechanism as illustrated in FIG. 46A. The stent can be further inflated inside a pig's aorta while the aorta is attached to various weights as illustrated in FIG. 46B, showing the strength of the stent.
Figure 46B:
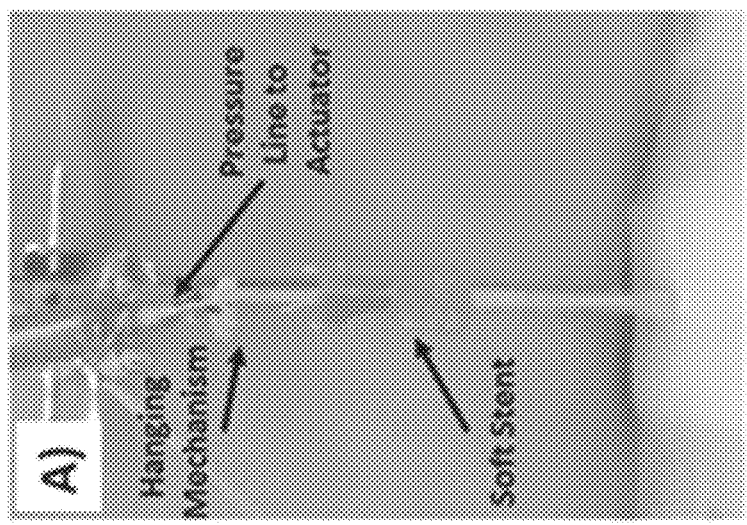
Figure 47A:
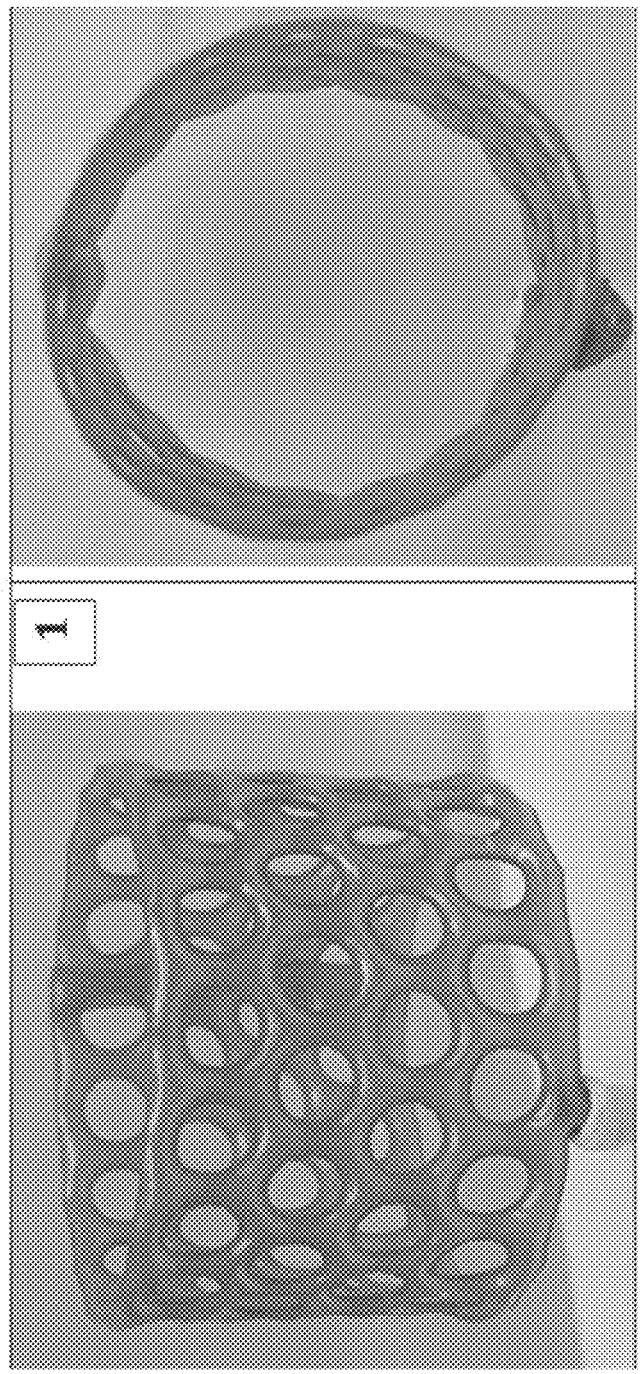
FIGS. 47A-47D show additional images showing different views of the stent as well as the sizes and burst pressures for different patterns.
Figure 47B:
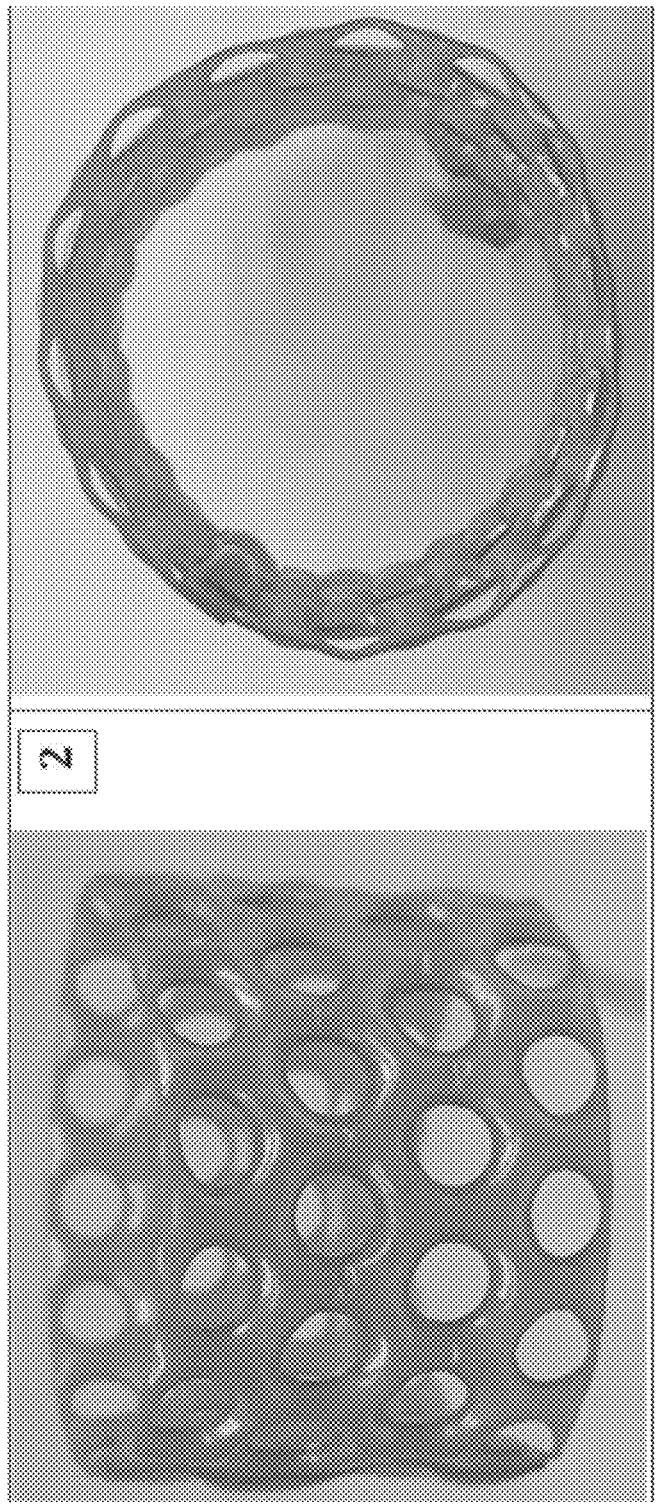
Figure 47C:
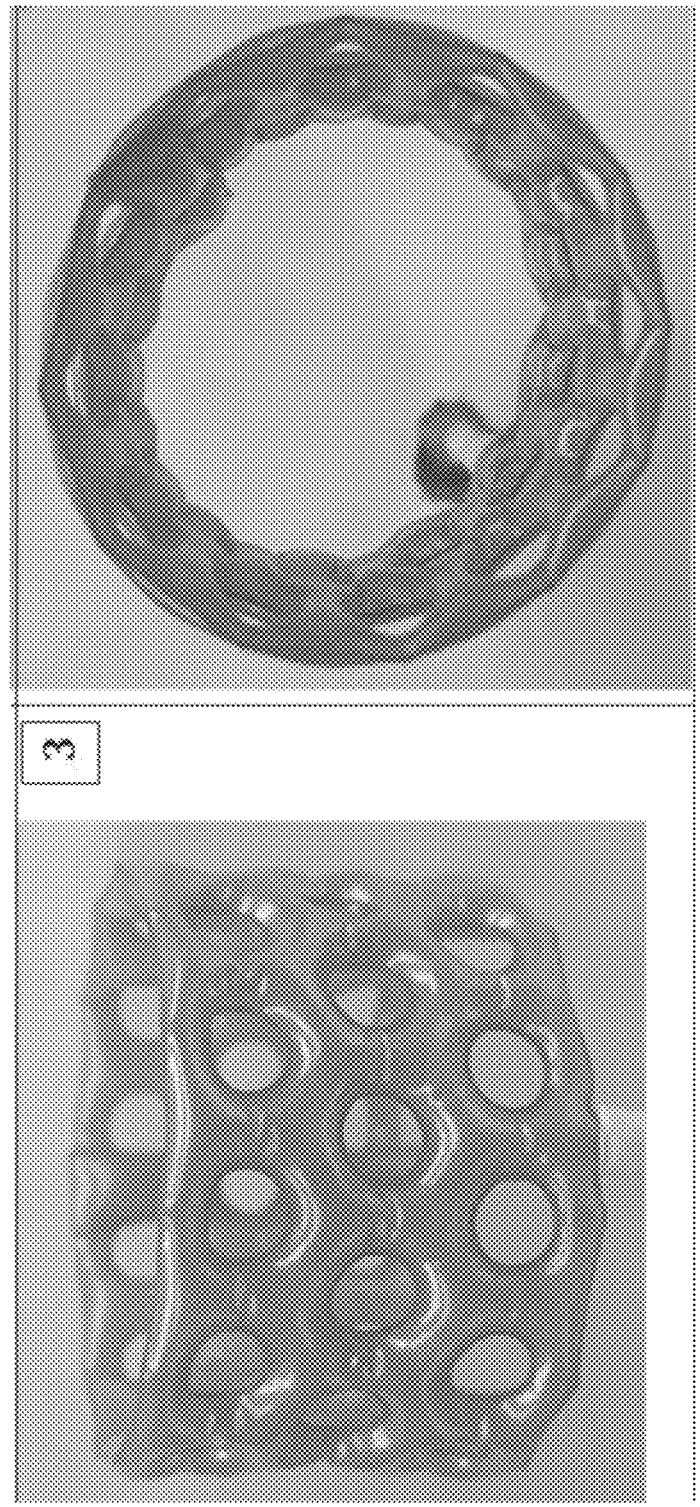
Figure 47D:
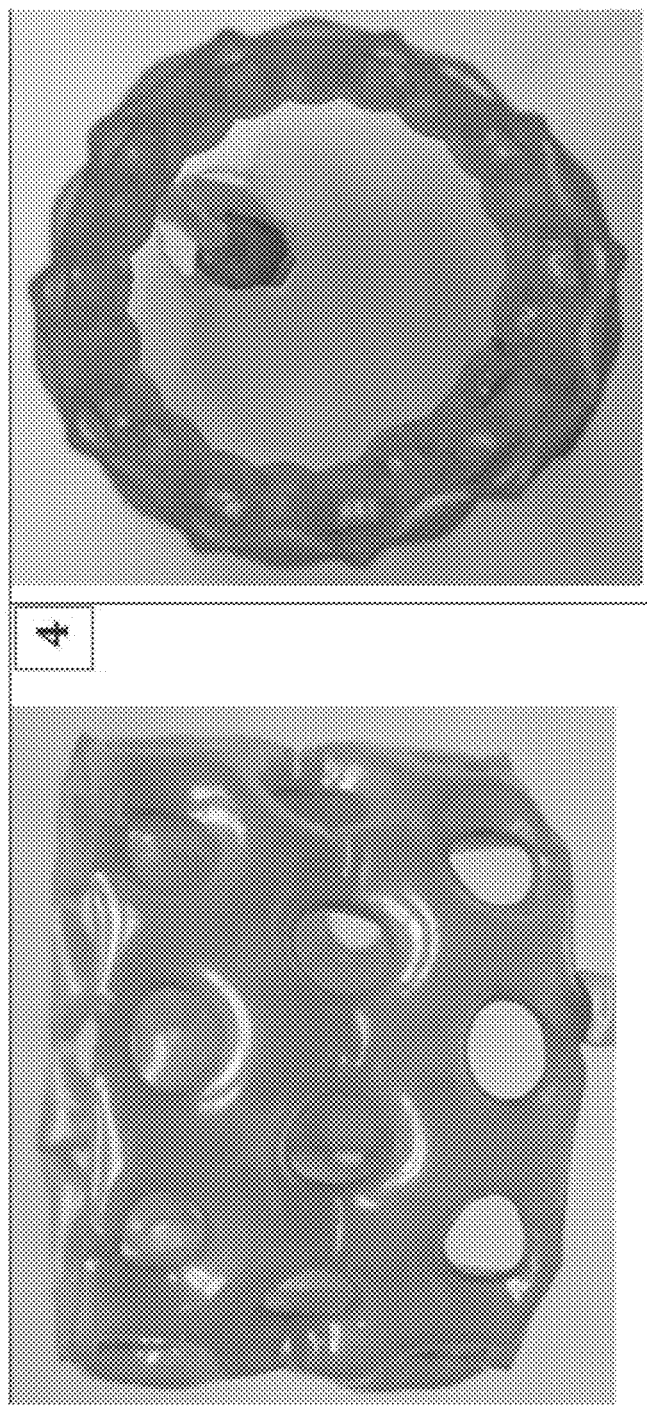
Figure 48A:
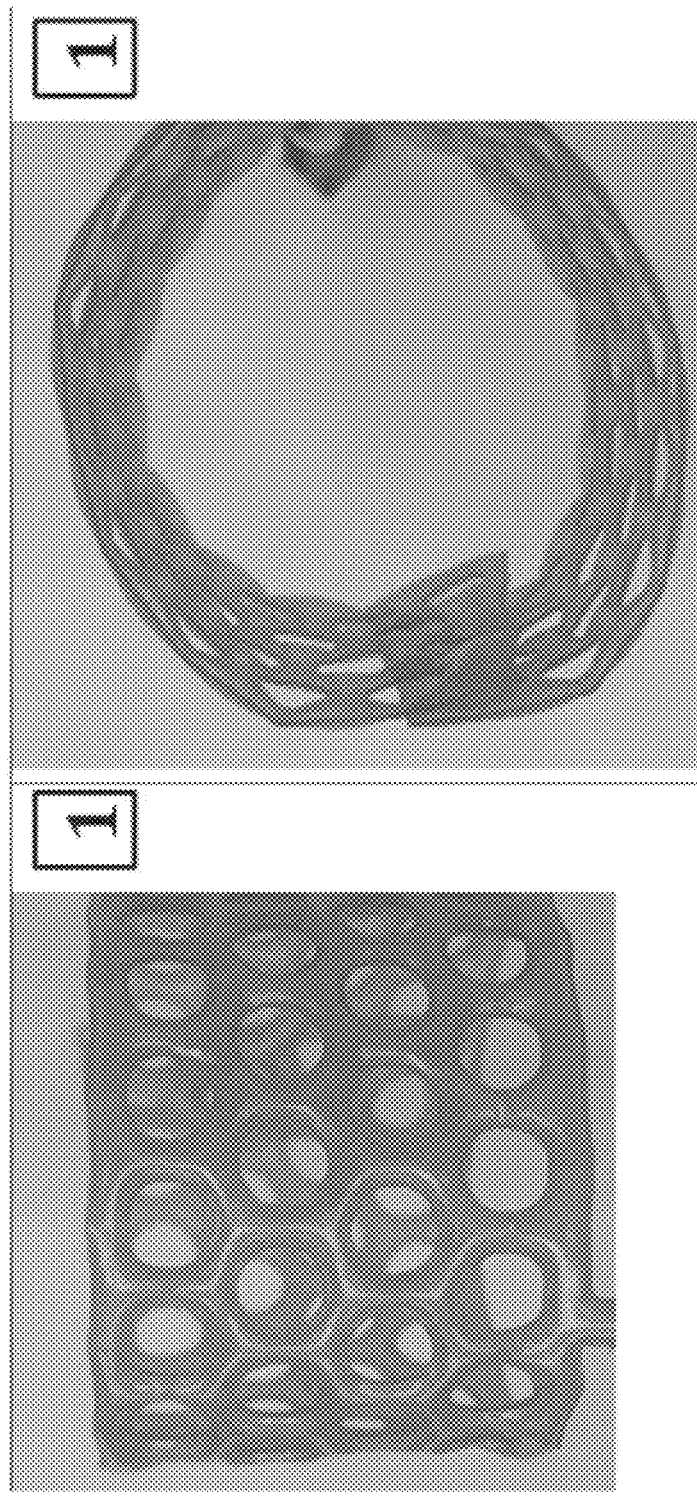
Figure 48B:
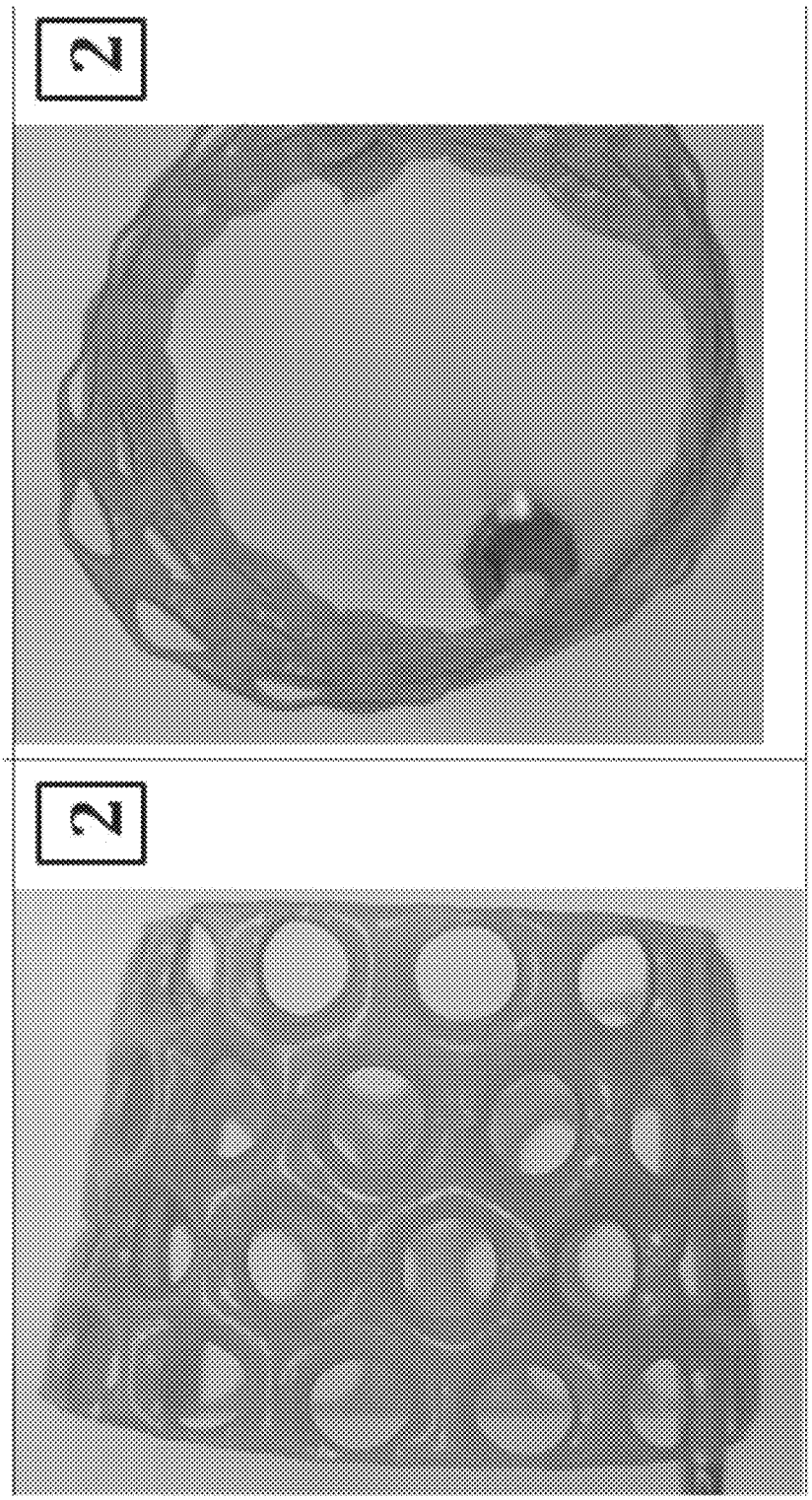
Figure 48D:
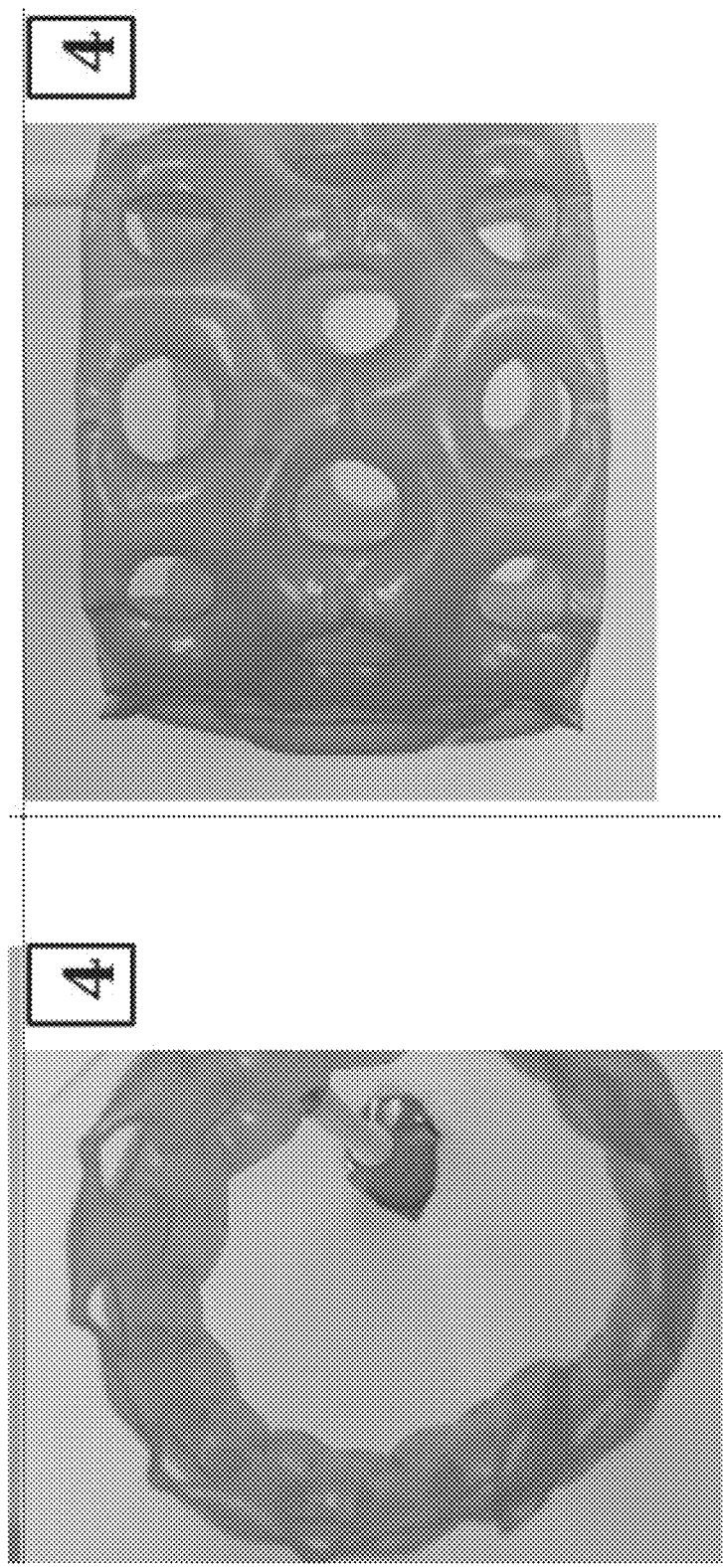
Figure 49A:
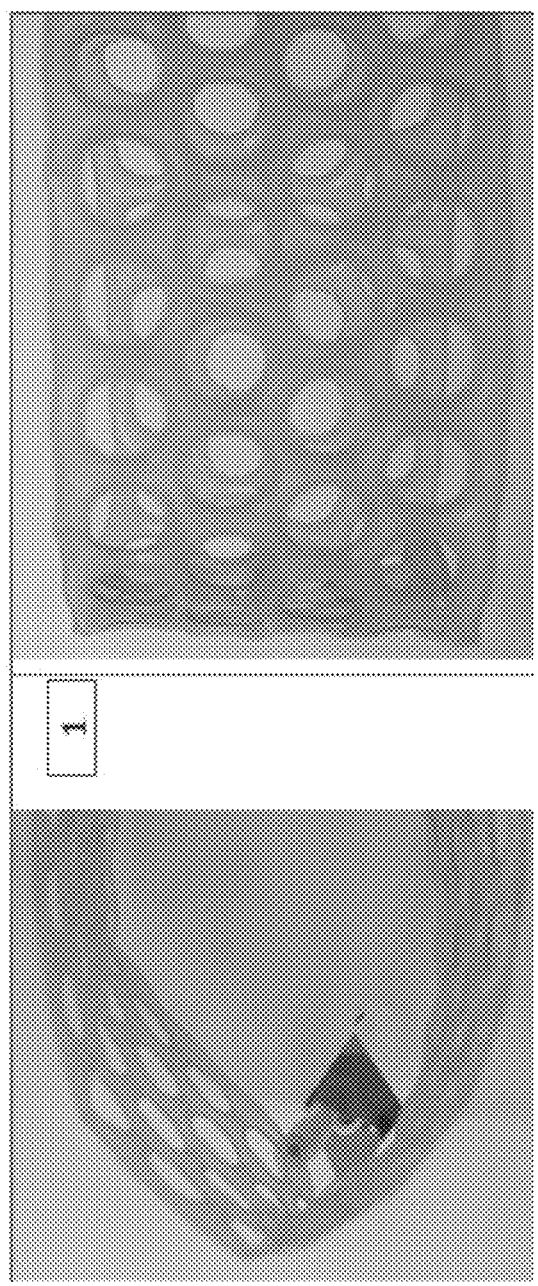
FIGS. 49A-49D show views of different patterns for the stent.
Figure 49B:
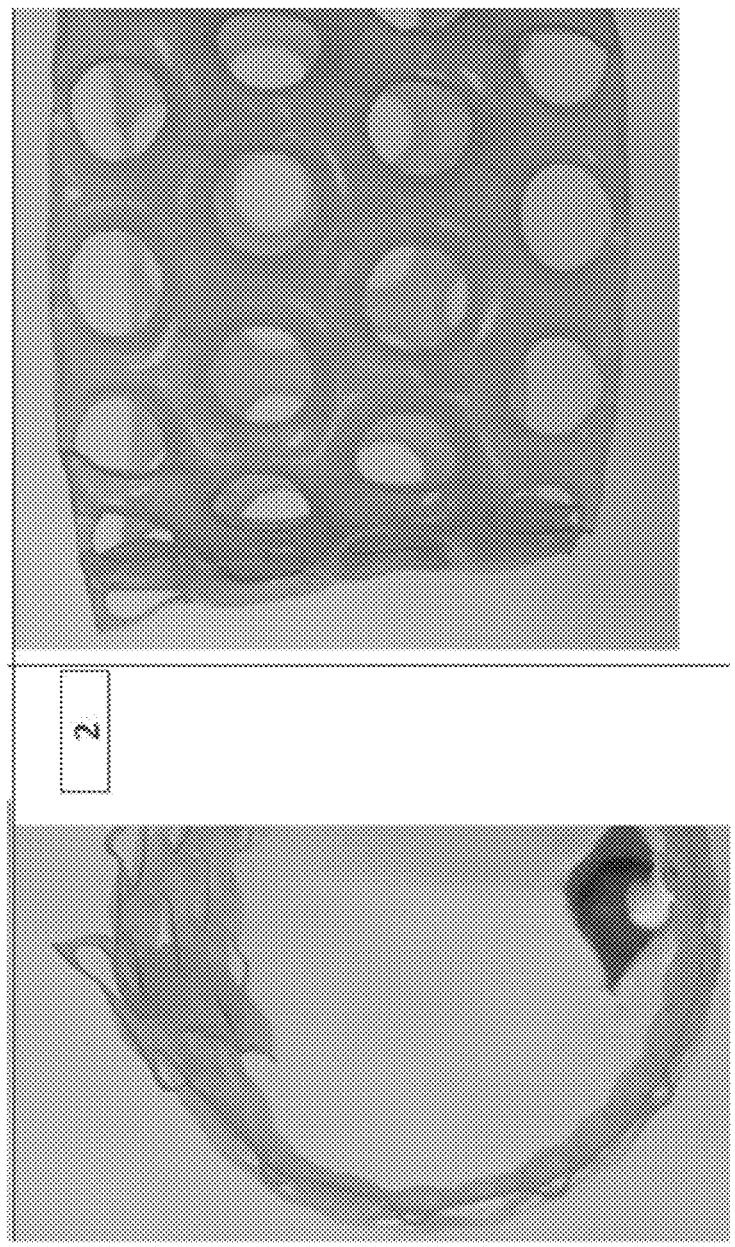
Figure 49C:
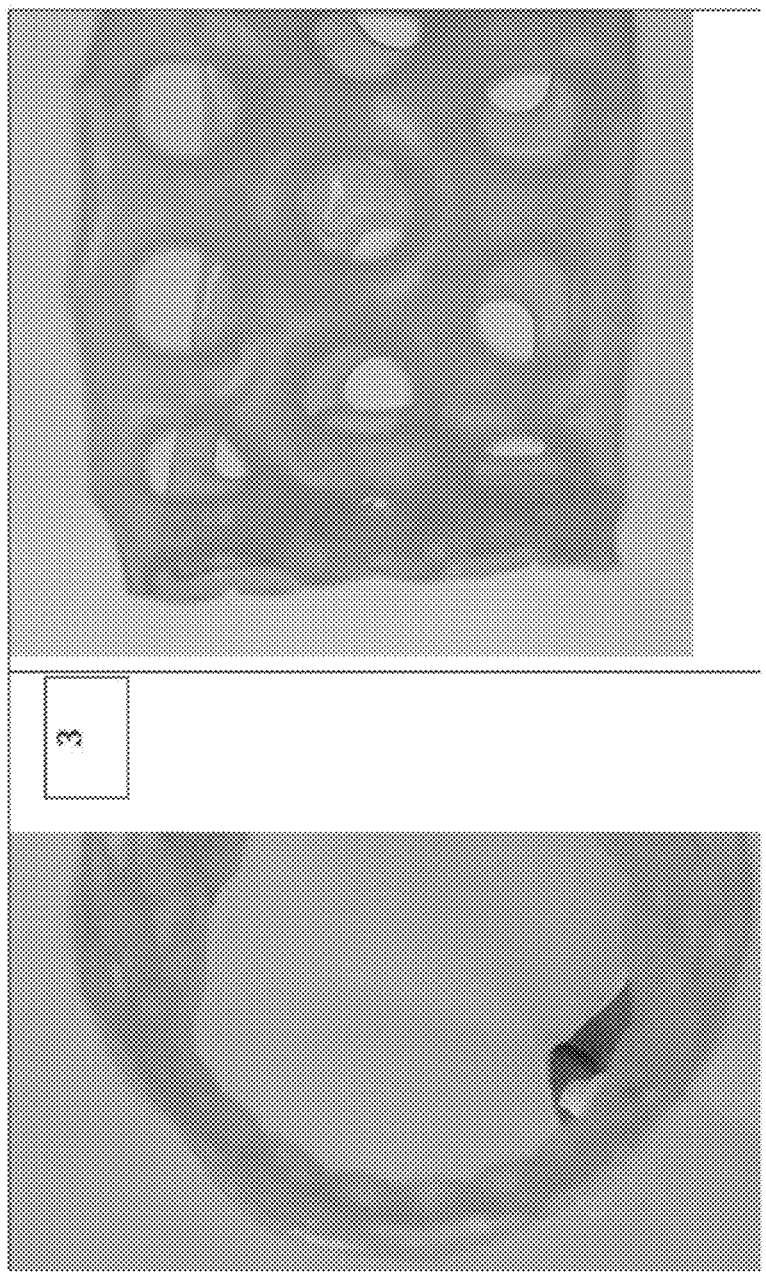
Figure 49D:
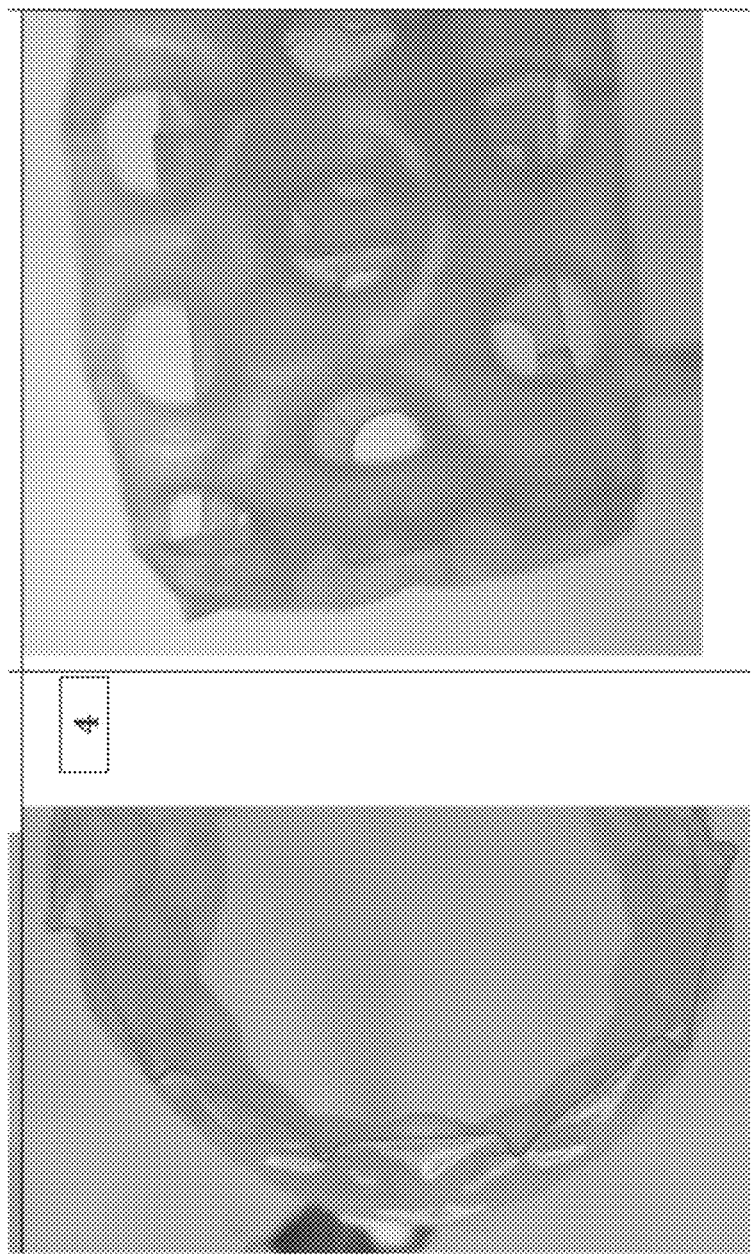

In an embodiment the stent has a diameter of 26 mm and is constructed using a heat press method. In another embodiment the stent diameter may be larger or smaller than 26 mm depending on the size of the vessel, which needs to be supported. A different method or combination of methods of construction can also be utilized in the construction of the stent, for example the laser welding method. As illustrated in FIG. 46A, the stent can be fixed to a support stand using a hanging mechanism. The stent can then be inflated inside a pig aorta while the aorta is attached to a weight. In an embodiment, the stent can lift a mass of up to 350 gr (50 gr is the mass of aorta plus metal clip) at a pressure of 21 psi as shown in FIG. 46B. In another embodiment, the stent can lift a mass greater than 350 g at pressure levels higher or lower than 21 psi. In one embodiment of the stent, the entirety of the valve is enshrouded with PET fabric in order to reinforce the stent upon inflation and avoid bursting at high pressure. Furthermore, the stent surface can be modified to enhance friction forces between the aorta and the stent. For example, micropatterning can improve surface friction. In an embodiment, the stent is 70 μm thick.

FIGS. 47A-47D show views of different patterns for the stent. Size and burst pressures for the patterns shown in FIGS. 47A-47D are presented in the table below

| Pattern # | Thickness (mm) | Diameter (mm) | Burst pressure (Psi) | Distance b/w centers (mm) | Length of Channels (mm) |
|---|---|---|---|---|---|
| 1 | 1.71 | 25.78 | 73 | 5 | 2 |
| 2 | 2.03 | 27.01 | 70 | 6 | 3 |
| 3 | 2.74 | 26.73 | 45 | 7 | 4 |
| 4 | 3.79 | 23.63 | 57 | 8 | 5 |

FIGS. 48A-48D show views of different patterns for the stent. Size and burst pressures for the patterns shown in FIGS. 48A-48D are presented in the table below:

| Pattern # | Thickness (mm) | Diameter (mm) | Burst pressure (Psi) | Distance b/w centers (mm) | Length of Channels (mm) |
|---|---|---|---|---|---|
| 1 | 0.95 | 25.45 | 49 | 5 | 2 |
| 2 | 1.87 | 25.45 | 57 | 6 | 3 |
| 3 | 2.81 | 27.08 | 44 | 7 | 4 |
| 4 | 3.72 | 27.13 | 30 | 8 | 5 |

FIGS. 49A-49D show views of different patterns for the stent. Size and burst pressures for the patterns shown in FIGS. 49A-49D are presented in the table below:

| Pattern # | Thickness (mm) | Diameter (mm) | Burst Pressure (psi) | Distance b/w centers (mm) | Length of channels (mm) |
|---|---|---|---|---|---|
| 1 | 0.10 | 24.6 | 5 | 5 | 2 |
| 2 | 1.81 | 24.93 | 8 | 6 | 3 |
| 3 | 2.80 | 27.53 | 5 | 7 | 4 |
| 4 | 2.91 | 26.61 | 5 | 8 | 5 |

Figure 50B:
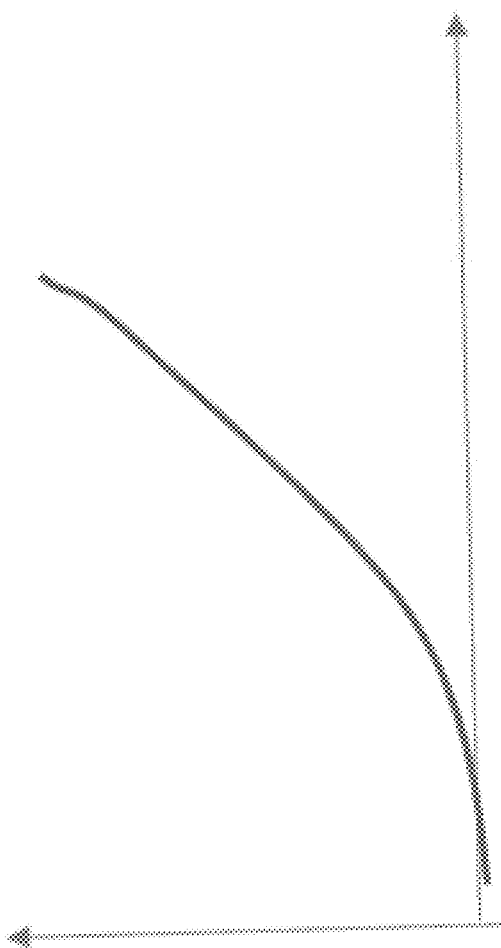
FIG. 50B shows a graph depicting the maximum pull-out for a stent vs. applied pressure.
Figure 51A:
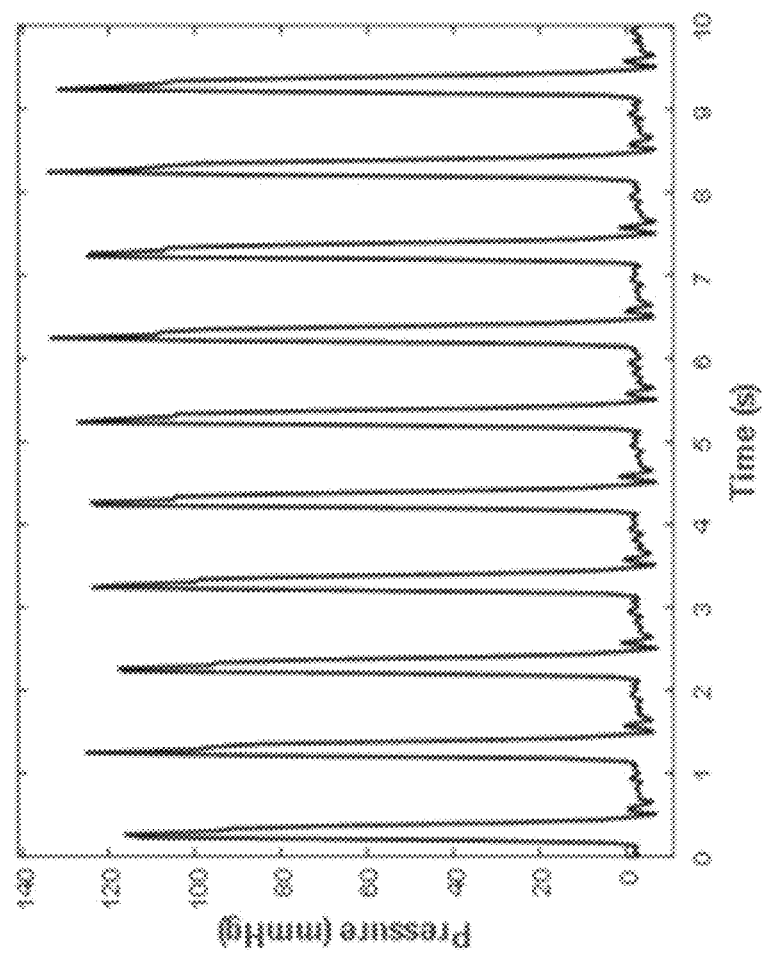
FIGS. 51A-51F show a series of graphs depicting pressure vs. time.
Figure 51B:
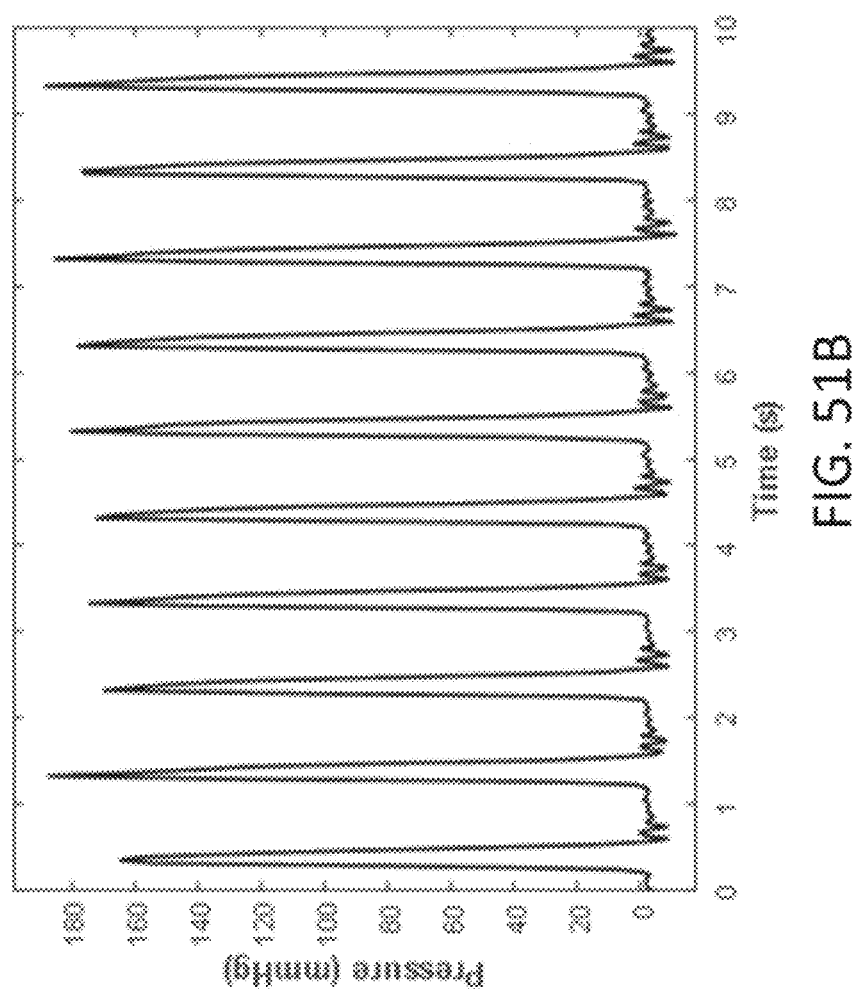
Figure 51C:
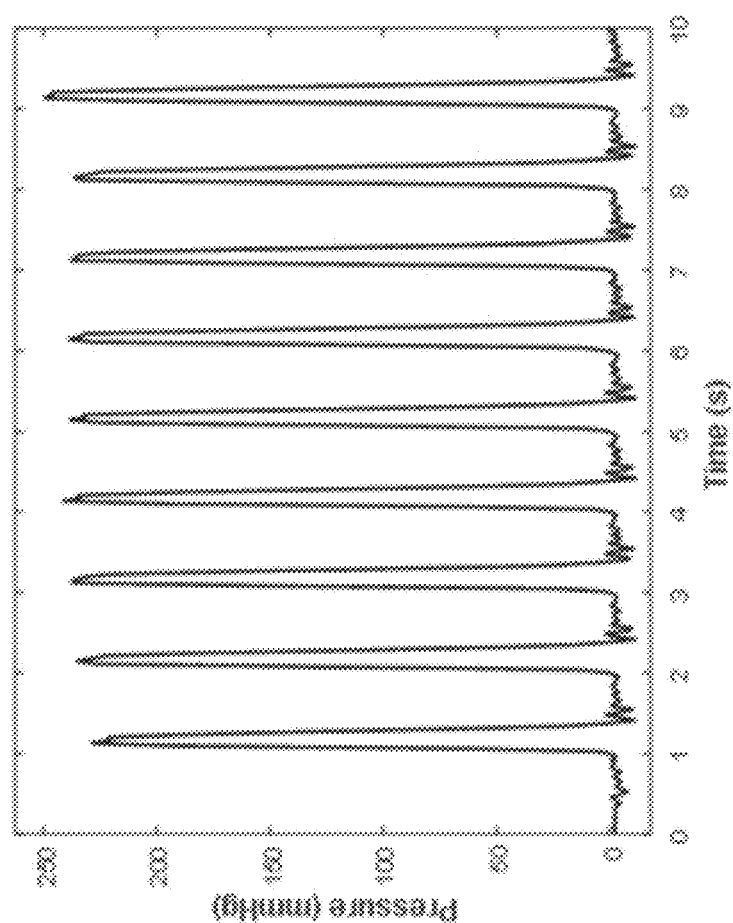
Figure 51D:
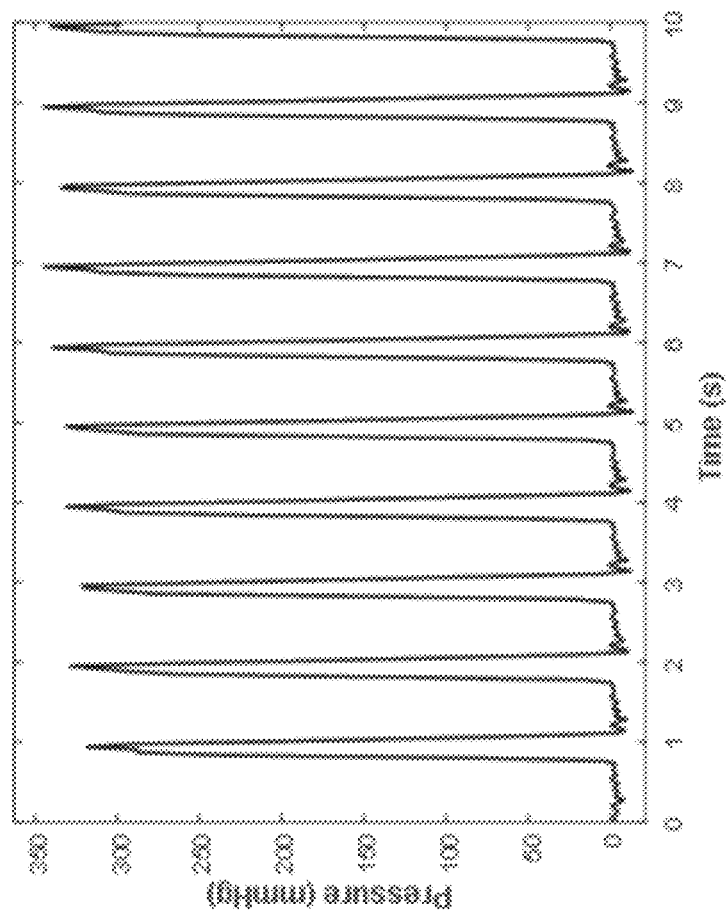
Figure 51E:
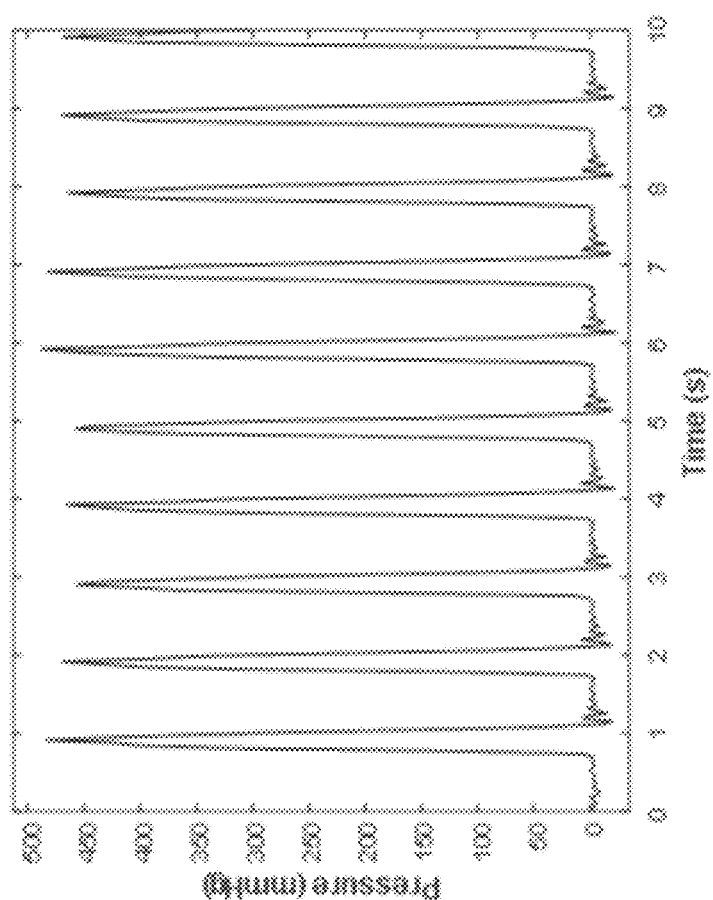
Figure 51F:
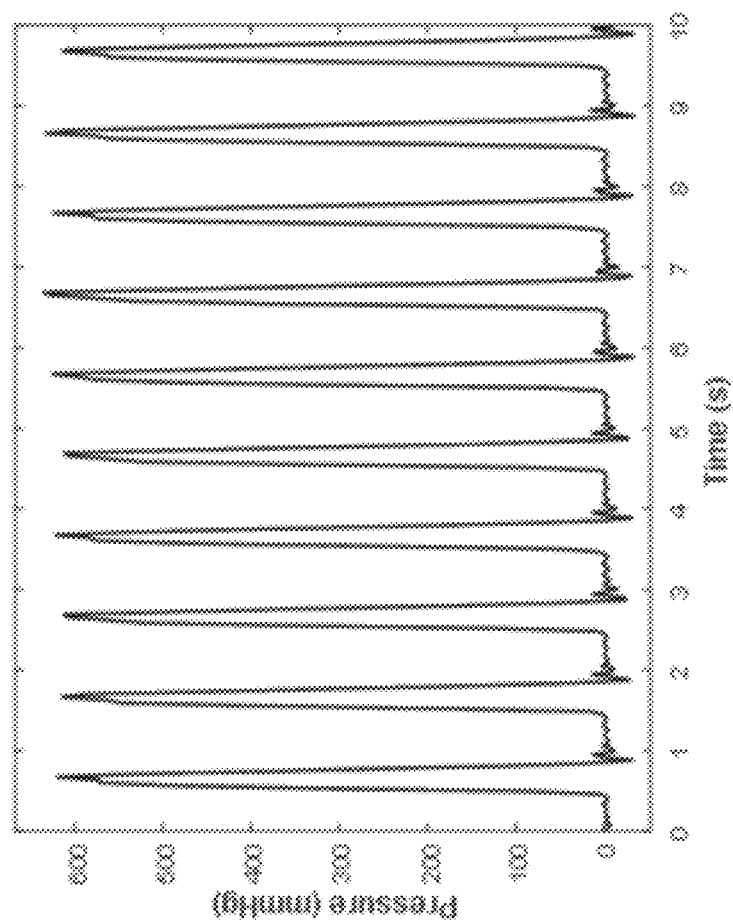

FIG. 50A shows a set of realistic annulus shapes. These shapes can be used to show conformability of the stent. FIG. 50B shows a graph depicting the maximum pull-out for a stent vs. applied pressure. Sizing of the actuator also may alter the graph.

FIGS. 51A-51F show a series of graphs depicting pressure vs. time.

Figure 52:
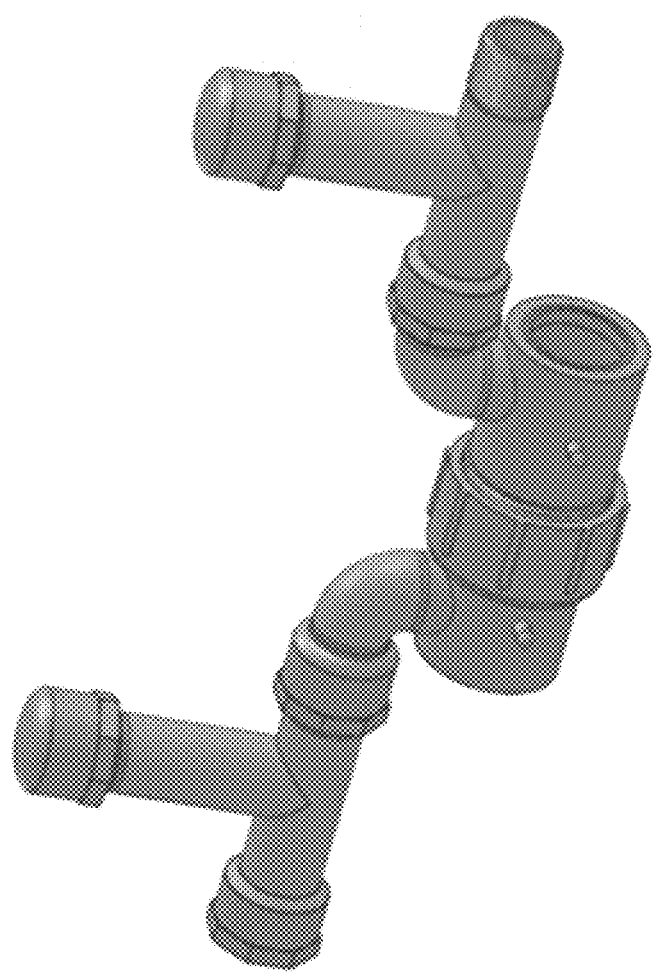
FIG. 52 shows two objects coupled together.

FIG. 52 shows two objects coupled together.

In some embodiments heat can be used to repair small defects such as delamination or rupture of a soft robotic device. Thermoplastic-based soft robotic devices can be repaired by hot pressing the device again. Heat can be applied over the entire device or in a small region of the device.

In some embodiments, individual soft robotic devices can be constructed and then combined to form a more complex, sophisticated soft machine. These sophisticated soft machines can be made by combining individual devices by applying heat to join the devices.

In some embodiments, the pneumatic network can be a hot embossed pneumatic network. A replica mold of the pneumatic network can be provided to imprint a space for the pneumatic network in a heat softened thermoplastic layer. The thermoplastic sheet retains the imprint of the embossed pneumatic network. The replica mold can be made in any suitable dimensions by conventional means, such as lithographic techniques, laser techniques or 3D printing or any other conventional methods.

In one aspect, parts or all of the components of a soft robotic device may be made of thermoplastic materials such as a thermoplastic polyurethane ("TPU"). TPUs become liquid-like when heated above a critical temperature, for example, above 60° C., or above 170° C., and become solid-like and retain shape after cool down. The cooled plastics can range from stiff to flexible. TPUs are formed by the reaction of: (1) diisocyanates with short-chain diols (so-called chain extenders) and (2) diisocyanates with long-chain diols. There is an unlimited number of possible combinations producible by varying the structure and/or molecular weight of the three reaction compounds. This allows for an enormous variety of TPUs with diverse physical properties. Thus, it is possible to select the appropriate TPUs having the appropriate elasticity for either the pneumatic network or a stiffer layer.

Non-limiting example embodiments include:

Embodiment 1: A method of patterning an object, comprising: providing a three-dimensional (3D) object; wrapping the 3D object in the flexible stamp having a micropattern on its surface; inserting the 3D object and the flexible stamp into a vacuum bag; applying vacuum to the 3D object and the flexible stamp within the vacuum bag; and transferring the micropattern of the flexible stamp to a surface of the 3D object.

Embodiment 2: Embodiment 1, further comprising: micropatterning a rigid material via photolithography; and fabricating the flexible stamp having the micropattern on its surface using the micropatterned rigid material.

Embodiment 3: Embodiment 2, further comprising fabricating a flexible stamp by: inverting the micropatterned rigid material to form a soft template having the micropattern on its surface; coating the soft template with an elastomeric material; curing the elastomeric material to form the flexible stamp; and peeling the flexible stamp off of the soft template.

Embodiment 4: Embodiment 3, wherein the soft template comprises silicone.

Embodiment 5: Embodiment 3, further comprising applying a treatment to a surface of the soft template.

Embodiment 6: Embodiment 5, wherein the surface treatment comprises trichloro perfluoro silane.

Embodiment 7: Embodiment 1, wherein the flexible stamp comprises an elastomeric film.

Embodiment 8: Embodiment 7, wherein the flexible stamp has a thickness between 20 and 500 microns.

Embodiment 9: Embodiment 1, wherein the micropattern has a thickness between one microns and 40 microns.

Embodiment 10: Embodiment 1, wherein the 3D object is formed from at least one of silicone, nitinol alloy, and polyurethane.

Embodiment 11: Embodiment 1, further comprising treating a surface of the 3D object to promote adhesion of the flexible stamp to the 3D object.

Embodiment 12: A micropatterned object formed by performing steps comprising: providing a three-dimensional (3D) object; wrapping the 3D object in a flexible stamp having a micropattern on its surface; inserting the 3D object and the flexible stamp into a vacuum bag; applying vacuum to the 3D object and the flexible stamp within the vacuum bag; and transferring the micropattern of the flexible stamp to a surface of the 3D object.

Embodiment 13. A method of manufacturing an implantable device, the method comprising: positioning a first portion of an inflatable balloon over a first portion of a sacrificial core; positioning a second portion of the inflatable balloon over a second portion of the sacrificial core such that the second portion of the inflatable balloon at least partially overlaps the first portion of the inflatable balloon; applying vacuum to the first portion of the inflatable balloon and the second portion of the inflatable balloon via a vacuum bag assembly; applying heat to the first portion of the inflatable balloon and the second portion of the inflatable balloon to form a thermoplastic bond between the first portion of the inflatable balloon and the second portion of the inflatable balloon; and dissolving the sacrificial core.

Embodiment 14: Embodiment 13, further comprising: wrapping the third portion of the inflatable balloon and the fourth portion of the inflatable balloon in a micropatterned stamp prior to applying the vacuum and the heat to the third portion of the inflatable balloon and the fourth portion of the inflatable balloon to impart micropatterned features on at least a portion of the surface of the inflatable balloon.

Embodiment 15: Embodiment 14, further comprising: micropatterning a silicon wafer via photolithography; inverting the micropatterned silicon wafer to form a master template; spin coating the master template with an elastomeric material; curing the elastomeric material to form the micropatterned stamp; and peeling the micropatterned stamp off of the master template.

Embodiment 16: Embodiment 13, further comprising: pressure forming a first film on a lower portion of a three-dimensional (3D) mold to form the first portion of the inflatable balloon; and pressure forming a second film on an upper portion of the 3D mold to form the second portion of the inflatable balloon.

Embodiment 17: Embodiment 16, further comprising: dissolving dry pellets of a resin material; and spin coating the dissolved resin on a flat template to form at least one of the first film and the second film.

Embodiment 18: Embodiment 17, wherein the resin material comprises polyurethane.

Embodiment 19: Embodiment 16, wherein at least one of the first film and the second film has a thickness between 30 microns and 40 microns.

Embodiment 20: Embodiment 13, further comprising: constructing a 3D mold of a septum using an additive manufacturing technique; inverting the 3D mold on a silicone mold; filling the silicone mold with dry resin pellets; applying heat and vacuum to the silicone mold and the dry resin pellets to form the septum; removing the septum from the silicone mold; and inserting the septum into a hole in the sacrificial core.

Embodiment 21: Embodiment 20, wherein dissolving the sacrificial core further comprises: puncturing the septum; and coupling the inflatable balloon to a perfusion system; and circulating water through an interior of the inflatable balloon via the perfusion system to dissolve the sacrificial core.

Embodiment 22: Embodiment 13, further comprising: wrapping an elastomeric string around the first portion of the inflatable balloon and the second portion of the inflatable balloon prior to applying heat to the first portion of the inflatable balloon and the second portion of the inflatable balloon.

Embodiment 23: Embodiment 13, further comprising: constructing a 3D mold of the sacrificial core using an additive manufacturing technique; inverting the 3D mold on a silicone mold; introducing a slurry into the silicone mold; applying heat and vacuum to the silicone mold to cause the slurry to form the sacrificial core; and removing the sacrificial core from the silicone mold.

Embodiment 24: An implantable device formed by performing steps comprising: positioning a first portion of an inflatable balloon over a lower portion of a sacrificial core; positioning a second portion of the inflatable balloon over an upper portion of the sacrificial core such that the second portion of the inflatable balloon at least partially overlaps the first portion of the inflatable balloon; applying vacuum to the first portion of the inflatable balloon and the second portion of the inflatable balloon via a vacuum bag assembly; applying heat to the first portion of the inflatable balloon and the second portion of the inflatable balloon to form a thermoplastic bond between the first portion of the inflatable balloon and the second portion of the inflatable balloon; and dissolving the sacrificial core.

Embodiment 25: A soft robotic device comprising: a first layer bonded to a second layer, wherein at least one layer is comprised of an extensible thermoplastic material; at least one layer comprises a pneumatic network; and wherein an initial conformation of the soft robotic device is a low-volume conformation or a zero-volume configuration.

Embodiment 26: Embodiment 25, wherein the pneumatic network is in contact with a pressurizing source such that the pressurizing source facilitates transition of the soft robot device from a low-volume or zero-volume conformation to an extended or actuated conformation via pressurizing the pneumatic network.

Embodiment 27: Embodiment 26, wherein the pneumatic network comprises a plurality of channels arranged in a pattern such that, upon pressurization by the pressurizing source, the soft robotic device undergoes at least two types of actuation.

Embodiment 28: Embodiment 25, wherein the thermoplastic material comprises a polyurethane or silicone, or ant extensible polymer.

Embodiment 29: Embodiment 25, wherein the soft robotic device is a heart valve.

Embodiment 30: Embodiment 25, wherein the soft robotic device is a stent.

Embodiment 31: Embodiment 25, wherein the soft robotic device is an in-plane or out-of-plane bending device.

Embodiment 32: Embodiment 25, wherein the soft robotic device is a rotary device, an axial rotary device or a bi-axial rotary device.

Embodiment 33: Embodiment 25, wherein the soft robotic device is a gripping device.

Embodiment 34: Embodiment 25, wherein the soft robotic device is a robotic swimmer.

Embodiment 35: Embodiment 25, wherein the soft robotic device is substantially planar in the initial conformation.

Embodiment 36: Embodiment 25, wherein the soft robotic device is rolled in the initial conformation.

Embodiment 37: A method for constructing the soft robotic device of Embodiment 25 comprising: providing a first layer and a second layer; applying heat and/or pressure to the first and second layers to bond the layers; and sealing first layer and second layers together using a laser welding technique such that a pattern is obtained.

Embodiment 38: A method for constructing the soft robotic device of Embodiment 25 comprising: providing a film layer; cutting a film layer pattern from the film layer; providing a first layer and a second layer; combining the first and second layers with the film layer pattern such that the first layer is disposed on a first side, the second layer is disposed on a second side and the film layer pattern is disposed in between the first and second layers; applying heat and/or pressure to the first and second layers with film layer pattern disposed in between first and second layers to thermally bond the first and second layers; discarding the film layer pattern such that seams are created on first and/or second layers; and cutting along the seams on first and/or second layers such that a pattern is obtained.

Embodiment 39: Embodiment 38, wherein the film layer comprises a water-soluble film.

Embodiment 40: Embodiment 38, wherein the film layer comprises a material with higher transition temperature than first and/or second thermoplastic layers.

Embodiment 41: Embodiment 38, wherein the first and second layers form a first actuator, the method further comprising laminating the first actuator to a second actuator.

As used herein, the singular terms "a," "an," and "the" may include plural referents unless the context clearly dictates otherwise.

As used herein, relative terms, such as "above," "below," "up," "left," "right," "down," "top," "bottom," "vertical," "horizontal," "side," "higher," "lower," "upper," "over," "under," "inner," "interior," "outer," "exterior," "front," "back," "upwardly," "lower," "downwardly," "vertical," "vertically," "lateral," "laterally" and the like refer to an orientation of a set of components with respect to one another; this orientation is in accordance with the drawings, but is not required during manufacturing or use.

As used herein, the terms "connect," "connected," and "connection" refer to an operational coupling or linking. Connected components can be directly or indirectly coupled to one another, for example, through another set of components.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments and implementations thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments and implementations of the present disclosure, which are not specifically illustrated. The specification and drawings are to be regarded as illustrative rather than restrictive. Modifications may be made to adapt a particular situation, material, composition of matter, technique, or process to the objective, spirit and scope of the present disclosure. All such modifications are intended to be within the scope of the claims appended hereto. While the techniques disclosed herein have been described with reference to particular operations performed in a particular order, it will be understood that these operations may be combined, sub-divided, or re-ordered to form an equivalent technique without departing from the teachings of the present disclosure. Accordingly, unless specifically indicated herein, the order and grouping of the operations are not limitations of the present disclosure.

What is claimed is:

1. A method of patterning a biocompatible three-dimensional (3D) object, comprising:
    wrapping a flexible stamp around the 3D object, the flexible stamp having a micropattern on a micropatterned side, the flexible stamp being conformable to a surface of the 3D object;
    inserting the 3D object wrapped in the flexible stamp into a vacuum bag such that the micropatterned side of the flexible stamp faces the surface of the 3D object; and
    applying vacuum to the 3D object and the flexible stamp within the vacuum bag to induce a differential pressure between inside and outside of the vacuum bag to cause the vacuum bag to press inward against the flexible stamp and thereby conform the flexible stamp to the surface of the 3D object to transfer the micropattern of the flexible stamp to the surface of the 3D object;
    wherein the flexible stamp is a flat sheet with a thickness that is no greater than 500 microns.

2. The method of claim 1, wherein the 3D object is a medical device.

3. The method of claim 2, wherein the medical device is an implantable medical device.

4. The method of claim 1, wherein applying the vacuum to the 3D object and the flexible stamp within the vacuum bag pushes the flexible stamp into contact with the 3D stamp without inducing deformation in the micropattern of the flexible stamp.

5. The method of claim 1, further comprising:
    micropatterning a rigid material; and
    fabricating the flexible stamp having the micropattern on its surface using the micropatterned rigid material.

6. The method of claim 5, wherein the rigid material is micropatterned via photolithography.

7. The method of claim 5, further comprising fabricating the flexible stamp by:
    inverting the micropatterned rigid material to form a soft template having the micropattern on its surface;
    coating the soft template with an elastomeric material;
    curing the elastomeric material to form the flexible stamp; and
    peeling the flexible stamp off of the soft template.

8. The method of claim 7, wherein the soft template comprises silicone.

9. The method of claim 7, further comprising applying a treatment to a surface of the soft template.

10. The method of claim 9, wherein the treatment comprises trichloro perfluoro silane.

11. The method of claim 1, wherein the flexible stamp comprises an elastomeric film.

12. The method of claim 11, wherein the thickness of the flexible stamp is between 20 and 500 microns.

13. The method of claim 1, wherein the micropattern has a thickness between 1 micron and 40 microns.

14. The method of claim 1, wherein the 3D object is formed from at least one of silicone, nitinol alloy, and polyurethane.

15. The method of claim 1, further comprising treating a surface of the 3D object to promote adhesion of the flexible stamp to the 3D object.

16. The method of claim 1, further comprising:
    micropatterning, via photolithography, a rigid material with the micropattern; and
    fabricating the flexible stamp having the micropattern on its surface by:
        inverting the micropatterned rigid material to form a soft template having the micropattern on its surface;
        applying a treatment to a surface of the soft template;
        coating the soft template with an elastomeric material;
        curing the elastomeric material to form the flexible stamp; and
        peeling the flexible stamp off of the soft template.

17. The method of claim 1, further comprising dipping the 3D object into a polymer film to produce a thin polymer film on the surface of the 3D object, wherein transferring the micropattern of the flexible stamp to the surface of the 3D object leaves the thin polymer film with a surface pattern corresponding to the micropattern of the flexible stamp.

18. The method of claim 1, further comprising applying a surface treatment to the surface of the 3D object, wherein transferring the micropattern of the flexible stamp to the surface of the 3D object comprises transferring the micropattern to the surface treatment on the surface of the 3D object.

19. The method of claim 1, further comprising applying a biocompatible coating to at least a portion of the surface of the 3D object, and peeling the flexible stamp off the surface of the 3D object to leave the biocompatible coating with a surface pattern corresponding to the micropattern of the flexible stamp.

20. A medical device with a micropattern, the medical device being a biocompatible 3D object micropatterned by the method of claim 1.

21. The method of claim 1, wherein the flexible stamp conforms to a plurality of geometries without requiring an operator to know a geometry of the 3D object in advance.

* * * * *